US008900148B2

(12) United States Patent
Tanabe

(10) Patent No.: US 8,900,148 B2
(45) Date of Patent: Dec. 2, 2014

(54) ULTRASOUND DIAGNOSTIC APPARATUS

(75) Inventor: Tsuyoshi Tanabe, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 78 days.

(21) Appl. No.: 13/402,463

(22) Filed: Feb. 22, 2012

(65) Prior Publication Data

US 2012/0232396 A1 Sep. 13, 2012

(30) Foreign Application Priority Data

Mar. 9, 2011 (JP) ................. 2011-051508
Mar. 9, 2011 (JP) ................. 2011-051727
Mar. 9, 2011 (JP) ................. 2011-051888
Mar. 9, 2011 (JP) ................. 2011-051900
Mar. 28, 2011 (JP) ................. 2011-070036

(51) Int. Cl.
*A61B 8/14* (2006.01)
*A61B 8/08* (2006.01)
*A61B 8/00* (2006.01)
*G01S 7/52* (2006.01)
*G01S 15/89* (2006.01)

(52) U.S. Cl.
CPC ............. *A61B 8/00* (2013.01); *A61B 8/5253* (2013.01); *A61B 8/4472* (2013.01); *G01S 15/8915* (2013.01); *G01S 7/52085* (2013.01); *G01S 7/5205* (2013.01); *G01S 7/52079* (2013.01); *G01S 15/8995* (2013.01); *A61B 8/546* (2013.01)
USPC ........... 600/447; 600/437; 600/443; 600/458; 600/459; 600/463

(58) Field of Classification Search
CPC .... A61B 8/4281; A61B 8/4472; A61B 8/469; A61B 8/5253; A61B 8/546
USPC .......................... 600/437, 443, 458, 459, 463
See application file for complete search history.

(56) References Cited

U.S. PATENT DOCUMENTS 6,106,471 A 8/2000 Wiesauer et al.
6,210,328 B1 4/2001 Robinson et al.
(Continued)

FOREIGN PATENT DOCUMENTS

JP 2000-70265 3/2000
JP 2002-526224 8/2002
(Continued)

OTHER PUBLICATIONS

Japanese Official Action—2011-051727—Aug. 13, 2013.
(Continued)

*Primary Examiner* — Baisakhi Roy
(74) *Attorney, Agent, or Firm* — Young & Thompson

(57) ABSTRACT

The ultrasound probe transmits and receives ultrasonic waves in different directions and the diagnostic apparatus body combines a plurality of images captured in the different directions of transmission and reception to produce an ultrasound image. In this process, the ultrasound diagnostic apparatus measures the temperature of the ultrasound probe to change the ultrasound transmission and reception for producing a composite ultrasound image or makes the directions of transmission and reception in the last ultrasound image in one composite ultrasound image coincide with those in the first ultrasound image in its temporally adjacent composite ultrasound image. The ultrasound diagnostic apparatus thus enables consistent ultrasound diagnosis against heat generated in the integrated circuit board of the ultrasound probe while simplifying the control of the ultrasound transmission and reception.

41 Claims, 23 Drawing Sheets

(56) References Cited

U.S. PATENT DOCUMENTS

| | | |
|---|---|---|
| 7,828,731 B2 | 11/2010 | Baba et al. |
| 2004/0210137 A1 | 10/2004 | Baba et al. |
| 2008/0146940 A1* | 6/2008 | Jenkins et al. ............... 600/463 |
| 2009/0088638 A1 | 4/2009 | Sato et al. |
| 2010/0081938 A1* | 4/2010 | Kato ............................ 600/458 |
| 2010/0160786 A1* | 6/2010 | Nordgren et al. ............ 600/459 |
| 2011/0118599 A1* | 5/2011 | Osumi ......................... 600/437 |
| 2012/0232392 A1* | 9/2012 | Tanabe et al. ............... 600/443 |

FOREIGN PATENT DOCUMENTS

| | | |
|---|---|---|
| JP | 2003-070786 | 3/2003 |
| JP | 2005-058321 | 3/2005 |
| JP | 2006-095151 | 4/2006 |
| JP | 2006-340890 | 12/2006 |
| JP | 2008-068017 | 3/2008 |
| JP | 2009-82469 | 4/2009 |
| JP | 2010-528697 | 8/2010 |

OTHER PUBLICATIONS

Japanese Official Action—2011-051727—Feb. 12, 2013.
Japanese Official Action—2011-070036—Feb. 19, 2013.
Japanese Official Action—2011-051900—Feb. 26, 2013.

\* cited by examiner

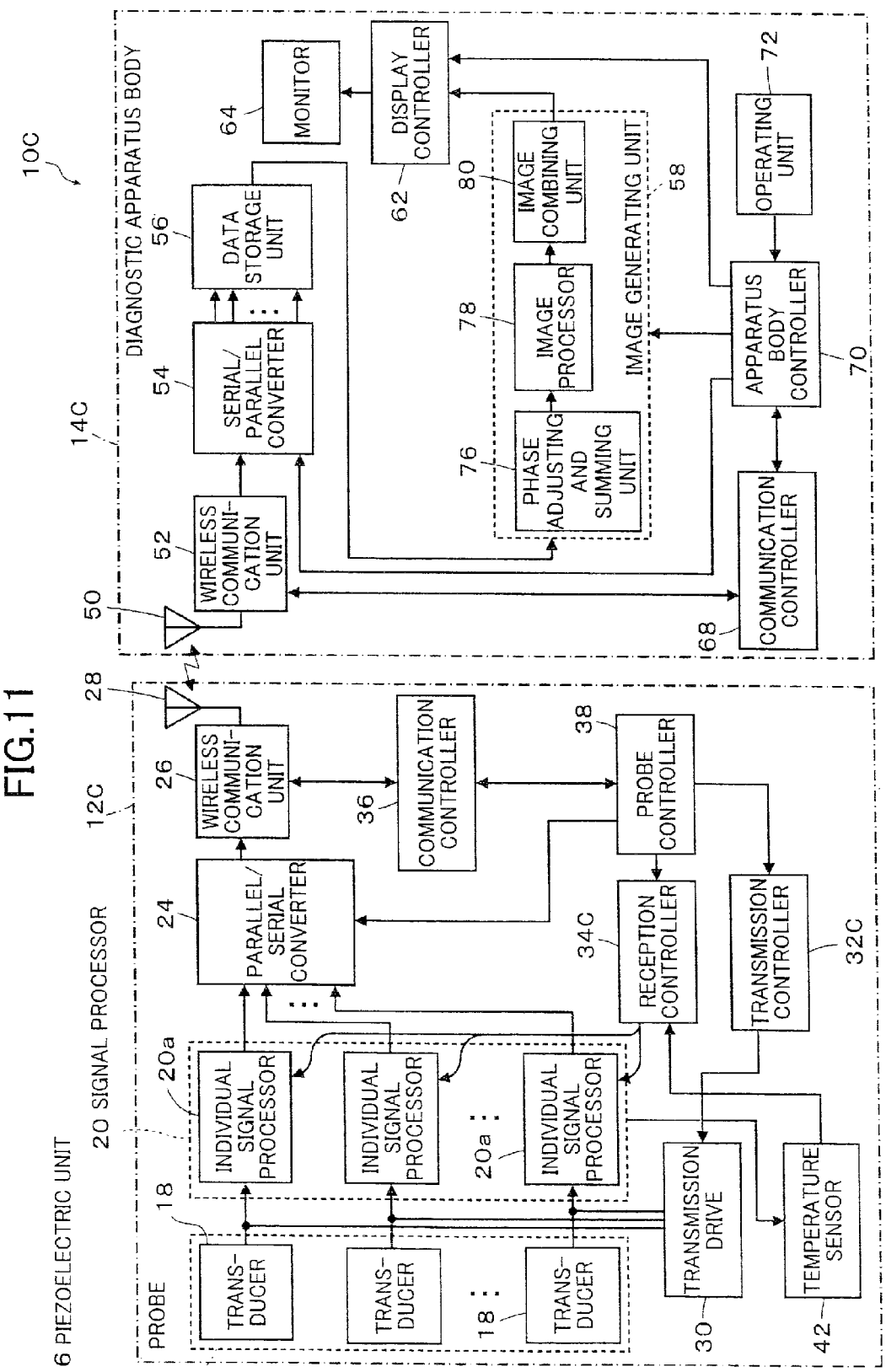

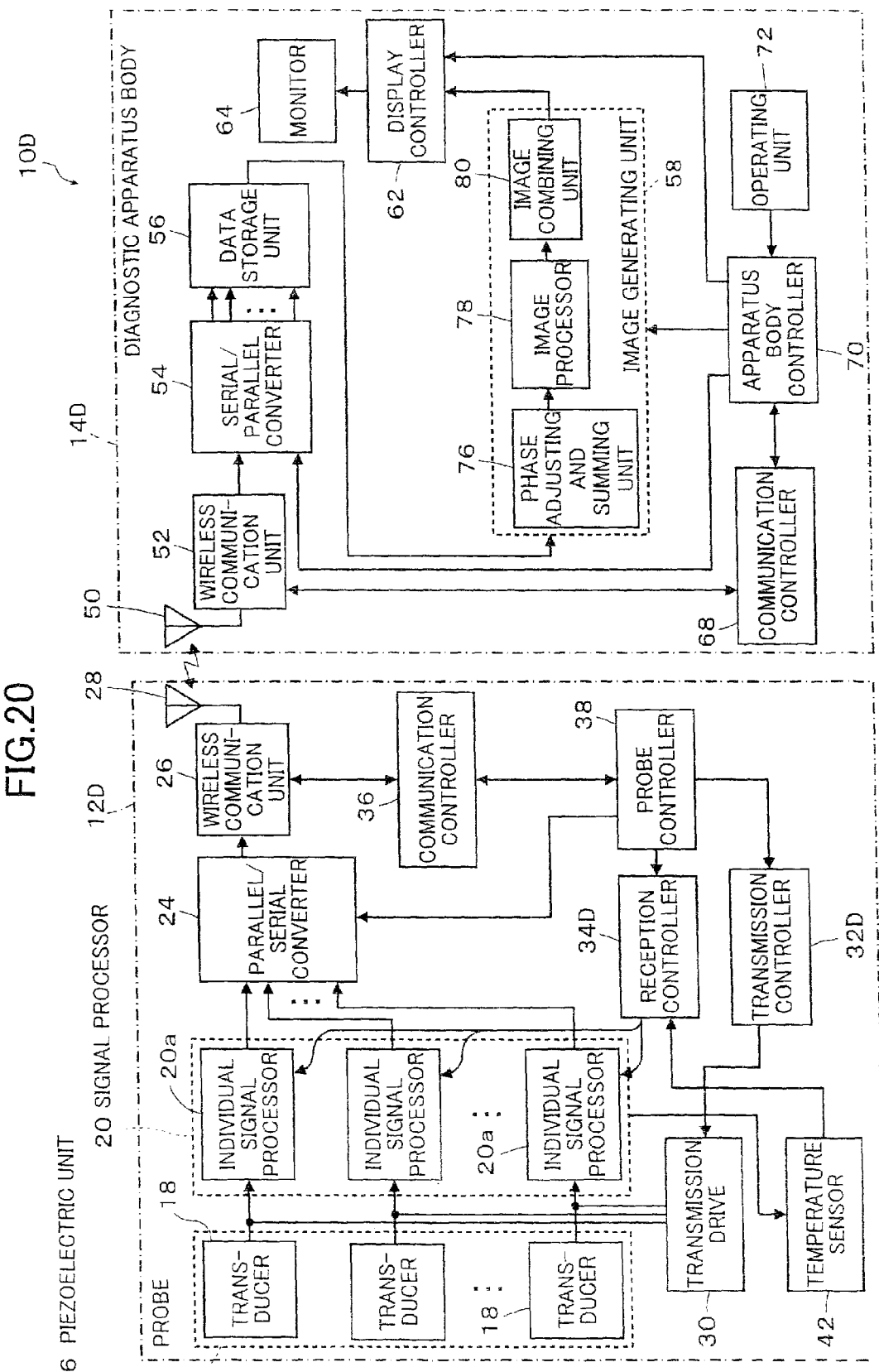

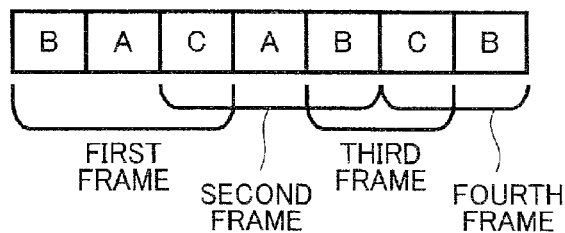
FIG.33A
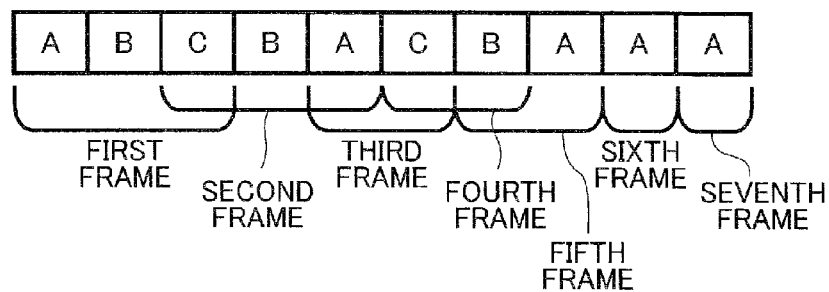
FIG.33B
FIG.34
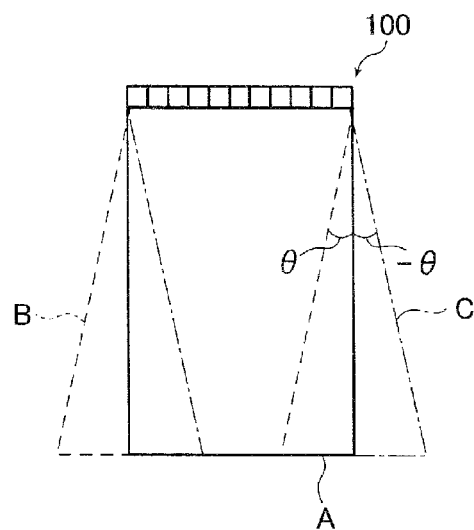

ULTRASOUND DIAGNOSTIC APPARATUS

BACKGROUND OF THE INVENTION

The present invention relates to an ultrasound diagnostic apparatus. The invention more particularly relates to an ultrasound diagnostic apparatus capable of suppressing heat generation from an ultrasound probe while easily controlling the ultrasound transmission and reception in spatial compounding.

Ultrasound diagnostic apparatus using ultrasound images are put to practical use in the medical field.

In general, an ultrasound diagnostic apparatus includes an ultrasound probe (hereinafter referred to as "probe") and a diagnostic apparatus body. In the ultrasound diagnostic apparatus, the probe transmits ultrasonic waves toward a subject and receives ultrasonic echoes from the subject. The diagnostic apparatus body electrically processes the reception signals received by and outputted from the probe to produce an ultrasound image.

So-called "speckle" (speckle noise/speckle pattern) is known as a factor that may deteriorate the image quality of an ultrasound image in the ultrasound diagnostic apparatus. Speckle is white spot noise caused by the mutual interference of scattered waves generated by numerous scattering sources which are present in a subject and have a smaller wavelength than that of an ultrasonic wave.

Spatial compounding as described in JP 2005-58321 A and JP 2003-70786 A is known as a method of reducing such speckle in the ultrasound diagnostic apparatus.

As conceptually shown in FIG. 34, spatial compounding is a technique which involves performing a plurality of types of ultrasound transmission and reception in mutually different directions (at mutually different scanning angles) between a piezoelectric unit 100 and a subject, and combining ultrasound images obtained by the plurality of types of ultrasound transmission and reception to produce a composite ultrasound image.

More specifically, in the example shown in FIG. 34, three types of ultrasound transmission and reception are performed which include the ultrasound transmission and reception as in the normal ultrasound image generation (normal transmission and reception), the ultrasound transmission and reception in a direction inclined by an angle of $\theta$ with respect to the direction of the normal transmission and reception, and the ultrasound transmission and reception in a direction inclined by an angle of $-\theta$ with respect to the direction of the normal transmission and reception.

An ultrasound image A (solid line) obtained by the normal transmission and reception, an ultrasound image B (broken line) obtained by the transmission and reception in the direction inclined by the angle of $\theta$, and an ultrasound image C (chain line) obtained by the transmission and reception in the direction inclined by the angle of $-\theta$ are combined to produce a composite ultrasound image covering the region of the ultrasound image A shown by the solid line.

The probe making up the ultrasound diagnostic apparatus includes a piezoelectric unit which transmits ultrasonic waves to a subject, receives ultrasonic echoes generated by reflection of the ultrasonic waves on the subject and outputs the received ultrasonic echoes as electric signals (reception signals).

Recently, the probe may also be provided with an integrated circuit board for use in amplifying the reception signals outputted from the piezoelectric unit, performing A/D conversion or other processing, changing the timing of transmission and reception of ultrasonic waves in the piezoelectric unit, wireless communication with the diagnostic apparatus body without using any cord, and reducing noise.

As well known, the piezoelectric unit generates heat through the ultrasound transmission and reception.

Higher-definition ultrasound images are obtained with increasing power of ultrasonic waves transmitted from the piezoelectric unit. However, the amount of heat generated from the piezoelectric unit is also increased with increasing power of ultrasonic waves transmitted from the piezoelectric unit.

The integrated circuit board also generates heat through reception signal processing.

That is, the probe generates heat through ultrasound transmission and reception.

The heat generation from the probe destabilizes the drive of the piezoelectric unit and the operation of each circuit of the integrated circuit board. As a result, output signals from the transmitted or received ultrasonic waves are destabilized to further destabilize the signal processing in the integrated circuit board. That is, the heat generation from the probe lowers the image quality of ultrasound images.

Therefore, it is necessary in the ultrasound diagnostic apparatus to suppress the temperature increase within the probe as much as possible in order to consistently obtain high-definition ultrasound images.

As also described above, spatial compounding enables speckle on the resulting ultrasound image to be reduced.

On the other hand, since the directions of ultrasound transmission and reception are to be changed for each ultrasound image used to produce a composite ultrasound image, the control of ultrasound transmission and reception becomes complicated.

SUMMARY OF THE INVENTION

An object of the present invention is to solve the foregoing prior art problems and to provide an ultrasound diagnostic apparatus which, when a composite ultrasound image is produced from ultrasound images by spatial compounding, is capable of suppressing the temperature increase within the ultrasound probe while minimizing the image quality deterioration of ultrasound images even if the temperature is increased.

Another object of the invention is to provide an ultrasound diagnostic apparatus capable of reducing the switching control of the directions of ultrasound transmission and reception in the production of an ultrasound image through spatial compounding, thereby simplifying the control of the ultrasound transmission and reception upon spatial compounding.

In order to achieve the above objects, a first aspect of the invention provides an ultrasound diagnostic apparatus comprising:

an ultrasound probe configured to transmit ultrasonic waves into a subject and receive ultrasonic echoes generated by reflection of the ultrasonic waves from the subject, the ultrasound probe including a signal processor for processing reception signals based on the ultrasonic echoes and a temperature sensor for measuring a temperature at a predetermined position; and a diagnostic apparatus body configured to generate ultrasound images in accordance with the reception signals processed in the signal processor of said ultrasound probe, wherein said ultrasound probe is configured to perform a plurality of types of ultrasound transmission and in mutually different directions of ultrasound transmission and reception and said diagnostic apparatus body is configured to combine ultrasound images based on each of the plurality of types of ultrasound transmission and reception, and wherein, upon production of the composite ultrasound image in said diagnostic apparatus body, said ultrasound probe is configured to change ultrasound transmission and reception for producing said composite ultrasound image in accordance with a temperature measurement result obtained with said temperature sensor.

In the ultrasound diagnostic apparatus according to the first aspect of the invention, upon the production of the composite ultrasound image in the diagnostic apparatus body, the ultrasound probe preferably performs the ultrasound transmission and reception for producing the composite ultrasound image through the plurality of types of ultrasound transmission and reception or through at least one type of ultrasound transmission and reception after reduction of one or more types of ultrasound transmission and reception from the plurality of types of ultrasound transmission and reception based on the temperature measurement result obtained with the temperature sensor.

The temperature sensor preferably measures a temperature of the signal processor.

Upon the production of the composite ultrasound image in the diagnostic apparatus body, the ultrasound probe preferably performs ultrasound transmission and reception for obtaining a main image as an ultrasound image in a preset predetermined output region by one of the plurality of types of ultrasound transmission and reception.

Preferably, a temperature T1 and a temperature T2 higher than the temperature T2 are set as thresholds and, upon the production of the composite ultrasound image in the diagnostic apparatus body, depending on the temperature measurement result obtained with the temperature sensor, the ultrasound probe performs the plurality of types of ultrasound transmission and reception when the temperature measurement result is less than the temperature T1, performs a set minimum number of types of ultrasound transmission and reception when the temperature measurement result is equal to or more than the temperature T2, and performs a given number of types of ultrasound transmission and reception which is smaller than the number of the plurality of types of transmission and reception but is larger than the set minimum number of types of ultrasound transmission and reception when the temperature measurement result is equal to or more than the temperature T1 but less than the temperature T2.

Preferably, a temperature T1 and a temperature T2 higher than the temperature T2 are set as thresholds and, upon the production of the composite ultrasound image in the diagnostic apparatus body, depending on the temperature measurement result obtained with the temperature sensor, the ultrasound probe performs the plurality of types of ultrasound transmission and reception when the temperature measurement result is less than the temperature T1, and when the temperature measurement result is equal to or more than the temperature T1, performs, in one composite ultrasound image, the at least one type of ultrasound transmission and reception after the reduction of the one or more types of ultrasound transmission and reception from the plurality of types of ultrasound transmission and reception and performs, in its temporally consecutive composite ultrasound image, the plurality of types of ultrasound transmission and reception or the at least one type of ultrasound transmission and reception after the reduction of the one or more types of ultrasound transmission and reception from the plurality of types of ultrasound transmission and reception, a number of types of ultrasound transmission and reception reduced from the number of the plurality of types of ultrasound transmission and reception being different in two consecutive ultrasound images including the one composite ultrasound image and its temporally consecutive composite ultrasound image.

The ultrasound probe preferably performs the ultrasound transmission and reception by reducing the one or more types of ultrasound transmission and reception from the plurality of types of ultrasound transmission and reception in one of the two temporally consecutive composite ultrasound images when the temperature measurement result is equal to or more than the temperature T1 but less than the temperature T2.

The ultrasound probe preferably performs the ultrasound transmission and reception by reducing the one or more types of ultrasound transmission and reception from the plurality of types of ultrasound transmission and reception in both of the two temporally consecutive composite ultrasound images when the temperature measurement result is equal to or more than the temperature T2.

The ultrasound probe preferably transmits and receives the ultrasonic waves in identical directions for a last ultrasound image in one composite ultrasound image and a first ultrasound image in its temporally consecutive composite ultrasound image.

Upon the production of the composite ultrasound image in the diagnostic apparatus body, the ultrasound probe preferably performs the ultrasound transmission and reception so as to reduce temporally consecutive ultrasound image when two or more types of ultrasound transmission and reception are reduced from the plurality of types of ultrasound transmission and reception.

Upon the production of the composite ultrasound image in the diagnostic apparatus body, the ultrasound probe preferably performs the ultrasound transmission and reception so as to reduce a last ultrasound image in a composite ultrasound image and a first ultrasound image in its temporally consecutive composite ultrasound image when the one or more types of ultrasound transmission and reception are reduced from the plurality of types of ultrasound transmission and reception.

In the ultrasound diagnostic apparatus according to the first aspect of the invention, upon the production of the composite ultrasound image in the diagnostic apparatus body, the ultrasound probe preferably adjusts conditions of the ultrasound transmission and reception so as to change an image quality of an ultrasound image to be combined in the diagnostic apparatus body in accordance with the temperature measurement result obtained with the temperature sensor.

The temperature sensor preferably measures a temperature of the signal processor.

The ultrasound probe preferably changes at least one of a number of available channels and a number of sound rays to adjust the conditions of the ultrasound transmission and reception.

Preferably, a temperature T3 and a temperature T4 higher than the temperature T3 are set as thresholds, and ultrasound transmission and reception at a normal image quality level corresponding to ultrasound images of predetermined image quality, ultrasound transmission and reception at a low image quality level corresponding to ultrasound images of lowest image quality, and ultrasound transmission and reception at a medium image quality level corresponding to ultrasound images having image quality lower than the normal image quality level but higher than the low image quality level are set in the conditions of the ultrasound transmission and reception for obtaining the ultrasound image to be combined.

Upon the production of the composite ultrasound image in the diagnostic apparatus body, depending on the temperature measurement result obtained with the temperature sensor, the ultrasound probe preferably performs all of the plurality of types of ultrasound transmission and reception at the normal image quality level when the temperature measurement result is less than the temperature T3.

Upon the production of the composite ultrasound image in the diagnostic apparatus body, depending on the temperature measurement result obtained with the temperature sensor, the ultrasound probe preferably performs at least two of the plurality of types of ultrasound transmission and reception at the medium image quality level when the temperature measurement result is equal to or more than the temperature T3 but less than the temperature T4 and at the low image quality level when the temperature measurement result is equal to or more than the temperature T4.

Upon the production of the composite ultrasound image in the diagnostic apparatus body, depending on the temperature measurement result obtained with the temperature sensor, the ultrasound probe preferably performs at least two of the plurality of types of ultrasound transmission and reception at the medium image quality level when the temperature measurement result is equal to or more than the temperature T3 but less than the temperature T4, and performs at least one of the plurality of types of ultrasound transmission and reception at the medium image quality level and one or more types of ultrasound transmission and reception except the at least one of the plurality of types of ultrasound transmission and reception at the low image quality level when the temperature measurement result is equal to or more than the temperature T4.

Upon the production of the composite ultrasound image in the diagnostic apparatus body, depending on the temperature measurement result obtained with the temperature sensor, the ultrasound probe preferably performs at least two of the plurality of types of ultrasound transmission and reception at the medium image quality level when the temperature measurement result is equal to or more than the temperature T3 but less than the temperature T4, and performs the at least two of the plurality of types of ultrasound transmission and reception at the low image quality level and all of one or more types of ultrasound transmission and reception except the at least two of the plurality of types of ultrasound transmission and reception at the medium image quality level when the temperature measurement result is equal to or more than the temperature T4.

Preferably, upon the production of the composite ultrasound image in the diagnostic apparatus body, the ultrasound probe performs ultrasound transmission and reception for obtaining a main image as an ultrasound image in a preset predetermined output region by one of the plurality of types of ultrasound transmission and reception and the ultrasound transmission and reception for the main image are performed at the normal image quality level.

The ultrasound probe preferably transmits and receives the ultrasonic waves in identical directions for a last ultrasound image in one composite ultrasound image and a first ultrasound image in its temporally consecutive composite ultrasound image.

In the ultrasound diagnostic apparatus according to the first aspect of the invention, upon the production of the composite ultrasound image in the diagnostic apparatus body, the ultrasound probe preferably adjusts a depth of the reception signals to be processed by the signal processor so as to change a depth of an ultrasound image to be combined in the diagnostic apparatus body in accordance with the temperature measurement result obtained with the temperature sensor.

The temperature sensor preferably measures a temperature of the signal processor.

Preferably, a temperature T5 and a temperature T6 higher than the temperature T5 are set as thresholds and a normal depth according to which the reception signals are processed up to a predetermined depth, a small depth according to which the reception signals are processed up to a shallowest depth and a medium depth according to which the reception signals are processed up to a depth smaller than the normal depth but larger than the small depth are set for the depth of the reception signals to be processed by the signal processor.

Upon the production of the composite ultrasound image in the diagnostic apparatus body, depending on the temperature measurement result obtained with the temperature sensor, the ultrasound probe preferably performs all of reception signal processing in the plurality of types of ultrasound transmission and reception up to the normal depth when the temperature measurement result is less than the temperature T5.

Upon the production of the composite ultrasound image in the diagnostic apparatus body, depending on the temperature measurement result obtained with the temperature sensor, the ultrasound probe preferably performs reception signal processing in at least two of the plurality of types of ultrasound transmission and reception up to the medium depth when the temperature measurement result is equal to or more than the temperature T5 but less than the temperature T6 and up to the small depth when the temperature measurement result is equal or more than the temperature T6.

Upon the production of the composite ultrasound image in the diagnostic apparatus body, depending on the temperature measurement result obtained with the temperature sensor, the ultrasound probe preferably performs reception signal processing at least two of the plurality of types of ultrasound transmission and reception up to the medium depth when the temperature measurement result is equal to or more than the temperature T5 but less than the temperature T6, and alternately repeats reception signal processing up to the small depth in at least two of the plurality of types of ultrasound transmission and reception and reception signal processing up to the medium depth in the at least two of the plurality of types of ultrasound transmission and reception in temporally consecutive composite ultrasound images when the temperature measurement result is equal to or more than the temperature T5.

Upon the production of the composite ultrasound image in the diagnostic apparatus body, depending on the temperature measurement result obtained with the temperature sensor, the ultrasound probe preferably performs reception signal processing in at least two of the plurality of types of ultrasound transmission and reception up to the medium depth when the temperature measurement result is equal to or more than the temperature T5 but less than the temperature T6 and performs reception signal processing in at least one of the plurality of types of ultrasound transmission and reception up to the medium depth and one or more types of ultrasound transmission and reception except the at least one of the plurality of types of ultrasound transmission and reception up to the small depth when the temperature measurement result is equal to or more than the temperature T6.

Ultrasound images subjected to the reception signal processing up to the medium depth and ultrasound images subjected to the reception signal processing up to the small depth are preferably different in order of processing in temporally consecutive composite ultrasound images when the temperature measurement result is equal to or more than the temperature T6.

Upon the production of the composite ultrasound image in the diagnostic apparatus body, depending on the temperature measurement result obtained with the temperature sensor, the ultrasound probe preferably performs reception signal processing in at least two of the plurality of types of ultrasound transmission and reception up to the medium depth when the temperature measurement result is equal to or more than the temperature T5 but less than the temperature T6 and performs the reception signal processing in the at least two of the plurality of types of ultrasound transmission and reception up to the small depth and all of one or more types of ultrasound transmission and reception except the at least two of the plurality of types of ultrasound transmission and reception up to the medium depth when the temperature measurement result is equal to or more than the temperature T6.

Preferably, upon the production of the composite ultrasound image in the diagnostic apparatus body, the ultrasound probe performs ultrasound transmission and reception for obtaining a main image as an ultrasound image in a preset predetermined output region by one of the plurality of types of ultrasound transmission and reception and reception signals obtained by the ultrasound transmission and reception for the main image are processed up to the normal depth.

The ultrasound probe preferably transmits and receives the ultrasonic waves in identical directions for a last ultrasound image in one composite ultrasound image and a first ultrasound image in its temporally consecutive composite ultrasound image.

In the ultrasound diagnostic apparatus according to the first aspect of the invention, upon the production of the composite ultrasound image in the diagnostic apparatus body, the ultrasound probe preferably adjusts reception signal processing performed by the signal processor so as to reduce a number of sound rays in a region beyond a predetermined depth in an ultrasound image to be combined by the diagnostic apparatus body depending on the temperature measurement result obtained with the temperature sensor, and upon the production of the composite ultrasound image in the diagnostic apparatus body, the diagnostic apparatus body interpolates sound rays eliminated beyond the predetermined depth with their surrounding sound rays to produce the ultrasound image.

The temperature sensor preferably measures a temperature of the signal processor.

Preferably, a temperature T7 and a temperature T8 higher than the temperature T7 are set as thresholds, and a normal depth up to which the number of sound rays is not reduced, a small depth which is shallowest, and a medium depth which is smaller than the normal depth but is larger than the small depth are set for the predetermined depth beyond which the number of sound rays is reduced.

Upon the production of the composite ultrasound image in the diagnostic apparatus body, depending on the temperature measurement result obtained with the temperature sensor, the ultrasound probe preferably processes all of ultrasound images up to the normal depth when the temperature measurement result is less than the temperature T7.

Upon the production of the composite ultrasound image in the diagnostic apparatus body, depending on the temperature measurement result obtained with the temperature sensor, the ultrasound probe preferably reduces the number of sound rays beyond the medium depth in at least two of ultrasound images when the temperature measurement result is equal to or more than the temperature T7 but less than the temperature T8, and reduces the number of sound rays beyond the small depth in the at least two of ultrasound images when the temperature measurement result is equal to or more than the temperature T8.

Upon the production of the composite ultrasound image in the diagnostic apparatus body, depending on the temperature measurement result obtained with the temperature sensor, the ultrasound probe preferably reduces the number of sound rays beyond the medium depth in at least two of ultrasound images when the temperature measurement result is equal to or more than the temperature T7 but less than the temperature T8, and reduces the number sound rays beyond the medium depth in at least one of ultrasound images and one or more ultrasound images except the at least one of ultrasound images beyond the small depth when the temperature measurement result is equal to or more than the temperature T8.

Upon the production of the composite ultrasound image in the diagnostic apparatus body, depending on the temperature measurement result obtained with the temperature sensor, the ultrasound probe preferably reduces the number of sound rays beyond the medium depth in at least two of ultrasound images when the temperature measurement result is equal to or more than the temperature T7 but less than the temperature T8, and reduces the number of sound rays beyond the small depth in the at least two of ultrasound images and all of one or more ultrasound images except the at least two of ultrasound images beyond the medium depth when the temperature measurement result is equal to or more than the temperature T8.

Preferably, upon the production of the composite ultrasound image in the diagnostic apparatus body, the ultrasound probe performs ultrasound transmission and reception for obtaining a main image as an ultrasound image in a preset predetermined output region by one of the plurality of types of ultrasound transmission and reception and an ultrasound image obtained by the ultrasound transmission and reception for the main image has the normal depth.

The ultrasound probe preferably transmits and receives the ultrasonic waves in identical directions for a last ultrasound image in one composite ultrasound image and a first ultrasound image in its temporally consecutive composite ultrasound image.

A second aspect of the invention provides an ultrasound diagnostic apparatus comprising:

an ultrasound probe configured to transmit ultrasonic waves into a subject and receive ultrasonic echoes generated by reflection of the ultrasonic waves from the subject; and a diagnostic apparatus body configured to generate ultrasound images in accordance with the reception signals processed in the signal processor of said ultrasound probe, wherein said ultrasound probe is configured to perform a plurality of types of ultrasound transmission and in mutually different directions of ultrasound transmission and reception and said diagnostic apparatus body is configured to combine ultrasound images based on each of the plurality of types of ultrasound transmission and reception, and wherein said ultrasound probe configured to perform said plurality of types of ultrasound transmission and reception so as to transmit and receive the ultrasonic waves in identical directions in a last ultrasound image of one composite ultrasound image and a first ultrasound image of its temporally adjacent composite ultrasound image.

In the ultrasound diagnostic apparatus according to the second aspect of the invention, the probe preferably further comprises a transmission controller for controlling transmission of the ultrasonic waves from the piezoelectric unit and a signal processor for processing the reception signals outputted from the piezoelectric unit.

At least one of the diagnostic apparatus body and the ultrasound probe preferably includes a selector for selecting a number of ultrasound images to be combined to produce the composite ultrasound image.

At least one of a predetermined number of temporally consecutive composite ultrasound images preferably has a different number of ultrasound images to be combined.

At least one of a predetermined number of temporally consecutive composite ultrasound images preferably has a different combination of types of ultrasound transmission and reception in ultrasound images.

An ultrasound image to be combined is preferably shared between the temporally adjacent composite ultrasound images so that a last ultrasound image in one composite ultrasound image and a first ultrasound image in its subsequent composite ultrasound image transmit and receive the ultrasonic waves in the identical directions.

According to the first aspect of the inventive ultrasound diagnostic apparatus configured as described above, the ultrasound transmission and reception are changed depending on the temperature increase in the ultrasound probe upon spatial compounding for combining a plurality of images different in the directions of ultrasound transmission and reception. More specifically, the number of images to be combined by spatial compounding is reduced depending on the temperature increase in the ultrasound probe. Alternatively, the image quality of images be combined by spatial compounding is changed depending on the temperature increase in the ultrasound probe. Alternatively, the depth of images to be combined by spatial compounding is changed depending on the temperature increase in the ultrasound probe. Alternatively, depending on the temperature increase of the ultrasound probe, the number of sound rays is changed beyond the predetermined depth in images to be combined by spatial compounding and the areas having no sound rays are interpolated upon the composition.

Therefore, according to the ultrasound diagnostic apparatus in the first aspect of the invention, the drive frequency, drive time and transmission/reception processing frequency of the piezoelectric unit and the integrated circuits such as AFEs for processing reception signals which are mounted on the ultrasound probe can be reduced depending on the internal temperature of the ultrasound probe. Therefore, when heat is generated within the ultrasound probe, the temperature increase in the integrated circuit and the piezoelectric unit can be suppressed. Heat generation from the ultrasound probe can also be suppressed to minimize the deterioration of the image quality.

Therefore, the ultrasound diagnostic apparatus according to the first aspect of the invention is capable of consistently obtaining high-definition ultrasound images through spatial compounding.

According to the ultrasound diagnostic apparatus in the second aspect of the invention, the frequency of the switching in the directions of ultrasound transmission and reception can be reduced also upon spatial compounding.

Therefore, the ultrasound diagnostic apparatus according to the second aspect of the invention is capable of simplifying the control of ultrasound transmission and reception upon spatial compounding. Accordingly, the burden of the ultrasound probe upon spatial compounding can be reduced, for example, in the ultrasound diagnostic apparatus in which the function of controlling the ultrasound transmission and reception is incorporated in the ultrasound probe.

BRIEF DESCRIPTION OF THE DRAWINGS

FIG. 11 is a conceptual block diagram showing the third embodiment of the ultrasound diagnostic apparatus according to the first aspect of the invention.

FIG. 20 is a conceptual block diagram showing the fourth embodiment of the ultrasound diagnostic apparatus according to the first aspect of the invention.

FIGS. 33A and 33B are conceptual diagrams for illustrating still another example of spatial compounding which is performed in the ultrasound diagnostic apparatus according to the second aspect of the invention.

FIG. 34 is a conceptual diagram for illustrating spatial compounding.

DETAILED DESCRIPTION OF THE INVENTION

Next, the ultrasound diagnostic apparatus of the invention is described in detail by referring to the preferred embodiments shown in the accompanying drawings.

Figure 1:
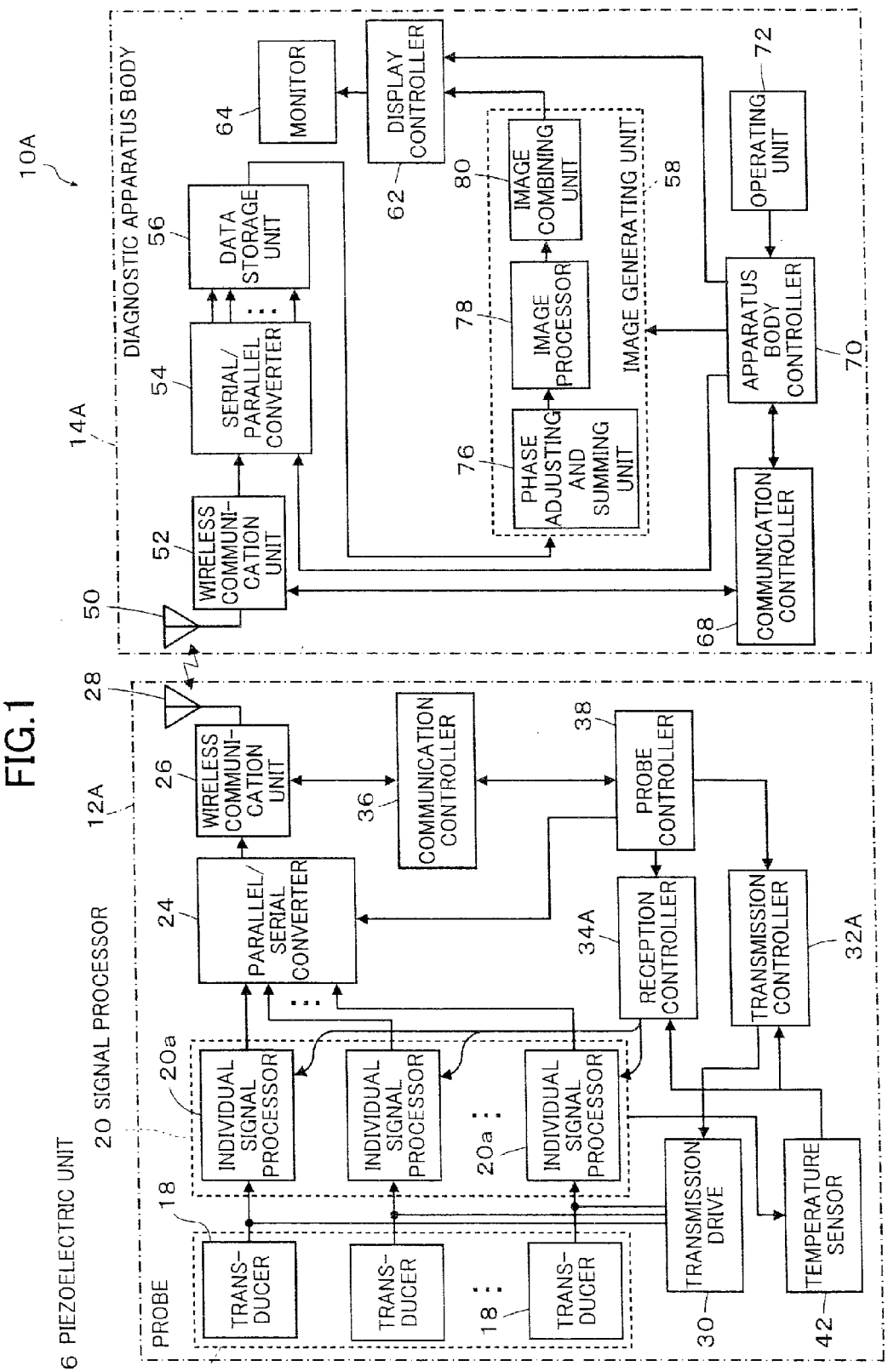
FIG. 1 is a conceptual block diagram showing the first embodiment of the ultrasound diagnostic apparatus according to the first aspect of the invention.

FIG. 1 is a conceptual block diagram showing the first embodiment of the ultrasound diagnostic apparatus according to the first aspect of the invention.

An ultrasound diagnostic apparatus 10A shown in FIG. 1 includes an ultrasound probe 12A and a diagnostic apparatus body 14A. The ultrasound probe 12A is connected to the diagnostic apparatus body 14A by wireless communication.

The ultrasound probe 12A (hereinafter referred to as "probe 12A") transmits ultrasonic waves to a subject, receives ultrasonic echoes generated by reflection of the ultrasound waves on the subject, and outputs reception signals of an ultrasound image in accordance with the received ultrasonic echoes.

In the practice of the invention, various known ultrasound probes can be used for the probe 12A. Therefore, there is no particular limitation on the type of the probe 12A and various types such as convex type, linear type and sector-type can used. The probe may be an external probe or a radial scan type probe for use in an ultrasound endoscope. In addition, the probe 12A may have ultrasound transducers compatible with harmonic imaging for use in receiving second or higher order harmonics from transmitted ultrasonic waves.

The probe 12A includes a piezoelectric unit 16, a signal processor 20, a parallel/serial converter 24, a wireless communication unit 26, an antenna 28, a transmission drive 30, a transmission controller 32A, a reception controller 34A, a communication controller 36, a probe controller 38 and a temperature sensor 42.

The piezoelectric unit 16 is a one-dimensional or two-dimensional array of (ultrasound) transducers 18 transmitting and receiving ultrasonic waves. The piezoelectric unit 16 is connected to the signal processor 20.

The signal processor 20 includes individual signal processors 20a corresponding to the individual transducers 18 of the piezoelectric unit 16. The individual signal processors 20a are connected to the wireless communication unit 26 via the parallel/serial converter 24. The wireless communication unit 26 is further, connected to the antenna 28.

Each of the transducers 18 is connected to the transmission controller 32A via the transmission drive 30. Each of the individual signal processors 20a is connected to the reception controller 34A. The wireless communication unit 26 is connected to the communication controller 36.

The parallel/serial converter 24, the transmission controller 32A, the reception controller 34A, and the communication controller 36 are connected to the probe controller 38.

The probe 12A of the ultrasound diagnostic apparatus 10A is provided with the temperature sensor 42 for measuring the temperature of the signal processor 20. The temperature measurement result obtained with the temperature sensor 42 is supplied to the transmission controller 32A and the reception controller 34A.

The probe 12A includes a built-in battery, which supplies electric power for drive to each component. The battery is not shown in FIG. 1.

The piezoelectric unit 16 is of a known type which includes a one-dimensional or two-dimensional array of the transducers 18 transmitting and receiving ultrasonic waves, and a backing layer, an acoustic matching layer and an acoustic lens laminated thereon.

Each of the transducers 18 is an ultrasound transducer having a piezoelectric body made of, for example, PZT (lead zirconate titanate) or PVDF (polyvinylidene fluoride), and electrodes provided on both ends of the piezoelectric body.

When a pulsed voltage or a continuous-wave voltage is applied to the electrodes of the ultrasound transducer, the piezoelectric body expands and contracts to cause the transducer to generate pulsed or continuous ultrasonic waves. The ultrasonic waves generated by the ultrasound transducers are combined to form ultrasonic beams.

Upon reception of propagating ultrasonic waves, each ultrasound transducer expands and contracts to produce electric signals, which are then outputted as ultrasonic reception signals.

The transducers 18 transmit ultrasonic waves according to drive signals supplied from the transmission drive 30. The transducers 18 receive ultrasonic echoes from the subject, convert the received ultrasonic echoes into electric signals (reception signals) and output the electric signals to the individual signal processors 20a.

The transmission drive 30 includes a digital/analog converter, a low-pass filter, an amplifier and pulsers. The transmission drive 30 supplies each transducer 18 (electrodes of the ultrasound transducer) with a pulsed drive voltage (transmission pulse) to oscillate the ultrasound transducer to thereby transmit ultrasonic waves.

The transmission drive 30 adjusts the delay amounts of drive signals for the respective transducers 18 based on a transmission delay pattern selected by the transmission controller 32A and supplies the transducers 18 with adjusted drive signals so that the ultrasonic waves transmitted from the transducers 18 form ultrasonic beams.

The transducers 18 of the piezoelectric unit 16 are connected to the corresponding individual signal processors 20a of the signal processor 20.

Each individual signal processor 20a has an AFE (analog front end) including an LNA (low-noise amplifier), a VCA (voltage-controlled attenuator), a PGA (programmable gain amplifier), a low-pass filter and an analog/digital converter. Under the control of the reception controller 34A, the individual signal processors 20a convert the reception signals outputted from the corresponding transducers 18 into digital reception signals in the AFE. Then, the individual signal processors 20a subject the digital reception signals generated in the AFE to quadrature detection or quadrature sampling to generate complex baseband signals. In addition, the individual signal processors 20a sample the generated complex baseband signals to generate sample data containing tissue area information and supply the generated sample data to the parallel/serial converter 24.

The parallel/serial converter 24 converts the parallel sample data generated by the individual signal processors 20a in a plurality of channels into serial sample data.

The probe 12A is provided with the temperature sensor 42 for measuring the temperature of the signal processor 20 (reception signal processing circuit portion). The temperature measurement result of the signal processor 20 obtained with the temperature sensor 42 is sent to the transmission controller 32A and the reception controller 34A.

The temperature sensor 42 is not particularly limited but known temperature sensors can be used.

The use of the temperature sensor 42 is not limited to the measurement of the temperature of the signal processor 20 but the internal temperature of the probe 12A may be measured. However, the temperature sensor 42 preferably measures the temperature of the signal processor 20 because heat generation from the signal processor 20 (in particular the AFEs) which processes the reception signals outputted from the transducers 18 is the largest in the probe 12A.

The ultrasound diagnostic apparatus 10A has the function of spatial compounding in which ultrasound images obtained by the ultrasound transmission and reception (transmission and reception of an ultrasonic wave) in mutually different directions are combined to produce a composite ultrasound image. In the illustrated case, for example, three ultrasound images are combined in spatial compounding. Therefore, when spatial compounding is performed, the transmission controller 32A and the reception controller 34A control the drive of the transmission drive 30 and the individual signal processors 20a, respectively, such that three types of ultrasound transmission and reception are performed in three mutually different directions of transmission and reception.

In the ultrasound diagnostic apparatus 10A, the number of images to be combined by spatial compounding is changed depending on the temperature at a predetermined position inside the probe 12A. More specifically, the reception controller 34A and the transmission controller 32A change the number of types of ultrasound transmission and reception depending on the temperature of the signal processor 20 measured with the temperature sensor 42 so as to change the number of ultrasound images to be subjected to spatial compounding. This point will be described in detail later.

The wireless communication unit 26 performs carrier modulation based on the serial sample data to generate transmission signals. The wireless communication unit 26 supplies the antenna 28 with the generated transmission signals so that the antenna 28 transmits radio waves to achieve transmission of the serial sample data.

The modulation methods that may be employed herein include ASK (Amplitude Shift Keying), PSK (Phase Shift Keying), QPSK (Quadrature Phase Shift Keying), and 16QAM (16 Quadrature Amplitude Modulation).

The wireless communication unit 26 uses the antenna 28 to transmit the sample data to the diagnostic apparatus body 14A through wireless communication with the diagnostic apparatus body 14A. In addition, the wireless communication unit 26 receives various control signals from the diagnostic apparatus body 14A and outputs the received control signals to the communication controller 36.

The communication controller 36 controls the wireless communication unit 26 so that the sample data is transmitted at a transmission radio field intensity that is set by the probe controller 38. The communication controller 36 outputs the various control signals received by the wireless communication unit 26 to the probe controller 38.

The probe controller 38 controls various components of the probe 12A according to various control signals transmitted from the diagnostic apparatus body 14A.

As described above, the ultrasound diagnostic apparatus 10A of the invention has the function of producing an image (composite ultrasound image) through spatial compounding.

As is well known, spatial compounding is a technique which involves performing a plurality of types of ultrasound transmission and reception with respect to a subject in mutually different directions of ultrasound transmission and reception (at mutually different scanning angles or in mutually different scanning directions), and combining ultrasound images obtained by the plurality of types of ultrasound transmission and reception to produce a composite ultrasound image. Such spatial compounding enables speckle of ultrasound images to be reduced.

When spatial compounding is performed in the illustrated ultrasound diagnostic apparatus 10A, the probe 12A performs the three types of ultrasound transmission and reception in mutually different directions. As conceptually shown in FIG. 2, the three types of transmission and reception include, for example, transmission and reception for obtaining a main image (ultrasound image covering the whole area for outputting as a composite ultrasound image) which is an ultrasound image having the same region as that of a normal ultrasound image (this case is hereinafter referred to as the "transmission and reception for the main image"), ultrasound transmission and reception in a direction inclined by an angle of $\theta$ with respect to the direction of the ultrasound transmission and reception for the main image (ultrasound transmission and reception in the direction inclined by the angle of $\theta$"), and ultrasound transmission and reception in a direction inclined by an angle of $-\theta$ with respect to the direction of the transmission and reception for the main image.

For convenience, the transmission and reception for the main image is also referred to as the "transmission and reception for an image A", the ultrasound transmission and reception in the direction inclined by the angle of $\theta$ with respect to the direction of the transmission and reception for the image A to as the "transmission and reception for an image B", and the ultrasound transmission and reception in the direction inclined by the angle of $-\theta$ with respect to the direction of the transmission and reception for the image A to as the "transmission and reception for an image C."

When spatial compounding is performed, the transmission controller 32A and the reception controller 34A control the drive of the transmission drive 30 and the individual signal processors 20a, respectively, such that the transmission and reception for the images A, B and C are performed in a predetermined order.

In other words, when spatial compounding is performed in the illustrated example, the three types of ultrasound transmission and reception which make up a frame unit for obtaining a composite ultrasound image are repeatedly performed on a frame basis without changing the frame rate.

Therefore, when spatial compounding is performed, the transmission controller 32A and the reception controller 34A of the probe 12A control the drive of the transmission drive 30 and the individual signal processors 20a, respectively, such that the three types of ultrasound transmission and reception are repeatedly performed.

When spatial compounding is performed, the diagnostic apparatus body 14A (more specifically an image combining unit 80) combines the three ultrasound images including the ultrasound image A (solid line) obtained by the transmission and reception for the image A, the ultrasound image B (broken line) obtained by the transmission and reception for the image B, and the ultrasound image C (chain line) obtained by the transmission and reception for the image C to produce a composite ultrasound image covering the region of the ultrasound image A.

Therefore, in the illustrated example, the number (predetermined number) of ultrasound images to be combined by spatial compounding is three.

In the practice of the invention, the predetermined number of ultrasound images to be combined by spatial compounding is not limited to three but may be two or four or more.

Figure 2:
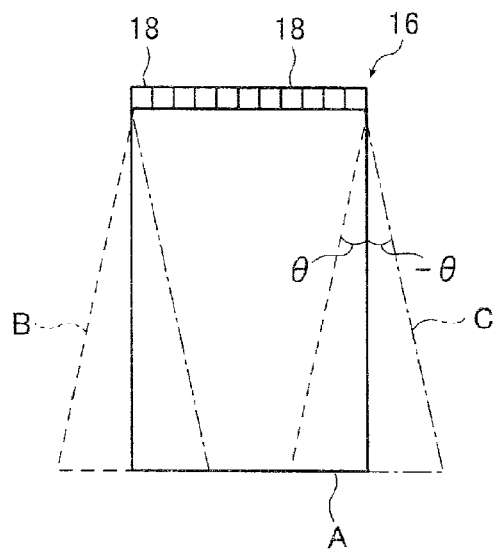
FIG. 2 is a conceptual diagram for illustrating spatial compounding that may be performed in the ultrasound diagnostic apparatus of the invention.

The method of ultrasound transmission and reception in different directions is not limited to the method as conceptually shown in FIG. 2 in which the ultrasound transmission and reception are delayed. Various known methods of ultrasound transmission and reception in different directions can be used, as exemplified by the methods described in JP 2005-58321 A and JP 2003-70786 A.

In addition, the illustrated example refers to the linear type but, as described above, the invention is applicable to probes of various types including convex type and sector type.

As described above, the probe 16 is provided with the temperature sensor 42 for measuring the temperature of the signal processor 20. The temperature measurement result obtained with the temperature sensor 42 is supplied to the transmission controller 32A and the reception controller 34A.

The temperature thresholds including the first temperature T1 [° C.] and the second temperature T2 [° C.] which is higher than T1 are set for the probe 12A (the transmission controller 32A and the reception controller 34A). In the ultrasound diagnostic apparatus 10A, T1 and T2 may be fixed or variable if the relation of T1<T2 is met.

When the temperature measurement result obtained with the temperature sensor 42 is less than T1 upon spatial compounding, the three types of ultrasound transmission and reception (corresponding to three ultrasound images) are all performed in one frame. In other words, the three types of ultrasound transmission and reception are all performed when the probe 12A (signal processor 20) has a steady temperature.

For example, the transmission controller 32A and the reception controller 34A first perform the transmission and reception for the image A for obtaining the ultrasound image A serving as the main image.

Then, the transmission controller 32A and the reception controller 34A perform the transmission and reception for the image B for obtaining the ultrasound image B in the direction inclined by the angle of $\theta$ with respect to the direction for the ultrasound image A.

Then, the transmission controller 32A and the reception controller 34A perform the transmission and reception for the image C for obtaining the ultrasound image C in the direction inclined by the angle of $-\theta$ with respect to the direction for the ultrasound image A.

Figure 3A:
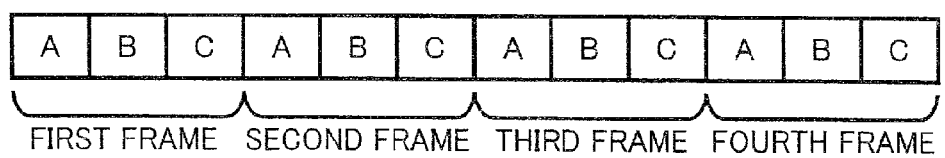
FIGS. 3A, 3B and 3C are conceptual diagrams for illustrating an example of spatial compounding which is performed in the first embodiment of the ultrasound diagnostic apparatus according to the first aspect of the invention.

More specifically, when the temperature measurement result obtained with the temperature sensor 42 is less than T1, as conceptually shown in FIG. 3A, the probe 12A performs, in one frame, all of the three types of ultrasound transmission and reception including the "transmission and reception for the image A", the "transmission and reception for the image B" and the "transmission and reception for the image C". Therefore, the ultrasound transmission and reception are performed for three images. The diagnostic apparatus body 14A combines the three ultrasound images obtained in one frame to produce a composite ultrasound image.

In contrast, when the temperature measurement result obtained with the temperature sensor 42 is equal to or more than T1 but less than T2, the probe 12A reduces, in one frame, the number of times of ultrasound transmission and reception for producing the composite ultrasound image by 1 corresponding to the formation of one image, thus performing the ultrasound transmission and reception for two images not for one image (non-operational periods are provided). In other words, when the temperature is equal to or more than T1 but less than T2, one type of ultrasound transmission and reception is reduced from the three types of ultrasound transmission and reception to perform two types of ultrasound transmission and reception.

For example, when the temperature measurement result is equal to or more than T1 but less than T2, the probe 12A first performs, in one frame, the transmission and reception for the image A, then the transmission and reception for the image B, and does not perform the transmission and reception for the subsequent image C.

Figure 3B:
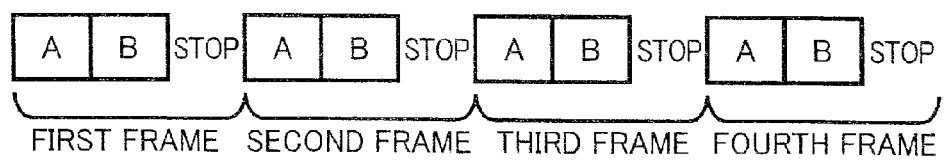

More specifically, when the temperature measurement result obtained with the temperature sensor 42 is equal to or more than T1 but less than T2, as conceptually shown in FIG. 3B, the ultrasound transmission and reception are repeatedly performed on a frame basis according to the process of one frame including the "transmission and reception for the image A", "transmission and reception for the image B" and "non-operation (stop)." The diagnostic apparatus body 14A combines two ultrasound images obtained in one frame to produce a composite ultrasound image.

When the temperature measurement result obtained with the temperature sensor 42 is equal to or more than T2, the probe 12A reduces the number of times of ultrasound transmission and reception for producing the composite ultrasound image by 2 corresponding to the formation of two images, thus performing the ultrasound transmission and reception for one image not for two images (non-operational periods are prolonged). In other words, when the temperature is equal to or more than T2, two types of ultrasound transmission and reception are reduced from the three types of ultrasound transmission and reception to perform only one type of ultrasound transmission and reception.

For example, when the temperature measurement result is equal to or more than T2, the probe 12A first performs, in one frame, the transmission and reception for the image A but does not perform the transmission and reception for the image B and also the transmission and reception for the subsequent image C.

Figure 3C:
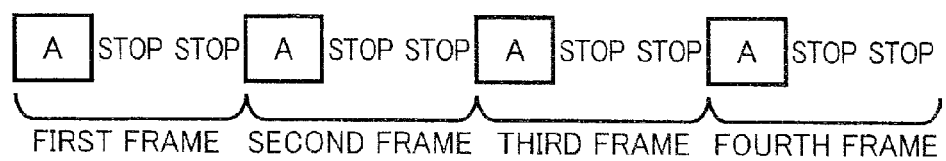

More specifically, when the temperature measurement result obtained with the temperature sensor 42 is equal to or more than T2, as conceptually shown in FIG. 3C, the ultrasound transmission and reception are repeatedly performed on a frame basis according to the process of one frame including the "transmission and reception for the image A", "non-operation" and "non-operation." The diagnostic apparatus body 14A uses one ultrasound image obtained in one frame to produce a composite ultrasound image. In other words, when the temperature measurement result obtained with the temperature sensor 42 is equal to or more than T2, spatial compounding is not performed in the ultrasound diagnostic apparatus 10A.

As is clear from the above description, in cases where the temperature of the probe 12A is increased upon spatial compounding, the ultrasound diagnostic apparatus 10A reduces the drive time of the signal processor 20 and the like without changing the frame rate for producing composite ultrasound images through spatial compounding. In other words, in cases where the temperature of the probe 12A is increased, the drive of the signal processor 20 and other heat generation part stopped depending on the temperature.

Therefore, according to the invention, the internal temperature of the probe 12A can be promptly reduced by stopping the heat generation part such as the signal processor 20 even if the temperature of the probe 12A is increased upon spatial compounding. Even if the temperature of the probe 12A is increased, the image quality deterioration can be minimized by promptly reducing the temperature inside the probe 12A while suppressing the temperature increase therein.

In the example shown in FIGS. 3A to 3C, the order of ultrasound transmission and reception of the images of one frame is the same for all the frames but this is not the sole case of the invention. In other words, the order of ultrasound transmission and reception of the images in each frame may be different. In addition, the order of ultrasound transmission and reception of the images of one frame may be different between cases where the temperature measurement result obtained with the temperature sensor 42 is equal to or more than T1 but less than T2 and cases where the temperature measurement result obtained with the temperature sensor 42 is equal to or more than T2.

Examples of these processes are shown in FIGS. 4A-4C and 5A-5B.

Figure 4A:
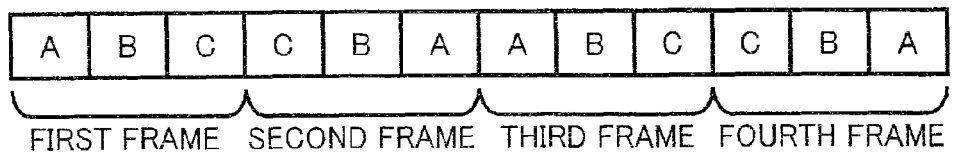
FIGS. 4A, 4B and 4C are conceptual diagrams for illustrating another example of spatial compounding which is performed in the first embodiment of the ultrasound diagnostic apparatus according to the first aspect of the invention.

For example, when the temperature measurement result obtained with the temperature sensor 42 is less than T1, as shown in FIG. 4A, the ultrasound transmission and reception of the first frame, the second frame, the third frame and the like may be performed in the orders of "image A→image B→image C", "image C→image B→image A", "image A→image B→image C" and the like, respectively.

Figure 4B:
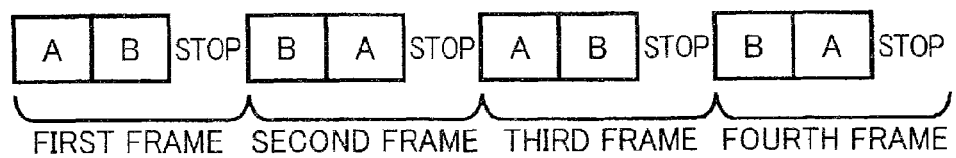

When the temperature measurement result obtained with the temperature sensor 42 is equal to or more than T1 but less than T2 and the ultrasound transmission and reception are not performed for the image C, as shown in FIG. 4B, the ultrasound transmission and reception of the first frame, the second frame, the third frame and the like may be performed in the orders of "image A→image B→non-operation (stop)", "image B→image A→non-operation", "image A→image B→non-operation" and the like, respectively.

That is, in the practice of the invention, the directions of ultrasound transmission and reception in the last ultrasound image in one of two consecutive frames (i.e., two temporally consecutive composite ultrasound images) and the first ultrasound image in the subsequent frame may be the same.

This order of ultrasound transmission and reception enables the ultrasound transmission and reception to be continued in the same directions to facilitate the control of the transmission drive 30 and the individual signal processors 20a.

Figure 4C:
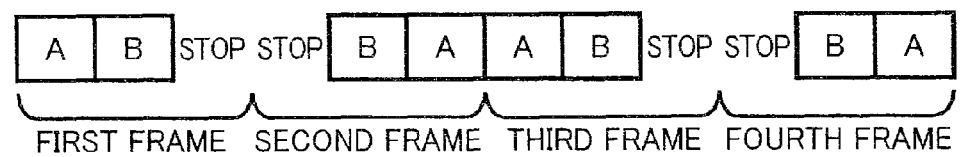

For example, when the temperature measurement result obtained with the temperature sensor 42 is equal to or more than T1 but less than T2 and the ultrasound transmission and reception are not performed for the image C, as shown in FIG. 4C, the non-operational time period may be increased by continuing the non-operational state provided in the last part of one frame up to the first part of the subsequent frame, more specifically by performing the ultrasound transmission and reception of the first frame, the second frame, the third frame and the like in the orders of "image A→image B→non-operation (stop)", "non-operation image B→image A", "image A→image B→non-operation" and the like, respectively.

In the above examples, the number of non-operational states determined by the temperature measurement results is the same in all the frames but this is not the sole case of the invention. That is, the number of non-operational states may be different in the consecutive frames. In other words, in the practice of the invention, in cases where the temperature of the probe 12A is increased, the ultrasound transmission and reception may be stopped anywhere within two consecutive frames.

Figure 5A:
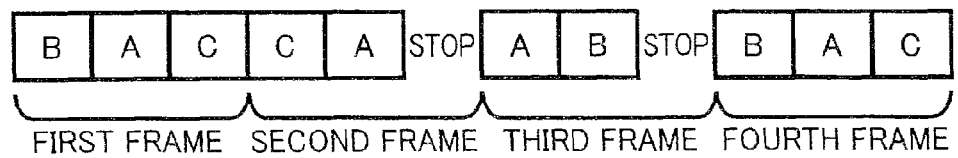
FIGS. 5A and 5B are conceptual diagrams for illustrating yet another example of spatial compounding which is performed in the first embodiment of the ultrasound diagnostic apparatus according to the first aspect of the invention.

For example, when the temperature measurement result obtained with the temperature sensor 42 is equal to or more than T1 but less than T2, as shown in FIG. 5A, the ultrasound transmission and reception of the first frame, the second frame, the third frame, the fourth frame and the like may be performed in the orders of "image B→image A→image C", "image C→image A→non-operation (stop)", "image A→image B→non-operation", "image B→image A→image C" and the like, respectively.

Figure 5B:
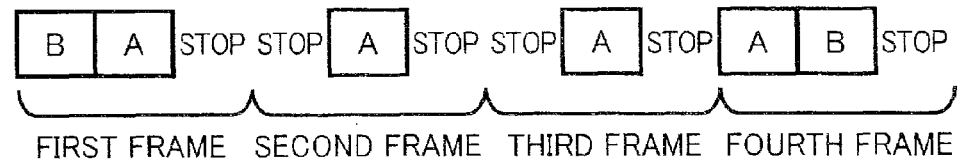

When the temperature measurement result obtained with the temperature sensor 42 is equal to or more than T2, as shown in FIG. 5B, the ultrasound transmission and reception of the first frame, the second frame, the third frame, the fourth frame and the like may be performed in the orders of "image B→image A→non-operation", "non-operation→image A→non-operation", "non-operation→image A→non-operation", "image A→image B→non-operation" and the like, respectively.

In the example shown in FIGS. 5A and 5B, similarly to the example shown in FIGS. 4A to 4C, the directions of ultrasound transmission and reception are the same in the last ultrasound image in one frame and the first ultrasound image in its subsequent frame. However, in the example shown in FIGS. 5A and 5B in which the number of ultrasound images to be combined is different in the consecutive frames, this is not the sole case of the invention. That is, even in the example shown in FIGS. 5A and 5B in which the number of ultrasound images to be combined is different in the consecutive frames, the directions of ultrasound transmission and reception may be different between the last ultrasound image in one frame and the first ultrasound image in its subsequent frame as in the example shown in FIG. 3A.

In the above examples, the transmission and reception for the image B and/or the transmission and reception for the image C are stopped when the temperature inside the probe 12A is increased but this is not the sole case of the invention. That is, the transmission and reception for the image A ma stopped as a result of a temperature increase and a composite ultrasound image in the region of the ultrasound image A be produced from the transmission and reception for the image B and the transmission and reception for the image C.

However, the composite ultrasound image produced in the diagnostic apparatus body 14A is an image having the region of the ultrasound image A serving as the main image. Therefore, it is more advantageous to perform the transmission and reception for the image A serving as the main image (transmission and reception covering the whole area for outputting as a composite ultrasound image) because a proper composite ultrasound image can be consistently obtained. In cases where the ultrasound transmission and reception are performed only for one image because of the temperature increase, the transmission and reception for the image A which is the normal ultrasound transmission and reception is to be performed to output an ultrasound image in a predetermined region.

In addition, in the above examples, since the predetermined number (maximum number of images to be combined) upon spatial compounding is three, two temperature thresholds are provided but this is not the sole case of the invention. For example, in cases where the predetermined number upon spatial compounding is four or more, three or more thresholds may be provided.

Even if the predetermined number is four or more and/or the number of thresholds is three or more, the example shown in FIGS. 4A-4C in which the order of ultrasound transmission and reception of the images is different in consecutive frames and the example shown in FIGS. 5A and 5B in which the number of times of ultrasound transmission and reception performed in consecutive frames is different are of course applicable.

As described above, the reception signals outputted from the probe 12A are supplied to the diagnostic apparatus body 14A by wireless communication.

The diagnostic apparatus body 14A includes an antenna 50, a wireless communication unit 52, a serial/parallel converter 54, a data storage unit 56, an image generating unit 58, a display controller 62, a monitor 64, a communication controller 68, an apparatus body controller 70 and an operating unit 72.

The antenna 50 for use in the transmission to and reception from the antenna 28 of the probe 12A is connected to the wireless communication unit 52. The wireless communication unit 52 is connected to the data storage unit 56 via the serial/parallel converter 54. The data storage unit 56 is connected to the image generating unit 58. The image generating unit 58 is connected to the monitor 64 via the display controller 62.

The wireless communication unit 52 is connected to the communication controller 68. The serial/parallel converter 54, the image generating unit 58, the display controller 62 and the communication controller 68 are connected to the apparatus body controller 70.

The apparatus body controller 70 controls the components in the diagnostic apparatus body 14A. The apparatus body controller 70 is connected to the operating unit 72 to perform various input operations including as to whether or not spatial compounding is to be performed.

The diagnostic apparatus body 14A includes a built-in power supply unit, which supplies electric power for drive to each component. The power supply unit is not shown in FIG. 1.

The diagnostic apparatus body 14A may include a recharging means for recharging a built-in battery of the probe 12A.

The wireless communication unit 52 transmits various control signals to the probe 12A through wireless communication with the probe 12A. The wireless communication unit 52 demodulates the signals received by the antenna 50 to output serial sample data.

The communication controller 68 controls the wireless communication unit 52 so that various control signals are transmitted at a transmission radio field intensity that is set by the apparatus body controller 70.

The serial/parallel converter 54 converts the serial sample data outputted from the wireless communication unit 52 into parallel sample data. The data storage unit 56 is constituted by a memory, a hard disk, or the like and stores at least one frame of sample data converted by the serial/parallel converter 54.

The image generating unit 58 performs reception focusing on sample data for each image read out from the data storage unit 56 to generate image signals representing an ultrasound image. The image generating unit 58 includes a phase adjusting and summing unit 76, an image processor 78 and the image combining unit 80.

The phase adjusting and summing unit 76 selects one reception delay pattern from a plurality of previously stored reception delay patterns according to the reception direction set by the apparatus body controller 70 and, based on the selected reception delay pattern, provides the complex baseband signals represented by the sample data with respective delays and adds them up to perform the reception focusing. This reception focusing yields baseband signals (sound ray signals) where the ultrasonic echoes are well focused.

The image processor 78 generates image signals for an ultrasound image (B-mode image), which is tomographic image information on a tissue inside the subject, according to the sound ray signals generated by the phase adjusting and summing unit 76.

The image processor 78 includes an STC (sensitivity time control) section and a DSC (digital scan converter). The STC section corrects the sound ray signals for the attenuation due to distance according to the depth at which the ultrasonic waves are reflected. The DSC converts the sound ray signals corrected by the SIC into image signals compatible with the common scanning method of television signals (raster conversion) and performs required image processing such as gradation processing to generate ultrasound image signals.

The image combining unit 80 combines the ultrasound images when spatial compounding is performed.

The ultrasound diagnostic apparatus 10A basically combines three ultrasound images when spatial compounding is performed.

In the ultrasound diagnostic apparatus 10A, as described above, the temperature of the reception processor 20 is measured with the temperature sensor 42 and the number of ultrasound images to be combined by spatial compounding is appropriately reduced while increasing the non-operational time period of the reception processor 20 and the like each time the measured temperature exceeds one of the set temperature thresholds.

For example, upon spatial compounding, the probe 12A performs the transmission and reception for the image A, the transmission and reception for the image B and the transmission and reception for the image C as shown in FIG. 3A when the temperature measurement result obtained with the temperature sensor 42 shows that the temperature is less than T1.

When the temperature measured with the temperature sensor 42 is equal to or more than T1 but less than T2, as shown in FIG. 3B, the probe 12A only performs the transmission and reception for the image A and the transmission and reception for the image B (the transmission and reception for the image C are not performed).

When the temperature measured with the temperature sensor 42 is equal to or more than T2, as shown in FIG. 3C, the probe 12A only performs the transmission and reception for the image A (the transmission and reception for the images B and C are not performed).

When spatial compounding is performed in the respective cases, the image combining unit 80 combines three or two ultrasound images for which the ultrasound transmission and reception were performed based on the temperature of the reception processor 20 measured with the temperature sensor 42 and there is no image composition when one ultrasound image is formed.

In the example shown in FIGS. 3A to 3C, when the temperature measured with the temperature sensor 42 is less than T1, the image combining unit 80 combines the ultrasound image A derived from the transmission and reception for the image A, the ultrasound image B derived from the transmission and reception for the image B, and the ultrasound image C derived from the transmission and reception for the image C to generate image signals for a composite ultrasound image.

When the temperature measured with the temperature sensor 42 is equal to or more than T1 but less than T2, the image combining unit 80 combines the ultrasound image A derived from the transmission and reception for the image A and the ultrasound image B derived from the transmission and reception for the image B to generate image signals for a composite ultrasound image.

When the temperature measured with the temperature sensor 42 is equal to or more than T2, the ultrasound image A derived from the transmission and reception for the image A is only supplied and therefore the image combining unit 80 does not perform image composition but directly outputs the image signals for the ultrasound image A as in the production of a normal ultrasound image.

The display controller 62 causes the monitor 64 to display the ultrasound image according to the image signals generated by the image generating unit 58.

The monitor 64 includes a display device such as an LCD, for example, and displays the ultrasound image under the control of the display controller 62.

The operation of the ultrasound diagnostic apparatus 10A shown in FIG. 1 is described below.

In the ultrasound diagnostic apparatus 10A, during the diagnosis, various kinds of information inputted from the operating unit 72 of the diagnostic apparatus body 14A are first sent from the wireless communication unit 52 (antenna 50) of the diagnostic apparatus body 14A to the wireless communication unit 26 (antenna 28) of the probe 12A and then supplied to the probe controller 38. Then, ultrasonic waves are transmitted from the transducers 18 in accordance with the drive voltage supplied from the transmission drive 30 of the probe 12A.

The reception signals outputted from the transducers 18 that have received the ultrasonic echoes generated by reflection of the ultrasonic waves on the subject are supplied to the corresponding individual signal processors 20a to generate sample data.

In the probe 12A, when spatial compounding is performed, the temperature measurement result of the signal processor 20 obtained with the temperature sensor 42 is sent to the transmission controller 32A and the reception controller 34A.

In the ultrasound diagnostic apparatus 10A, the number of ultrasound images to be combined by spatial compounding is appropriately reduced based on the temperature measurement result each time the temperature of the reception processor 20 exceeds one of the set temperature thresholds. Therefore, in the probe 12A, the number of ultrasound images for which the ultrasound transmission and reception are to be performed is appropriately reduced while increasing the non-operational time period of the reception processor 20 and the like based on the temperature measurement result of the signal processor 20 obtained with the temperature sensor 42.

For example, when the temperature measurement result obtained with the temperature sensor 42 is less than T1, the transmission controller 32A and the reception controller 34A control the operations of the transmission drive 30 and the signal processor 20 (each individual signal processor 20a) so that the transmission and reception for the image A, the transmission and reception for the image B and the transmission and reception for the image C are performed as shown in FIG. 3A.

When the temperature measurement result obtained with the temperature sensor 42 is equal to or more than T1 but less than T2, the transmission controller 32A and the reception controller 34A control the operations of the transmission drive 30 and the signal processor 20 so that the transmission and reception for the image A and the transmission and reception for the image B are performed but the transmission and reception for the image C are stopped as shown in FIG. 3B.

When the temperature measured with the temperature sensor 42 is equal to or more than T2, the transmission controller 32A and the reception controller 34A control the operations of the transmission drive 30 and the signal processor 20 so that the transmission and reception for the image A are only performed and the transmission and reception for the image B and the transmission and reception for the image C are stopped as shown in FIG. 3C.

The sample data generated by the individual signal processors 20a are sent to the parallel/serial converter 24, where the sample data is converted into serial data. The serial data is then wirelessly transmitted from the wireless communication unit 26 (antenna 28) to the diagnostic apparatus body 14A.

The sample data received by the antenna 50 of the diagnostic apparatus body 14A is sent to the wireless communication unit 52. The sample data is then sent from the wireless communication unit 52 to the serial/parallel converter 54 and is converted into parallel data. The sample data converted into parallel form is stored in the data storage unit 56.

Further, the sample data for each image is read out from the data storage unit 56 to generate image signals of an ultrasound image in the image generating unit 58. The display controller 62 causes the monitor 64 to display the ultrasound image based on the image signals.

When spatial compounding is performed, the image combining unit 80 of the image generating unit 58 combines the ultrasound images.

In the ultrasound diagnostic apparatus 10A, as described above, the number of ultrasound images to be combined by spatial compounding is appropriately reduced each time the temperature of the reception processor 20 exceeds one of the set temperature thresholds. Based on the temperature of the reception processor 20, the image combining unit 80 combines three or two images or does not perform image composition when one ultrasound image is formed.

More specifically, in the example shown in FIG. 3A to 3C, when the temperature measured with the temperature sensor 42 in the probe 12A is less than T1, the image combining unit 80 combines the ultrasound image A derived from the transmission and reception for the image A, the ultrasound image B derived from the transmission and reception for the image B, and the ultrasound image C derived from the transmission and reception for the image C to generate image signals for a composite ultrasound image, and outputs the image signals to the display controller 62.

When the temperature measured with the temperature sensor 42 in the probe 12A is equal to or more than T1 but less than T2, the image combining unit 80 combines the ultrasound image A derived from the transmission and reception for the image A and the ultrasound image B derived from the transmission and reception for the image B to generate image signals for a composite ultrasound image, and outputs the image signals to the display controller 62.

When the temperature measured with the temperature sensor 42 in the probe 12A is equal to or more than T2, the image combining unit 80 does not perform image composition but directly outputs the image signals of the ultrasound image A to the display controller 62.

Figure 6:
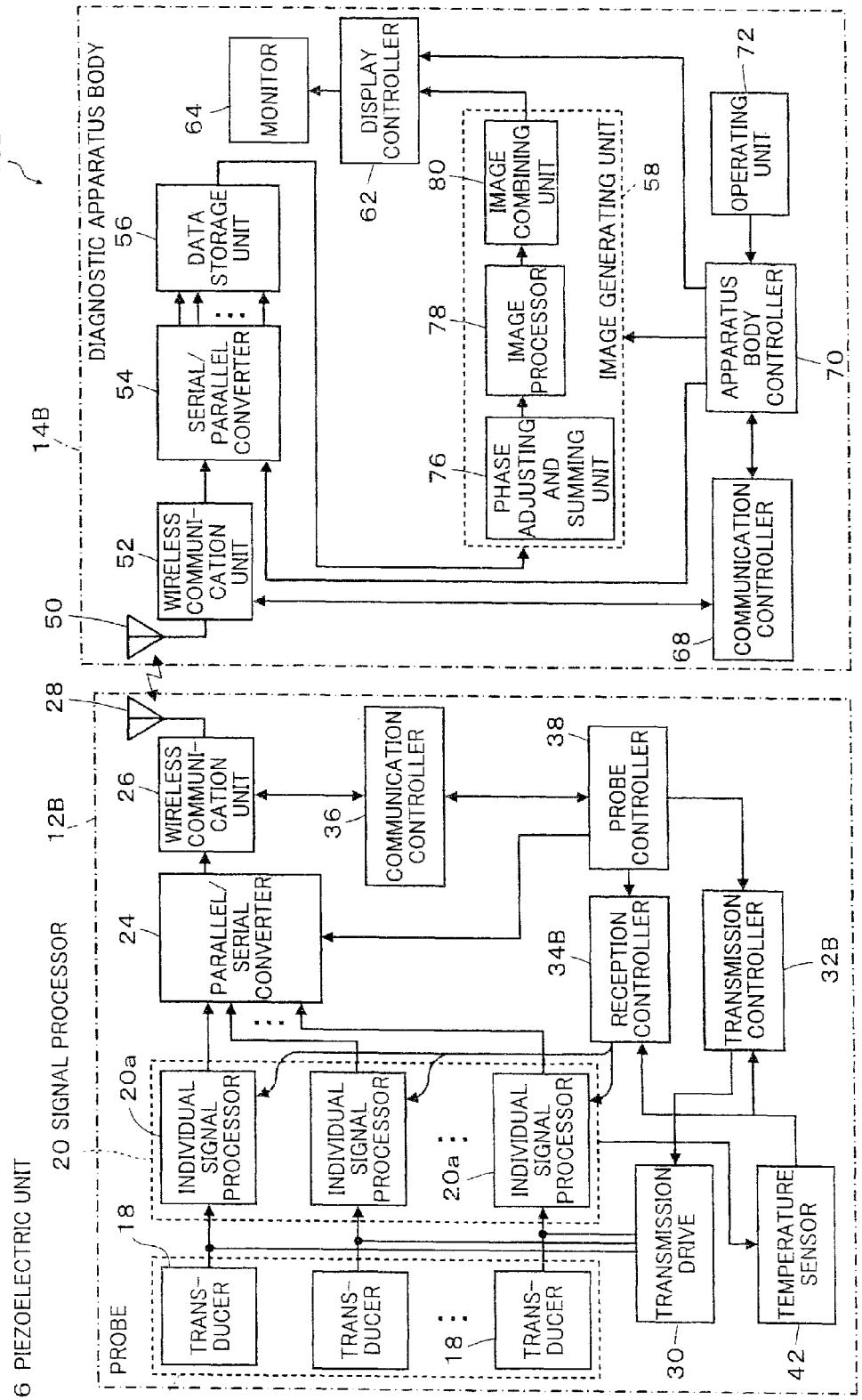
FIG. 6 is a conceptual block diagram showing the second embodiment of the ultrasound diagnostic apparatus according to the first aspect of the invention.

FIG. 6 is a conceptual block diagram showing the second embodiment or the ultrasound diagnostic apparatus according to the first aspect of the invention.

Many components of the ultrasound diagnostic apparatus 10B shown in FIG. 6 are the same as those of the ultrasound diagnostic apparatus 10A shown in FIG. 1. Therefore, like components are denoted by the same reference numerals and the following description mainly focuses on the different features.

As in the first embodiment of the ultrasound diagnostic apparatus 10A, the ultrasound diagnostic apparatus 10B shown in FIG. 6 includes an ultrasound probe 12B (hereinafter referred to as "probe 12B") and a diagnostic apparatus body 14B. As in the above embodiment, the ultrasound probe 12B is connected to the diagnostic apparatus body 14B by wireless communication.

Similarly to the probe 12A in the first embodiment, the probe 12B transmits ultrasonic waves to the subject, receives ultrasonic echoes generated by reflection of the ultrasound waves on the subject, and outputs reception signals of an ultrasound image in accordance with the received ultrasonic echoes.

There is no limitation on the type of the probe 12B and various known ultrasound probes can be used.

As in the probe 12A, the probe 12B also includes a piezoelectric unit 16, a signal processor 20, a parallel/serial converter 24, a wireless communication unit 26, an antenna 28, a transmission drive 30, a transmission controller 32B, a reception controller 34B, a communication controller 36, a probe controller 38 and a temperature sensor 42.

The probe 12B also includes a built-in battery (not shown), which supplies electric power for drive to each component.

The piezoelectric unit 16, the signal processor 20, the parallel/serial converter 24, the wireless communication unit 26, the antenna 28, the transmission drive 30, the communication controller 36, the probe controller 38 and the temperature sensor 42 are basically the same as those of the probe 12A.

More specifically, the piezoelectric unit 16 is a one-dimensional or two-dimensional array of transducers 18 transmitting and receiving ultrasonic waves.

The transmission drive 30 supplies the transducers 18 with a drive voltage so that the transducers transmit ultrasonic waves so as to form ultrasonic beams.

The transducers 18 output the reception signals of the ultrasonic echoes to individual signal processors 20a of the signal processor 20. As described above, each individual signal processor 20a has an AFE, processes the reception signals to generate sample data and supplies the generated sample data the parallel/serial converter 24. The parallel/serial converter 24 converts the parallel sample data into serial sample data.

The ultrasound diagnostic apparatus 10B also has the function of spatial compounding in which ultrasound images obtained by the ultrasound transmission and reception in mutually different directions are combined to produce a composite ultrasound image.

Similarly to the above ultrasound diagnostic apparatus 10A, the ultrasound diagnostic apparatus 10B combines, for example, three ultrasound images upon spatial compounding. Therefore, the transmission controller 32B and the reception controller 34B control the drive of the transmission drive 30 and the individual signal processors 20a, respectively, such that three types of ultrasound transmission and reception are performed in mutually different directions of ultrasound transmission and reception.

The probe 12B has the temperature sensor 42 for measuring the temperature of the signal processor 20. The temperature sensor 42 supplies the temperature measurement result to the transmission controller 32B and the reception controller 34B.

Upon spatial compounding, the transmission controller 32B and the reception controller 34B change the image quality of the ultrasound images for use in producing the composite ultrasound image based on the temperature measurement result. More specifically, based on the temperature of the signal processor 20 measured with the temperature sensor 42, the transmission controller 32B and the reception controller 34B control the drive of the transmission drive 30 and the individual signal processors 20a, respectively so as to change the number of sound rays and/or the number of available channels in the ultrasound transmission and reception for the predetermined ultrasound images to be subjected to spatial compounding.

This point will be described in detail later.

The wireless communication unit 26 generates transmission signals from the serial sample data and transmits the serial sample data to the diagnostic apparatus body 14B via the antenna 28.

The wireless communication unit 26 receives various control signals from the diagnostic apparatus body 14B and outputs the received control signals to the communication controller 36.

The communication controller 36 controls the wireless communication unit 26. The communication controller 36 outputs the various control signals received by the wireless communication unit 26 to the probe controller 38.

The probe controller 38 controls various components of the probe 12B according to various control signals transmitted from the diagnostic apparatus body 14B.

As described above, the ultrasound diagnostic apparatus 10B has the function of producing an image (composite ultrasound image) through spatial compounding.

As in the first embodiment of the ultrasound diagnostic apparatus 10A shown in FIG. 1, the ultrasound diagnostic apparatus 10B also performs, for example, the three types of ultrasound transmission and reception in mutually different directions upon spatial compounding as conceptually shown in FIG. 2. More specifically, upon spatial compounding, the probe 12B performs the three types of ultrasound transmission and reception, including the "transmission and reception for the image A" as the ultrasound transmission and reception for obtaining the main image (image including the whole area of the composite ultrasound image formed by spatial compounding), the "transmission and reception for the image 3" in a direction inclined by an angle of θ with respect to the direction of the transmission and reception for the image A, and the "transmission and reception for the image C" in a direction inclined by an angle of −θ with respect to the direction of the transmission and reception for the image A.

Figure 7A:
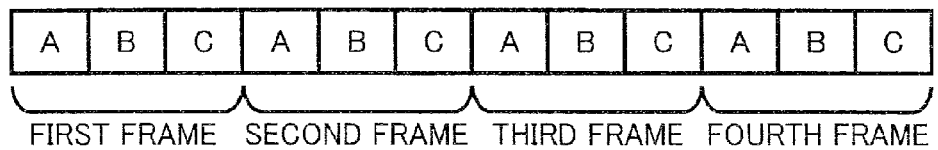
FIGS. 7A, 7B and 7C are conceptual diagrams for illustrating an example of spatial compounding which is performed in the second embodiment of the ultrasound diagnostic apparatus according to the first aspect of the invention.
Figure 7B:
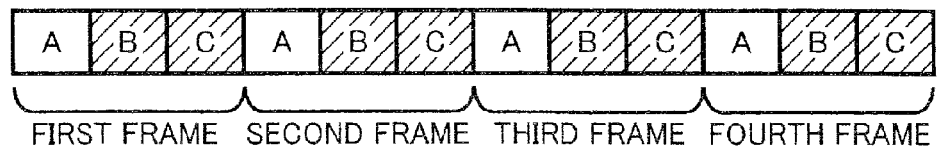
Figure 7C:
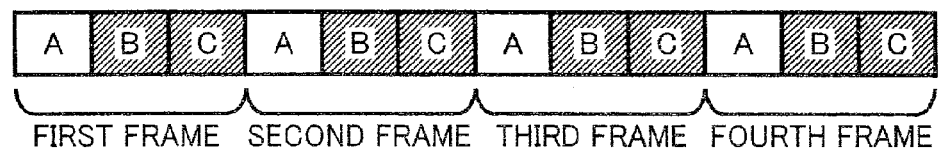

Also in this embodiment, when spatial compounding is performed, the probe 12B repeatedly performs the three types of ultrasound transmission and reception which make up a frame unit without changing the frame rate (see FIGS. 7A to 7C).

When spatial compounding is performed, the transmission controller 32B and the reception controller 34B of the probe 12B control the drive of the transmission drive 30 and the individual signal processors 20a, respectively, such that the three types of ultrasound transmission and reception are repeatedly performed.

On the other hand, when spatial compounding is performed, the diagnostic apparatus body 14B (more specifically an image combining unit 80) combines the three ultrasound images including the ultrasound image A (solid line) as the main image obtained by the transmission and reception for the image A, the ultrasound image B (broken line) obtained by the transmission and reception for the image B, and the ultrasound image C (chain line) obtained by the transmission and reception for the image C to produce a composite ultrasound image covering the region of the ultrasound image A.

Therefore, the number (predetermined number) of ultrasound images to be combined by spatial compounding in the ultrasound diagnostic apparatus 10B is three. However, the predetermined number may be two or four or more as in the above embodiment.

In addition, various known methods can be used to transmit and receive ultrasonic waves in different directions as in the above embodiment.

As described above, the probe 12B is provided with the temperature sensor 42 for measuring the temperature of the signal processor 20. The temperature measurement result obtained with the temperature sensor 42 is supplied to the transmission controller 32B and the reception controller 34B.

The temperature thresholds including the first temperature T3 [° C.] and the second temperature T4 [° C.] which is higher than T3 are set for the probe 12B (transmission controller 32B and the reception controller 34B). In the ultrasound diagnostic apparatus 10B, 13 and T4 may be fixed or variable if the relation of T3<T4 is met.

As described above, the ultrasound diagnostic apparatus 10B changes the conditions of ultrasound transmission and reception for obtaining ultrasound images to be subjected to spatial compounding based on the temperature measurement result obtained with the temperature sensor 42.

In the illustrated embodiment, three conditions of ultrasound transmission and reception under which the image quality of the resulting ultrasound images is different are set in the probe 12B for the ultrasound transmission and reception upon spatial compounding.

The first is the "transmission and reception at the normal image quality level" which are those corresponding to ultrasound images of predetermined image quality to be combined by spatial compounding. The second is the "transmission and reception at the low image quality level" which are those corresponding to ultrasound images of the lowest image quality to be combined by spatial compounding. The third is the "transmission and reception at the medium image quality level" which are those corresponding to ultrasound images having image quality between that in the transmission and reception at the normal image quality level and that in the transmission and reception at the low image quality level.

In the illustrated embodiment, the image quality is adjusted by the number of available channels and/or the number of sound rays (number of scanning lines). The number of available channels (number of simultaneously available channels) is the number of the transducers used in the ultrasound transmission and reception.

More specifically, the transmission and reception at the normal image quality level are performed by setting the number of available channels and the number of sound rays to predetermined numbers. The transmission and reception at the medium image quality level are performed by reducing the number of available channels and/or the number of sound rays from those in the transmission and reception at the normal image quality level. The transmission and reception at the low image quality level are performed by reducing the number of available channels and/or the number of sound rays from those in the transmission and reception at the medium image quality level.

In the illustrated embodiment, in the transmission and reception at the normal image quality level, the number of sound rays and the number of available channels are, for example, 256 and 64, respectively. In the transmission and reception at the medium image quality level, the number of sound rays and the number of available channels are, for example, 128 and 48, respectively. In the transmission and reception at the low image quality level, the number of sound rays and the number of available channels are, for example, 96 and 32, respectively.

In this embodiment, the transmission and reception at the normal image quality level, the transmission and reception at the medium image quality level and the transmission and reception at the low image quality level use different numbers of sound rays and available channels, respectively, but this is not the sole case of the invention.

For example, the transmission and reception at the normal image quality level, the transmission and reception at the medium image quality level and the transmission and reception at the low image quality level may be performed by only changing the number of sound rays or the number of available channels. Each type of ultrasound transmission and reception may have different parameters. For example, the number of sound rays may only be different between the transmission and reception at the normal image quality level and the transmission and reception at the medium image quality level, or the number of sound rays and the number of available channels may be different between the transmission and reception at the medium image quality level and the transmission and reception at the low image quality level.

As described above, upon spatial compounding, the illustrated ultrasound diagnostic apparatus 10B performs the three types of ultrasound transmission and reception for three images in mutually different directions of ultrasound transmission and reception as conceptually shown in FIGS. 2 and 7A to 7C. In the ultrasound diagnostic apparatus 10B, the three types of ultrasound transmission and reception which make up a frame unit for obtaining a composite ultrasound image are repeatedly performed on a frame basis.

For example, as shown in FIGS. 7A to 7C, the transmission controller 32B and the reception controller 34B first perform the transmission and reception for the image A for obtaining the ultrasound image A as the main image.

Then, the transmission controller 32B and the reception controller 34B perform the transmission and reception for the image B for obtaining the ultrasound image B in the direction inclined by the angle of θ with respect to the direction for the ultrasound image A.

Then, the transmission controller 32B and the reception controller 34B perform the transmission and reception for the image C for obtaining the ultrasound image C in the direction inclined by the angle of −θ with respect to the direction for the ultrasound image A.

In FIGS. 7A to 7C, areas each having a black letter on a white background correspond to the transmission and reception at the normal image quality level. Coarsely hatched (shaded) areas correspond to the transmission and reception at the medium image quality level. Densely hatched areas correspond to the transmission and reception at the low image quality level.

When spatial compounding is performed, the transmission controller 32B and the reception controller 34B of the probe 12B in the ultrasound diagnostic apparatus 10B control, as described below, the drive of the transmission drive 30 and the individual signal processors 20a based on the temperature measurement result obtained with the temperature sensor 42, respectively.

That is, when the temperature measurement result obtained with the temperature sensor 42 is less than T3, the transmission controller 32B and the reception controller 34B control the drive of the transmission drive 30 and the individual signal processors 20a, respectively, so that the transmission and reception for the images A, B and C are all performed in one frame at the normal image quality level as shown in FIG. 7A.

The case in which the temperature measurement result obtained with the temperature sensor 42 is less than T3 refers to the case in which the probe 12B (signal processor 20) has a steady temperature.

When the temperature measurement result obtained with the temperature sensor 42 is equal to or more than T3 but less than T4, the transmission controller 32B and the reception controller 34B control the drive of the transmission drive 30 and the individual signal processors 20a, respectively, so that, in one frame, the transmission and reception for the image A are performed at the normal image quality level and the transmission and reception for the images B and C are performed at the medium image quality level as shown in FIG. 7B.

In addition, when the temperature measurement result obtained with the temperature sensor 42 is equal to or more than T4, the transmission controller 32B and the reception controller 34B control the drive of the transmission drive 30 and the individual signal processors 20a, respectively, so that, in each frame, the transmission and reception for the image A are performed at the normal image quality level and the transmission and reception for the images B and C are performed at the low image quality level as shown in FIG. 7C.

As is clear from the above description, in cases where the temperature of the probe 12B is increased upon spatial compounding, the ultrasound diagnostic apparatus 10B reduces the number of sound rays and/or the number of available channels in the ultrasound transmission and reception for obtaining ultrasound images to be combined into a composite ultrasound image, thereby lowering the image quality of the ultrasound images. More specifically, in the ultrasound diagnostic apparatus 10B of the invention, when the temperature of the probe 12B is increased, the number of times the heat generation areas such as the individual signal processors 20a are driven or the number of times the reception signals are processed in the signal processor 20 or the like is reduced depending on the temperature.

Therefore, according to the invention, the internal temperature of the probe 12B can be promptly reduced by stopping the heat generation areas such as the signal processor 20 even if the temperature of the probe 12B is increased during spatial compounding. Even if the temperature of the probe 12B is increased, the image quality deterioration can be minimized by promptly reducing the temperature inside the probe 12B while suppressing the temperature increase therein.

In the example shown in FIGS. 7B and 7C, when the temperature measurement result obtained with the temperature sensor 42 is equal to or more than T3 but less than T4 or is equal to or more than T4, the ultrasound transmission and reception are performed under the same condition for the images for which the condition of ultrasound transmission and reception is to be changed from the transmission and reception at the normal image quality level. However, this is not the sole case of the invention.

In other words, the transmission and reception at the medium image quality level and the transmission and reception at the low image quality level may be performed in one frame, or the transmission and reception at the normal image quality level, the transmission and reception at the medium image quality level and the transmission and reception at the low image quality level may be performed in one frame.

Figure 8A:
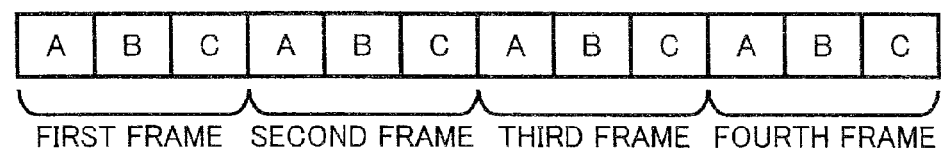
FIGS. 8A, 8B and 8C are conceptual diagrams for illustrating another example of spatial compounding which is performed in the second embodiment of the ultrasound diagnostic apparatus according to the first aspect of the invention.
Figure 8B:
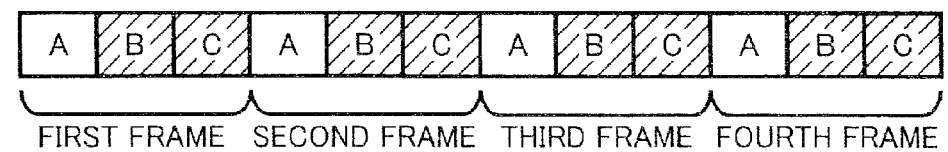
Figure 8C:
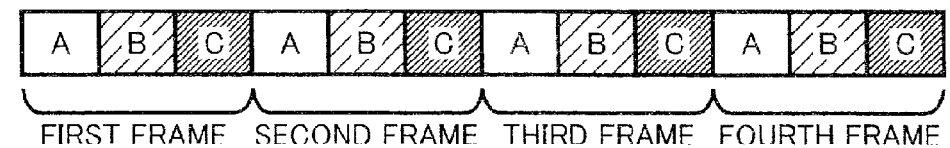

An example of the ultrasound transmission and reception is conceptually shown in FIGS. 8A to 8C.

In this example, as in FIG. 7A, when the temperature measurement result obtained with the temperature sensor 42 is less than T3, the transmission and reception for the images A, B and C are all performed at the normal image quality level as shown in FIG. 8A. As in FIG. 7B, when the temperature measurement result obtained with the temperature sensor 42 is equal to or more than T3 but less than T4, the transmission and reception for the image A are performed at the normal image quality level, whereas those for the images B and C are performed t the medium image quality level as shown in FIG. 8B.

In contrast, in this example, when the temperature measurement result obtained with the temperature sensor 42 is equal to or more than T4, the transmission and reception for the image A are performed at the normal image quality level, those for the image B at the medium image quality level and those for the image C at the low image quality level as shown in FIG. 8C. Alternatively, the transmission and reception for the image A may be performed at the normal image quality level, those for the image B at the low image quality level and those for the image C at the medium image quality level.

Compared to the example shown in FIGS. 7A to 7C, this method reduces the effect of preventing heat generation but is advantageous in terms of the image quality of the composite ultrasound images.

In the above example, when the temperature in the probe 12B is increased, the condition of ultrasound transmission and reception is changed from the transmission and reception at the normal image quality level in the transmission and reception for the image B and/or those for the image C but this is not the sole case of the invention. That is, the transmission and reception for the image A may be performed by changing from the transmission and reception at the normal image quality level to those at the medium or low image quality level depending on the temperature increase.

However, the ultrasound image A is the main image. In other words, the composite ultrasound image produced in the diagnostic apparatus body 14B through spatial compounding is the image having the region of the ultrasound image A (transmission and reception for the image A). Therefore, when the transmission and reception at the normal image quality level are included in one frame, it is more advantageous to perform the transmission and reception for the image A serving as the main image at the normal image quality level because a proper composite ultrasound image can be consistently obtained.

In the above example, the transmission and reception for the image A are performed at the normal image quality level at any temperature but this is not the sole case of the invention. That is, the transmission and reception for the image A may be performed at the medium or low image quality level based on the temperature measurement result obtained with the temperature sensor 42.

Figure 9A:
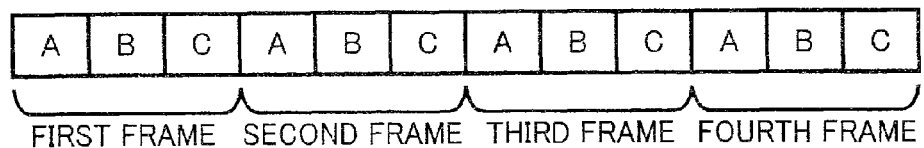
FIGS. 9A, 9B and 9C are conceptual diagrams for illustrating yet another example of spatial compounding which is performed in the second embodiment of the ultrasound diagnostic apparatus according to the first aspect of the invention.
Figure 9B:
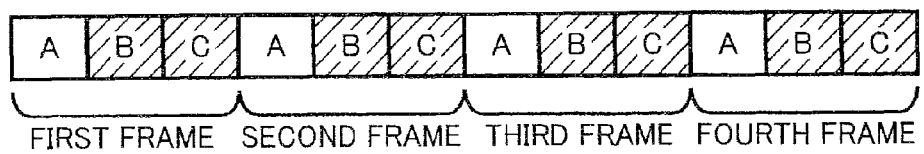
Figure 9C:
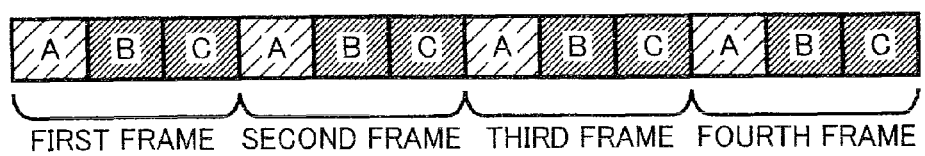

An example of the ultrasound transmission and reception is conceptually shown in FIGS. 9A to 9C.

In this example, as in FIG. 7A, when the temperature measurement result obtained with the temperature sensor 42 is less than T3, the transmission and reception for the images A, B and C are all performed at the normal image quality level as shown in FIG. 9A. As in FIG. 7B, when the temperature measurement result obtained with the temperature sensor 42 is equal to or more than T3 but less than T4, the transmission and reception for the image A are performed at the normal image quality level, whereas those for the images B and C are performed at the medium image quality level as shown in FIG. 9B.

In contrast, in this example, when the temperature measurement result obtained with the temperature sensor 42 is equal to or more than T4, the transmission and reception for the image A are performed at the medium image quality level, whereas those for the images B and C are performed at the low image quality level as shown in FIG. 9C.

Compared to the examples shown in FIGS. 7A-7C and 8A-8C, this method is disadvantageous terms of the image quality but enhances the effect of preventing heat generation.

In this example, when the temperature measurement result obtained with the temperature sensor 42 is equal to or more than T3, the ultrasound transmission and reception for the two images are performed by changing from the transmission and reception at the normal image quality level to another. However, this is not the sole case of the invention.

The condition of ultrasound transmission and reception for only one image or three or more images may be changed from the transmission and reception at the normal image quality level based on the temperature measurement result obtained with the temperature sensor 42.

Considering the purpose that the temperature increase within the probe 12B is suppressed while minimizing the image quality deterioration due to the temperature increase, when the temperature exceeds one of the thresholds, the ultrasound transmission and reception for two or more images are preferably performed by changing the condition of ultrasound transmission and reception from the transmission and reception at the normal image quality level depending on the temperature. In addition, in order to suppress the temperature increase while preventing the image quality deterioration, when the temperature exceeds one of the thresholds, the transmission and reception for all images except the image A (main image) are preferably performed by changing the condition of ultrasound transmission and reception from the transmission and reception at the normal image quality level depending on the temperature.

In addition, in the above examples, since the predetermined number upon spatial compounding is three, two temperature thresholds are provided. However, this is not the sole case of the invention and in cases where the predetermined number is four or more, three or more thresholds may be provided.

The number of conditions of ultrasound transmission and reception determined by the temperature is not limited to three. For example, two conditions including the transmission and reception at the normal image quality level and the transmission and reception at the low image quality level may be applied. Alternatively, four or more conditions including a plurality of types of transmission and reception at the medium image quality level in addition to the transmission and reception at the normal image quality level and the transmission and reception at the low image quality level may be applied.

In the examples shown in FIGS. 7A to 9C, the order of ultrasound transmission and reception in one frame is the same for all the frames but this is not the sole case of the invention and the order of ultrasound transmission and reception of the images may be different frame by frame.

Figure 10A:
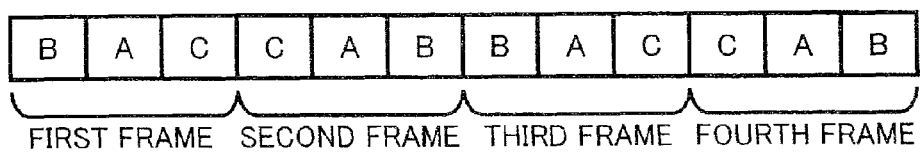
FIGS. 10A, 10B and 10C are conceptual diagrams for illustrating still another example of spatial compounding which is performed in the second embodiment of the ultrasound diagnostic apparatus according to the first aspect of the invention.
Figure 10B:
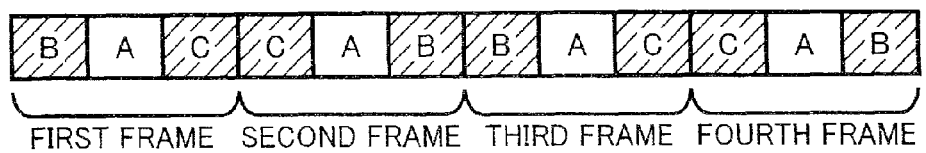
Figure 10C:
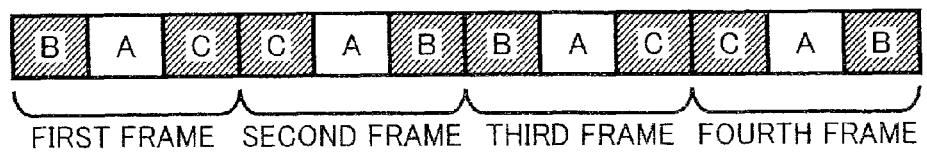

For example, as shown in FIGS. 10A to 10C, the ultrasound transmission and reception of the first frame, the second frame, the third frame, the fourth frame and the like may be performed in the orders of "image B→image A→image C", "image C→image A→image B", "image B→image A→image C", "image C→image A→" image B and the like, respectively.

That is, in the second embodiment of the ultrasound diagnostic apparatus 10B, as in the first embodiment, the directions of ultrasound transmission and reception in the last ultrasound image in the earlier one of two consecutive frames (i.e., two temporally consecutive composite ultrasound images) and the first ultrasound image in the subsequent frame may be the same.

This order of ultrasound transmission and reception enables the ultrasound transmission and reception to be continued in the same directions to facilitate the control of the transmission drive 30 and the individual signal processors 20a.

As described above, the reception signals outputted from the probe 12B are supplied to the diagnostic apparatus body 14B by wireless communication.

Similarly to the first embodiment of the diagnostic apparatus body 14A shown in FIG. 1, the diagnostic apparatus body 14B includes an antenna 50, a wireless communication unit 52, a serial/parallel converter 54, a data storage unit 56, an image generating unit 58, a display controller 62, a monitor 64, a communication controller 68, an apparatus body controller 70 and an operating unit 72.

As in the above embodiment, the diagnostic apparatus body 14B includes a built-in power supply unit (not shown), which supplies electric power for drive to each component.

The antenna 50, the wireless communication unit 52, the serial/parallel converter 54, the data storage unit 56, the image generating unit 58, the display controller 62, the monitor 64, the communication controller 68 and the apparatus body controller 70 are basically the same as those in the diagnostic apparatus body 10A shown in FIG. 1.

More specifically, the wireless communication unit 52 performs wireless communication with the probe 12B via the antenna 50 to transmit control signals to the probe 12B and receive signals sent from the probe 12B. The wireless communication unit 52 demodulates the received signals and outputs them to the serial/parallel converter 54 as serial sample data.

The communication controller 68 controls the wireless communication unit 52 so that various control signals are transmitted according to the settings made by the apparatus body controller 70.

The serial/parallel converter 54 converts the serial sample data into parallel sample data. The data storage unit 56 stores at least one frame of sample data converted by the serial/parallel converter 54.

The image generating unit 58 (phase adjusting and summing unit 76, image processor 78 and image combining unit 80) performs reception focusing on sample data for each image read out from the data storage unit 56 to generate image signals representing an ultrasound image.

As described above, when spatial compounding is performed in the ultrasound diagnostic apparatus 10B, the probe 12B performs, for example, the ultrasound transmission and reception for three images, that is, the transmission and reception for the images A, B and C.

When spatial compounding is performed, the image combining unit 80 of the image generating unit 58 accordingly combines the ultrasound image A derived from the transmission and reception for the image A, the ultrasound image B derived from the transmission and reception for the image B, and the ultrasound image C derived from the transmission and reception for the image C to generate image signals for a composite ultrasound image.

As described above, when spatial compounding is performed in the ultrasound diagnostic apparatus 10B, the probe 12B changes the condition of ultrasound transmission and reception for obtaining ultrasound images to be combined based on the temperature measurement result obtained with the temperature sensor 42.

Therefore, the ultrasound images to be combined in the image combining unit 80 have accordingly changed image quality such as normal, medium or low image quality.

The display controller 62 causes the monitor 64 to display the ultrasound image according to the image signals generated by the image generating unit 58.

Under the control of the display controller 62, the monitor 64 displays the ultrasound image.

The apparatus body controller 70 controls the components in the diagnostic apparatus body 14B. The apparatus body controller 70 is connected to the operating unit 72 to perform various input operations including as to whether or not spatial compounding is to be performed.

The operation of the ultrasound diagnostic apparatus 10B shown in FIG. 6 is described below.

Similarly to the ultrasound diagnostic apparatus 10A, during the diagnosis, various kinds of information inputted to the operating unit 72 are first sent to the probe 12B by wireless communication and then supplied to the probe controller 38 also in the ultrasound diagnostic apparatus 10B.

Then, ultrasonic waves are transmitted from the transducers 18 in accordance with the drive voltage supplied from the transmission drive 30 of the probe 12B.

The reception signals outputted from the transducers 18 that have received the ultrasonic echoes generated by reflection of the ultrasonic waves on the subject are supplied to the corresponding individual signal processors 20a to generate sample data.

In the probe 12B, when spatial compounding is performed, the temperature measurement result of the signal processor 20 obtained with the temperature sensor 42 is sent to the transmission controller 32B and the reception controller 34B.

As described above, when spatial compounding is performed in the ultrasound diagnostic apparatus 10B, the probe 12B adjusts the image quality of the ultrasound images to be combined based on the temperature measurement result of the reception processor 20 obtained with the temperature sensor 42. More specifically, when spatial compounding is performed, the probe 12B selects the condition of ultrasound transmission and reception for obtaining ultrasound images to be combined from among the transmission and reception at the normal image quality level, transmission and reception at the medium image quality level and transmission and reception at the low image quality level based on the temperature measurement result of the reception processor 20 such that the image quality of the composite ultrasound image is lowered each time the temperature of the reception processor 20 exceeds one of the temperature thresholds.

For example, when the temperature measured with the temperature sensor 42 is less than T3, the transmission controller 32B and the reception controller 34B control the operations of the transmission drive 30 and the signal processor 20 (each individual signal processor 20a) so that the transmission and reception for the images A, B and C are all performed at the normal image quality level as shown in FIG. 7A.

When the temperature measured with the temperature sensor 42 is equal to or more than T3 but less than T4, the transmission controller 32B and the reception controller 34B control the operations of the transmission drive 30 and the signal processor 20 so that the transmission and reception for the image A are performed at the normal image quality level and the transmission and reception for the images B and C are performed at the medium image quality level as shown in FIG. 7B.

When the temperature measured with the temperature sensor 42 is equal to or more than T4, the transmission controller 32B and the reception controller 34B control the operations of the transmission drive 30 and the signal processor 20 so that the transmission and reception for the image A are performed at the normal image quality level and the transmission and reception for the images B and C are performed at the low image quality level as shown in FIG. 7C.

The sample data generated by the individual signal processors 20a are sent to the parallel/serial converter 24, where the sample data is converted into serial data. The serial data is then wirelessly transmitted from the wireless communication unit 26 (antenna 28) to the diagnostic apparatus body 14B.

The sample data received by the wireless communication unit 52 of the diagnostic apparatus body 14B is converted into parallel data in the serial/parallel converter 54 and stored in the data storage unit 56.

Further, the sample data for each image is read out from the data storage unit 56 to generate image signals of an ultrasound image in the image generating unit 58. The display controller 62 causes the monitor 64 to display the ultrasound image based on the image signals.

When spatial compounding is performed, the image combining unit 80 of the image generating unit 58 combines the ultrasound images.

More specifically, as described above, when spatial compounding is performed, the image combining unit 80 combines the ultrasound image A derived from the transmission and reception for the image A, the ultrasound image B derived from the transmission and reception for the image B, and the ultrasound image C derived from the transmission and reception for the image C to generate image signals for a composite ultrasound image, and outputs the image signals to the display controller 62.

As described above, when spatial compounding is performed in the ultrasound diagnostic apparatus 10B, the probe 12B selects the condition of ultrasound transmission and reception from among the transmission and reception at the normal image quality level, transmission and reception at the medium image quality level and transmission and reception at the low image quality level based on the temperature measurement result of the reception processor 20 such that the image quality of the composite ultrasound image is lowered each time the temperature of the reception processor 20 exceeds one of the temperature thresholds.

Therefore, the ultrasound images to be combined in the image combining unit 80 are also various combinations of normal image quality images, medium image quality images and low image quality images based on the temperature measurement results.

For example, in the above-described ultrasound transmission and reception shown in FIGS. 7A to 7C, when the temperature measured with the temperature sensor 42 in the probe 12B is less than T3, the ultrasound images A, B and C all have normal image quality as obtained by the transmission and reception at the normal image quality level.

When the temperature measured with the temperature sensor 42 in the probe 12B is equal to or more than T3 but less than T4, the ultrasound image A has normal image quality as obtained by the transmission and reception at the normal image quality level, and the ultrasound images B and C have medium image quality as obtained by the transmission and reception at the medium image quality level.

When the temperature measured with the temperature sensor 42 in the probe 12B is equal to or more than T4, the ultrasound image A has normal image quality as obtained by the transmission and reception at the normal image quality level, and the ultrasound images B and C have low image quality as obtained by the transmission and reception at the low image quality level.

FIG. 11 is a conceptual block diagram showing the third embodiment of the ultrasound diagnostic apparatus according to the first aspect of the invention.

Many components of the ultrasound diagnostic apparatus 10C shown in FIG. 11 are the same as those of the ultrasound diagnostic apparatus 10A shown in FIG. 1. Therefore, like components are denoted by the same reference numerals and the following description mainly focuses on the different features.

As in the first embodiment of the ultrasound diagnostic apparatus 10A, the ultrasound diagnostic apparatus 10C shown in FIG. 11 includes an ultrasound probe 12C (hereinafter referred to as "probe 12C") and a diagnostic apparatus body 14C. As in the above embodiment, the ultrasound probe 12C is connected to the diagnostic apparatus body 14C by wireless communication.

Similarly to the probe 12A in the first embodiment, the probe 12C transmits ultrasonic waves to the subject, receives ultrasonic echoes generated by reflection of the ultrasound waves on the subject, and outputs reception signals of an ultrasound image in accordance with the received ultrasonic echoes.

There is no limitation on the type of the probe 12C and various known ultrasound probes can be used.

As in the probe 12A, the probe 12C also includes a piezoelectric unit 16, a signal processor 20, a parallel/serial converter 24, a wireless communication unit 26, an antenna 28, a transmission drive 30, a transmission controller 32C, a reception controller 34C, a communication controller 36, a probe controller 38 and a temperature sensor 42.

The probe 12C also includes a built-in battery (not shown), which supplies electric power for drive to each component.

The piezoelectric unit 16, the signal processor 20, the parallel/serial converter 24, the wireless communication unit 26, the antenna 28, the transmission drive 30, the communication controller 36, the probe controller 38 and the temperature sensor 42 are basically the same as those of the probe 12A.

More specifically, the piezoelectric unit 16 is a one-dimensional or two-dimensional array of transducers 18 transmitting and receiving ultrasonic waves.

The transmission drive 30 supplies the transducers 18 with a drive voltage so that the transducers transmit ultrasonic waves so as to form ultrasonic beams.

The transducers 18 output the reception signals of the ultrasonic echoes to individual signal processors 20a of the signal processor 20. As described above, the individual signal processors 20a each include an AFT, process the reception signals to generate sample data and supply the generated sample data to the parallel/serial converter 24. The parallel/serial converter 24 converts the parallel sample data into serial sample data.

The ultrasound diagnostic apparatus 10C also has the function of spatial compounding in which ultrasound images obtained by the ultrasound transmission and reception in mutually different directions are combined to produce a composite ultrasound image.

Similarly to the above ultrasound diagnostic apparatus 10A, the ultrasound diagnostic apparatus 10C combines, for example, three ultrasound images upon spatial compounding. Therefore, the transmission controller 32C and the reception controller 34C control the drive of the transmission drive 30 and the individual signal processors 20a, respectively, such that three types of ultrasound transmission and reception are performed in mutually different directions of ultrasound transmission and reception.

The probe 12C has the temperature sensor 42 for measuring the temperature of the signal processor 20. The temperature sensor 42 supplies the temperature measurement result to the reception controller 34C.

Upon spatial compounding, based on the temperature measurement result, the reception controller 34C adjusts the depth of the reception signals to be processed in the signal processor 20 and changes the depth of the ultrasound images to be combined by spatial compounding.

This point will be described in detail later.

The wireless communication unit 26 generates transmission signals from the serial sample data and transmits the serial sample data to the diagnostic apparatus body 14C via the antenna 28.

The wireless communication unit 26 receives various control signals from the diagnostic apparatus body 14C and outputs the received control signals to the communication controller 36.

The communication controller 36 controls the wireless communication unit 26. The communication controller 36 outputs the various control signals received by the wireless communication unit 26 to the probe controller 38.

The probe controller 38 controls various components of the probe 12C according to various control signals transmitted from the diagnostic apparatus body 14C.

As described above, the ultrasound diagnostic apparatus 10C of the invention has the function of producing an image (composite ultrasound image) through spatial compounding.

Figure 12:
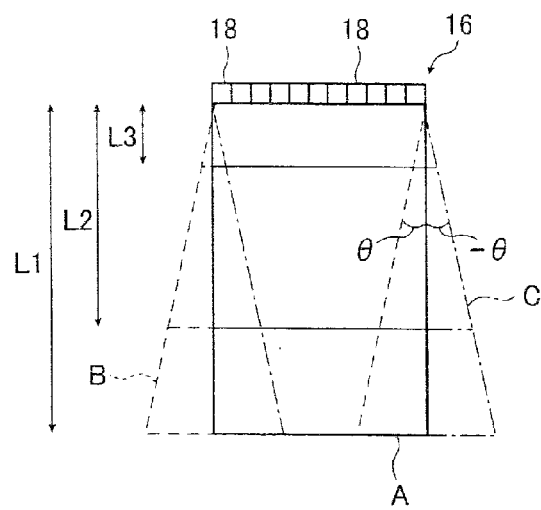
FIG. 12 is a conceptual diagram for illustrating reception signal processing through spatial compounding which is performed in the third embodiment of the ultrasound diagnostic apparatus according to the first aspect of the invention.

As in the ultrasound diagnostic apparatus 10A shown in FIG. 1, the ultrasound diagnostic apparatus 10C also performs, for example, the three types of ultrasound transmission and reception in mutually different directions upon spatial compounding as conceptually shown in FIG. 12 (FIG. 2). More specifically, upon spatial compounding, the probe 12C performs the three types of ultrasound transmission and reception, including the "transmission and reception for the image A" as the transmission and reception for obtaining the main image (image including the whole area of the composite ultrasound image formed by spatial compounding), the "transmission and reception for the image B" in a direction inclined by an angle of θ with respect to the direction of the transmission and reception for the image A, and the "transmission and reception for the image C" in a direction inclined by an angle of −θ with respect to the direction of the transmission and reception for the image A.

Figure 14A:
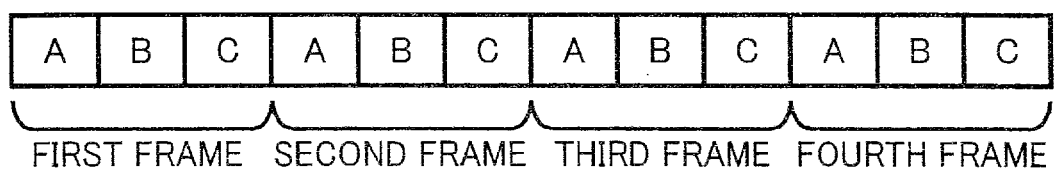
FIGS. 14A, 14B and 14C are conceptual diagrams for illustrating an example of spatial compounding which is performed in the third embodiment of the ultrasound diagnostic apparatus according to the first aspect of the invention.
Figure 14B:
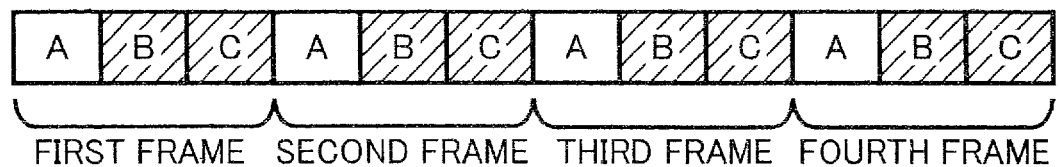
Figure 14C:
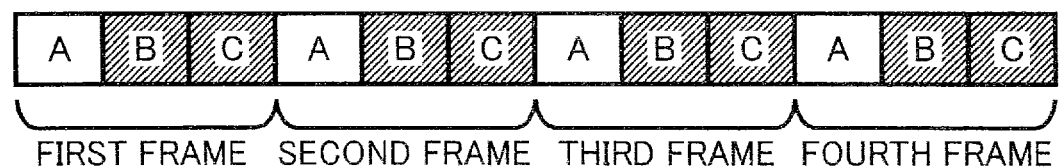

Also in this embodiment, when spatial compounding is performed, the probe 12C repeatedly performs the three types of ultrasound transmission and reception which make up a frame unit (see FIGS. 14A to 14C).

When spatial compounding is performed, the transmission controller 32C and the reception controller 34C of the probe 12C control the drive of the transmission drive 30 and the individual signal processors 20a, respectively, such that the three types of ultrasound transmission and reception are repeatedly performed.

On the other hand, when spatial compounding is performed, the diagnostic apparatus body 14C (more specifically an image combining unit 80) combines the three ultrasound images including the ultrasound image A (solid line) as the main image obtained by the transmission and reception for the image A, the ultrasound image B (broken line) obtained by the transmission and reception for the image B, and the ultrasound image C (chain line) obtained by the transmission and reception for the image C to produce a composite ultrasound image covering the region of the ultrasound image A.

Therefore, the number (predetermined number) of ultrasound images to be combined by spatial compounding in the ultrasound diagnostic apparatus 10C is three. However, the predetermined number may be two or four or more as in the above embodiments.

In addition, various known methods can be used to transmit and receive ultrasonic waves in different directions as in the above embodiments.

As described above, the probe 12C is provided with the temperature sensor 42 for measuring the temperature of the signal processor 20. The temperature measurement result obtained with the temperature sensor 42 is supplied to the reception controller 34C.

The temperature thresholds including the first temperature T5 [° C.] and the second temperature T6 [° C.] which is higher than T5 are set for the probe 12C (reception controller 34C). In the ultrasound diagnostic apparatus 10C, T5 and T6 may be fixed or variable if the relation of T5<T6 is met.

As described above, in the ultrasound diagnostic apparatus 10C, when spatial compounding is performed, the depth of the reception signal processing in the ultrasound transmission and reception which is performed in the individual signal processors 20a is changed based on the temperature measurement result obtained with the temperature sensor 42.

In the illustrated example, as conceptually shown in FIG. 12, three depths are set in the probe 12C (reception controller 34C) for the depth of the reception signal processing in the individual signal processors 20a (depth in the directions of ultrasound transmission and reception) in the ultrasound transmission and reception for obtaining ultrasound images to be combined by spatial compounding.

That is, ultrasound images having three different depths are set as the ultrasound images to be combined by spatial compounding. In other words, three types of ultrasound images different in size in the depth direction are set as the ultrasound images to be combined by spatial compounding.

In the first type, the reception signal processing is performed up to the "depth L1" (normal depth) which is the same as that of the composite ultrasound image to be produced by spatial compounding (i.e., main image) and the ultrasound image having a predetermined depth (a predetermined size in the depth direction) is generated.

In the second type, the reception signal processing is performed up to the "depth L3" (small depth) which is the smallest in the images to be combined by spatial compounding and the ultrasound image having the smallest depth (smallest size in the depth direction) is generated.

In the third type, the reception signal processing is performed up to the "depth L2" (medium depth) which is smaller than the depth L1 but larger than the depth L3 and the ultrasound image having the medium depth (medium size in the depth direction) is generated.

The depths L1, L2 and L3 in this embodiment may be the same as or different from those in the fourth embodiment to be described later.

In the illustrated example, the drive of the individual signal processors 20a of the signal processor 20 (more specifically the AFEs thereof) is activated or deactivated (on/off) to adjust the depth of the reception signal processing (adjust the depth of the ultrasound images).

Figure 13A:
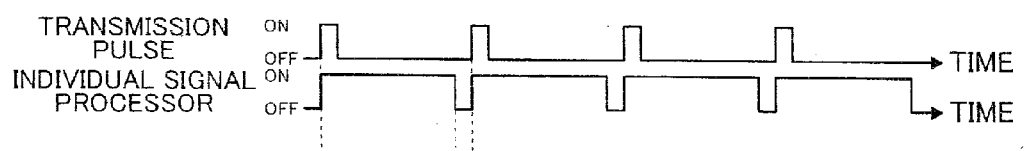
FIGS. 13A, 13B and 13C are conceptual diagrams for illustrating reception signal processing through spatial compounding which is performed in the third embodiment of the ultrasound diagnostic apparatus according to the first aspect of the invention.

More specifically, when the individual signal processor 20a performs the reception signal processing up to the depth L1, as conceptually shown in FIG. 13A, a transmission pulse is applied while at the same time the drive of the individual signal processor 20a is activated (on), and the drive of the individual signal processor 20a is deactivated (off) at a point in time when a time period corresponding to the depth L1 (depth corresponding to the composite ultrasound image) has passed.

Figure 13B:
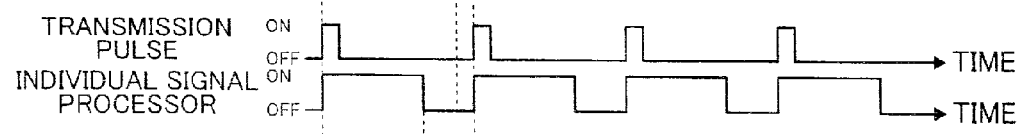

When the individual signal processor 20a performs the reception signal processing up to the depth L2, as conceptually shown in FIG. 13B, a transmission pulse is applied while at the same time the drive of the individual signal processor 20a is activated, and the drive of the individual signal processor 20a is deactivated at a point in time when a time period corresponding to the depth L2 which is smaller than the depth L1 has passed.

Figure 13C:
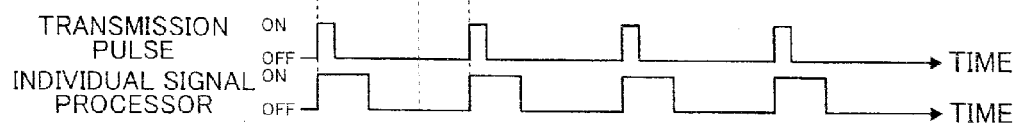

In addition, when the individual signal processor 20a performs the reception signal processing up to the depth L3, as conceptually shown in FIG. 13C, a transmission pulse is applied while at the same time the drive of the individual signal processor 20a is activated, and the drive of the individual signal processor 20a is deactivated at a point in time when a time period corresponding to the smallest depth L3 which is smaller than the depth L2 has passed.

As described above, as conceptually shown in FIGS. 12 and 14A to 14C, when spatial compounding is performed in the illustrated ultrasound diagnostic apparatus 10C, the three types of ultrasound transmission and reception for three images which are made in mutually different directions of ultrasound transmission and reception and which make up a frame unit for obtaining a composite ultrasound image are repeatedly performed on a frame basis.

For example, as shown in FIGS. 12 and 14A to 14C, the transmission controller 32C and the reception controller 34C first perform the transmission and reception for the image A for obtaining the ultrasound image A as the main image.

Then, the transmission controller 32C and the reception controller 34C perform the transmission and reception for the image B for obtaining the ultrasound image B in the direction inclined by the angle of θ with respect to the direction for the ultrasound image A.

Then, the transmission controller 32C and the reception controller 34C perform the transmission and reception for the image C for obtaining the ultrasound image C in the direction inclined by the angle of −θ with respect to the direction for the ultrasound image A.

In FIGS. 14A to 14C, areas each having a black letter on a white background correspond to the processing of the reception signals up to the depth L1 (normal depth); coarsely hatched (shaded) areas correspond to the processing of the reception signals up to the depth L2 (medium depth); and densely hatched areas correspond to the processing of the reception signals up to the depth L3 (small depth).

When the temperature measurement result obtained with the temperature sensor 42 is less than T5 upon spatial compounding, the reception controller 34C of the probe 12C in the ultrasound diagnostic apparatus 10C controls the drive of the individual signal processors 20a so that, in one frame, the reception signal processing in the transmission and reception for the images A, B and C is all performed up to the depth L1 as shown in FIG. 14A.

The case in which the temperature measurement result obtained with the temperature sensor 42 is less than T5 refers to the case in which the probe 12C (signal processor 20) has a steady temperature.

When the temperature measurement result obtained with the temperature sensor 42 is equal to or more than T5 but less than T6, the reception controller 34C controls the drive of the individual signal processors 20a so that, in one frame, the reception signal processing in the transmission and reception for the image A is performed up to the depth L1 and that in the transmission and reception for the images B and C is performed up to the depth L2 as shown in FIG. 14B.

That is, according to this processing, spatial compounding is not performed in the region distant from the piezoelectric unit 16 (region beyond the depth L2) and the deeper region of the composite ultrasound image is only made up of the ultrasound image A.

In addition, when the temperature measurement result obtained with the temperature sensor 42 is equal to or more than T6, the reception controller 34C controls the drive of the individual signal processors 20a so that, in one frame, the reception signal processing in the transmission and reception for the image A is performed up to the depth L1 and that in the transmission and reception for the images B and C is performed up to the depth L3 as shown in FIG. 14C.

That is, according to this processing, the three ultrasound images are combined by spatial compounding to obtain a high-quality image only in the region near the piezoelectric unit 16.

As is clear from the above description, in cases where the temperature of the probe 12C is increased upon spatial compounding, the ultrasound diagnostic apparatus 10C reduces the processing depth in the processing of the reception signals from the ultrasound transmission and reception for obtaining ultrasound images to be combined into a composite ultrasound image. That is, when the temperature of the probe 12C is increased, the ultrasound diagnostic apparatus 10C reduces the drive time of the individual signal processors 20a for processing the reception signals from the ultrasonic echoes depending on the temperature.

Therefore, according to the invention, the internal temperature of the probe 12C can be promptly reduced by stopping the signal processor 20 which is the major heat generation area even if the temperature of the probe 12C is increased during spatial compounding. Even if the temperature of the probe 12C is increased, the image quality deterioration can be minimized by promptly reducing the temperature inside the probe 12C while suppressing the temperature increase therein.

In the example shown in FIGS. 14A to 14C, the processing depth of all the reception signals is the same in one frame making up a composite ultrasound image. However, this is not the sole case of the invention and the reception signals of one or more ultrasound images in each frame (each composite ultrasound image) may be different.

Figure 15A:
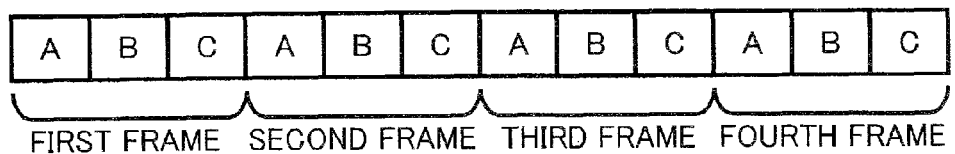
FIGS. 15A, 15B, 15C, 15D and 15E are conceptual diagrams for illustrating another example of spatial compounding which is performed in the third embodiment of the ultrasound diagnostic apparatus according to the first aspect of the invention.
Figure 15B:
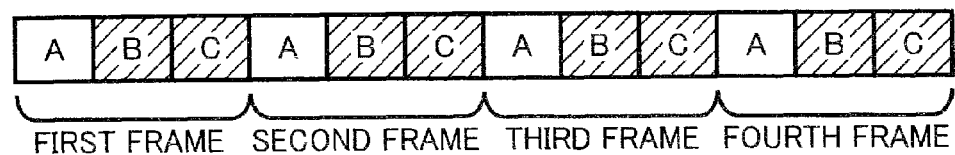
Figure 15C:
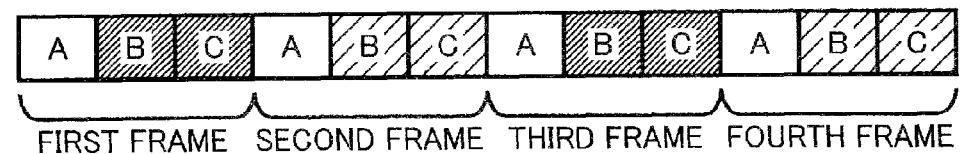

An example of the reception signal processing is conceptually shown in FIGS. 15A to 15C.

In this example, when the temperature measurement result obtained with the temperature sensor 42 is equal to or more than T6, as shown in FIG. 15C, the reception signal processing in the transmission and reception for the image A is performed up to the depth L1 for all the frames but the reception signal processing for the other images is performed so that the depth is different between the odd frames and the even frames. More specifically, the reception signal processing for the images B and C is performed up to the depth T3 in the odd frames and up to the depth L2 in the even frames.

FIG. 15A showing the case where the temperature measurement result is less than T5 and FIG. 15B showing the case where the temperature measurement result is equal to or more than T5 but less than T6 are similar to FIG. 14A and FIG. 14B, respectively.

Figure 15D:
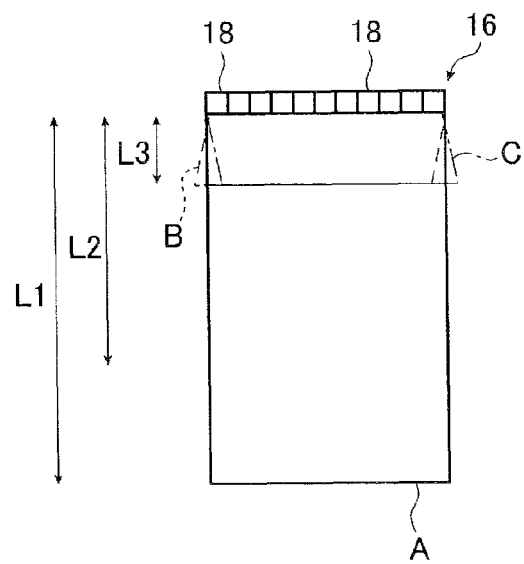
Figure 15E:
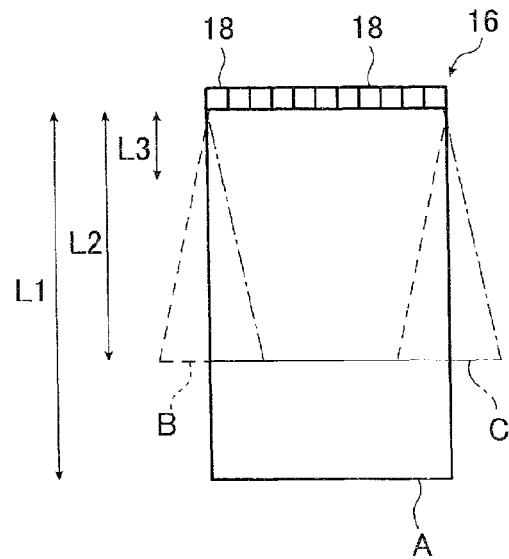

Therefore, in this example, when the temperature measurement result obtained with the temperature sensor 42 is equal to or more than T6, the ultrasound images A to C as shown in FIG. 15D are combined to obtain the composite ultrasound image in each odd frame, whereas the ultrasound images A to C as shown in FIG. 15E are combined to obtain the composite ultrasound image in each even frame.

In this example, the depth of the images to be combined by spatial compounding can be increased in every two frames and therefore the image quality deterioration in the section from the deeper end of the depth L3 to the deeper end of the depth L2 can be reduced compared to the example shown in FIGS. 14A to 14C in which the images produced by spatial compounding are observed as consecutive images.

In the example shown in FIGS. 14A to 14C, when the temperature in the case shown in FIG. 14B is equal to or more than T5 but less than T6, the same ultrasound image as that shown in FIG. 15E is obtained, and when the temperature in the case shown in FIG. 14C is equal to or more than T6, the same ultrasound image as that shown in FIG. 15D is obtained.

In the above example, when the temperature measurement result obtained with the temperature sensor 42 is equal to or more than T5 but less than T6 or equal to or more than T6, the images in one frame for which the depth of the reception signal processing was changed from the depth L1 both have the same depth. However, this is not the sole case of the invention.

In other words, the reception signal processing up to the depth L2 and that up to the depth L3 may be performed in one frame. The reception signal processing up to the depth L1, that up to the depth L2 and that up to the depth L3 may be performed in one frame.

Figure 16A:
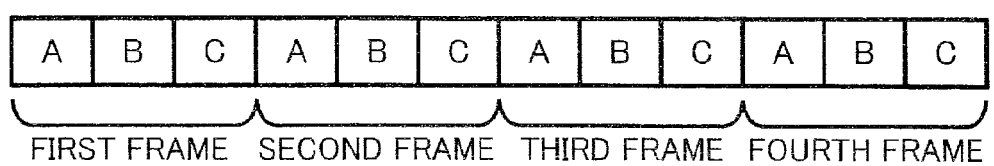
FIGS. 16A, 16B and 16C are conceptual diagrams for illustrating yet another example of spatial compounding which is performed in the third embodiment of the ultrasound diagnostic apparatus according to the first aspect of the invention.
Figure 16B:
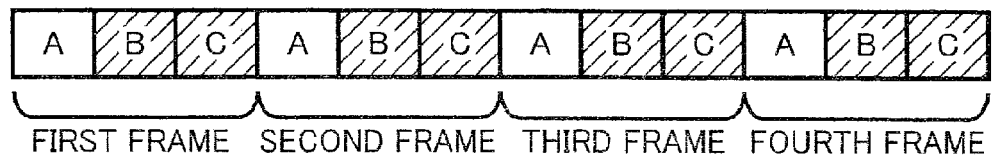
Figure 16C:
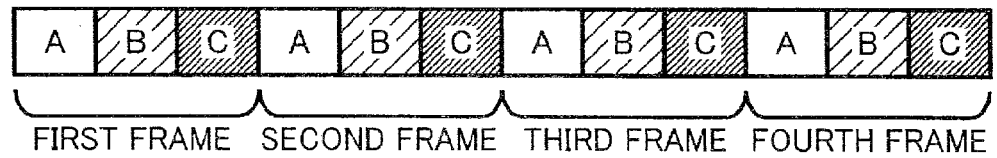

An example of the reception signal processing is conceptually shown in FIGS. 16A to 16C.

In this example, as in FIG. 14A, when the temperature measurement result obtained with the temperature sensor 42 is less than T5, the reception signal processing for all the images A, B and C is performed up to the depth L1 as shown in FIG. 16A. As in FIG. 14B, when the temperature measurement result obtained with the temperature sensor 42 is equal to or more than T5 but less than T6, the reception signal processing for the image A is performed up to the depth L1 and that for the images B and C is performed up to the depth L2 as shown in FIG. 16B.

In contrast, in this example, when the temperature measurement result obtained with the temperature sensor 42 is equal to or more than T6, the reception signal processing for the image A is performed up to the depth L1, that for the image B up to the depth L2 and that for the image C up to the depth L3 as shown in FIG. 16C. Alternatively, the depth of the images A, B and C may be set to the depth L1, depth L3 and the depth L2, respectively.

Compared to the example shown in FIGS. 14A to 14C, this method reduces the effect of preventing heat generation but is advantageous in terms of the image quality of the composite ultrasound images.

In this example, when the temperature measurement result obtained with the temperature sensor 42 is equal to or more than T6, the reception signal processing up to the depth L2 and the reception signal processing up to the depth L3 may be alternately performed for the images B and C.

An example is shown in FIGS. 17A to 17E.

Figure 17A:
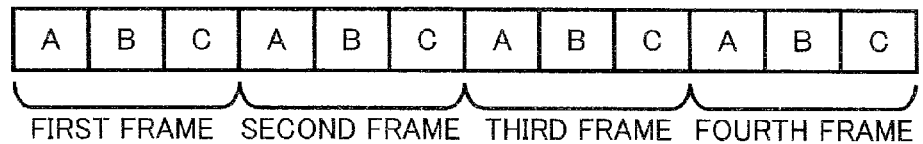
FIGS. 17A, 17B, 17C, 17D and 17E are conceptual diagrams for illustrating still another example of spatial compounding which is performed in the third embodiment of the ultrasound diagnostic apparatus according to the first aspect of the invention.
Figure 17B:
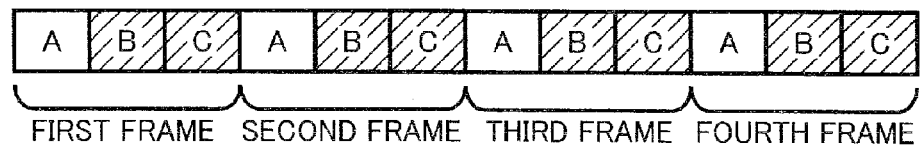
Figure 17C:
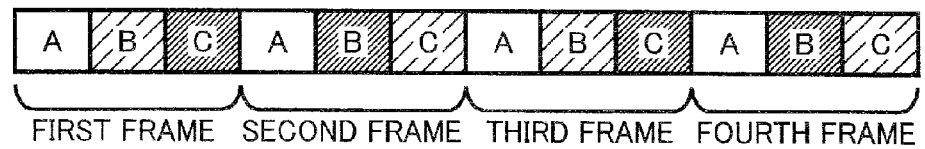

In the example shown in FIGS. 17A to 17E, when the temperature measurement result obtained with the temperature sensor 42 is equal to or more than T6, in the odd frames; the reception signal processing for the image A is performed up to the depth L1, that for the image B up to the depth L2 and that for the image C up to the depth L3 as shown in FIG. 17C (as in FIG. 16C). In contrast, in the even frames, the reception signal processing for the image A is performed up to the depth L1 but that for the images B and C is performed up to the depths L3 and L2, respectively.

Also in FIGS. 17A and 17B, FIG. 17A showing the case where the temperature measurement result is less than T5 and FIG. 17B showing the case where the temperature measurement result is equal to or more than T5 but less than T6 are similar to FIG. 16A and FIG. 16B, respectively.

Figure 17D:
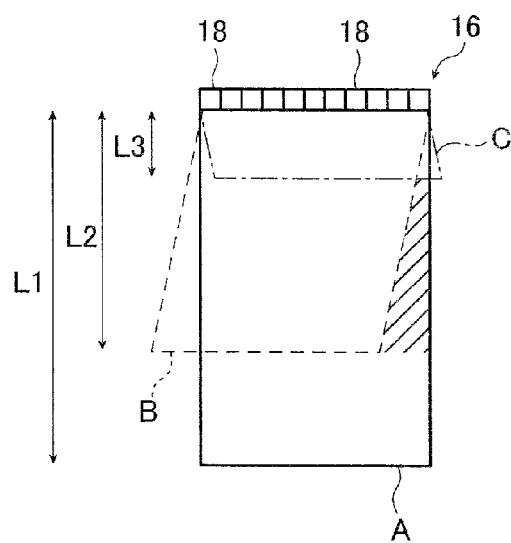
Figure 17E:
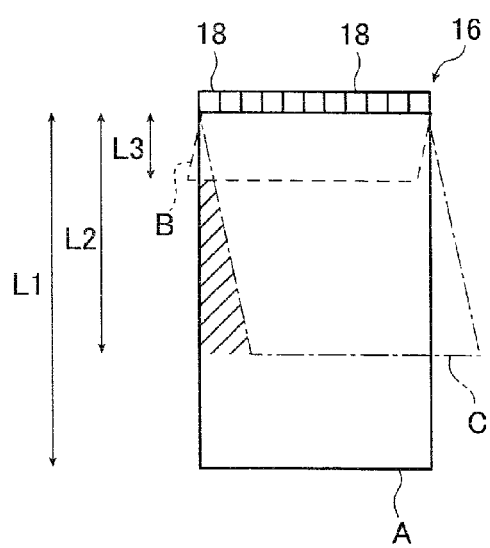

Therefore, in this example, when the temperature measurement result obtained with the temperature sensor 42 is equal to or more than T6, the ultrasound images A to C having three different depths as shown in FIG. 17D are combined to obtain the composite ultrasound image in each odd frame, whereas the ultrasound images A to C having three different depths as shown in FIG. 17E are combined to obtain the composite ultrasound image in each even frame.

In this example, the composite ultrasound image shown in FIG. 17D and the composite ultrasound image shown in FIG. 17E are replaced by each other in every two frames. Therefore, in the regions shown by the oblique lines in FIGS. 17D and 17E which are made up of one image, one-image composition and two-image composition are alternately used in very two frames. Accordingly, when the images produced by spatial compounding are observed as continuous images, portions having continuously and partly deteriorating image quality can be eliminated to suppress the deterioration of the mage quality of the composite ultrasound images.

In the above example, when the temperature in the probe 12C is increased, the depth of the reception signal processing is changed to L2 or L3 in the transmission and reception for the image B and/or those for the image C but this is not the sole case of the invention. That is, the depth of the reception signal processing in the transmission and reception for the image A may be changed to L2 or L3 depending on the temperature increase.

However, the ultrasound image A is the main image. In other words, the composite ultrasound image produced in the diagnostic apparatus body 14C through spatial compounding is the image having the region of the ultrasound image A (transmission and reception for the image A). Therefore, when the reception signal processing up to the depth L1 is included in one frame, it is more advantageous to process the reception signals derived from the transmission and reception for the image A serving as the main image up to the depth L1 because a proper composite ultrasound image can be consistently obtained.

In the above example, the processing for at least one image (the reception signal processing for the image A) is performed up to the depth L1 at any temperature. However, this is not the sole case of the invention and the reception signal processing for all the images may be performed up to the depth L2 or L3 depending on the temperature.

Figure 18A:
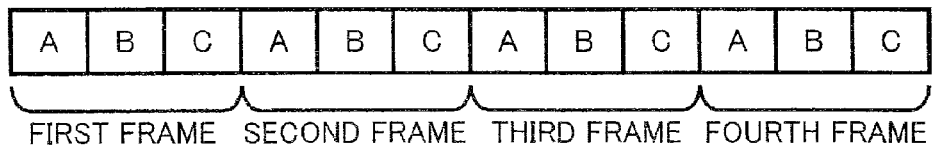
FIGS. 18A, 18B and 18C are conceptual diagrams for illustrating still yet another example of spatial compounding which is performed in the third embodiment of the ultrasound diagnostic apparatus according to the first aspect of the invention.
Figure 18B:
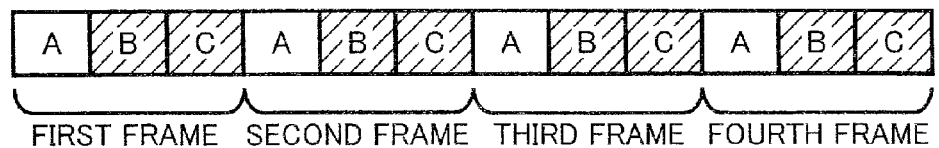
Figure 18C:
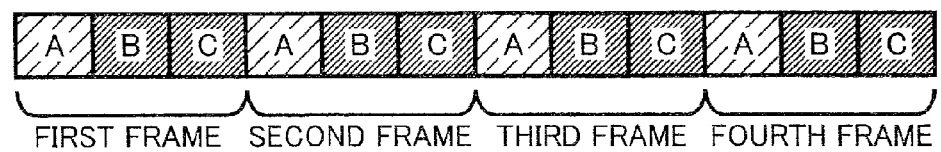

An example of the ultrasound transmission and reception is conceptually shown in FIGS. 18A to 18C.

In this example, as in FIG. 14A, when the temperature measurement result obtained with the temperature sensor 42 is less than T5, the reception signal processing for the images A, B and C is all performed up to the depth L1 as shown in FIG. 18A. As in FIG. 14B, when the temperature measurement result obtained with the temperature sensor 42 is equal to or more than T5 but less than the reception signal processing for the image A is performed up to the depth L1 and that for the images B and C is performed up to the depth L2 as shown in FIG. 18B.

In contrast, in this example, when the temperature measurement result obtained with the temperature sensor 42 is equal to or more than T6, the reception signal processing for the image A is performed up to the depth L2, and that for the images B and C up to the depth L3 as shown in FIG. 18C.

According to this example, the depth of the resulting composite ultrasound image is reduced but the effect of preventing heat generation is increased.

In this example, when the temperature measurement result obtained with the temperature sensor 42 is equal to or more than T5, the depth of the reception signal processing for the two images was changed from the depth L1 but this is not the sole case of the invention. That is, the depth of the reception signal processing for only one image or three or more images may be changed from the depth L1 based on the temperature measurement result obtained with the temperature sensor 42.

Considering the purpose that the temperature increase within the probe 12C is suppressed while minimizing the image quality deterioration due to the temperature increase, when the temperature exceeds one of the thresholds, the depth of the reception signal processing for two or more images is preferably changed from the depth L1. In addition, in order to suppress the temperature increase while preventing the image quality deterioration, when the temperature exceeds one of the thresholds, the depth of the reception signal processing for all the images except the image A (main image) is preferably changed from the depth L1 depending on the temperature.

In addition, in the above examples, since the predetermined number upon spatial compounding is three, two temperature thresholds are provided. However, this is not the sole case of the invention and in cases where the predetermined number is four or more, three or more thresholds may be provided.

The number of depths set for the reception signal processing depending on the temperature is also not limited to three. For example, two depths including the normal depth (L1) and the small depth (L3) may be provided. Alternatively, four or more depths of reception signal processing may be provided by setting a plurality of medium depths such as the depth L2-1 and the depth L2-2 between the normal depth L1 and the small depth L3.

In the examples shown in FIGS. 14A to 18C, the order of ultrasound transmission and reception in one frame is the same for all the frames. However, this is not the sole case of the invention and the order of ultrasound transmission and reception of the images in each frame may be different.

Figure 19A:
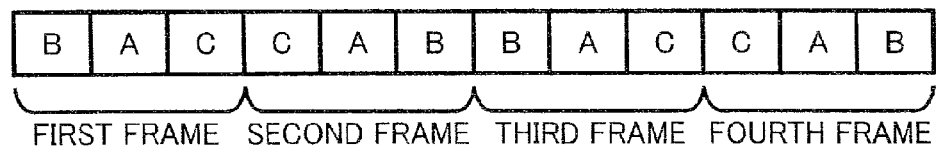
FIGS. 19A, 19B and 19C are conceptual diagrams for illustrating a further example of spatial compounding which is performed in the third embodiment of the ultrasound diagnostic apparatus according to the first aspect of the invention.
Figure 19B:
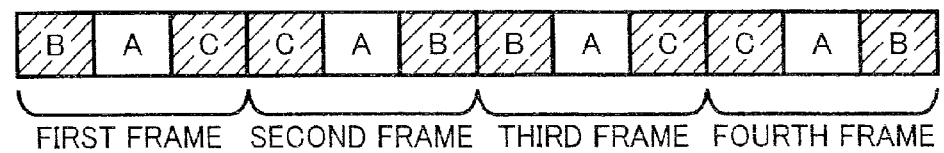
Figure 19C:
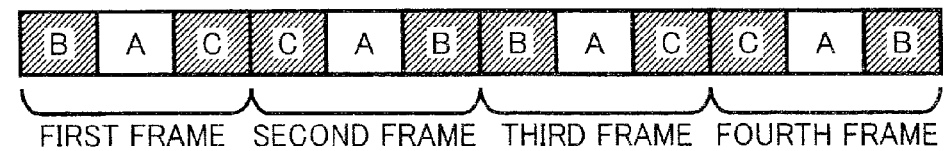

For example, as shown in FIGS. 19A to 19C, the ultrasound transmission and reception of the first frame, the second frame, the third frame, the fourth frame and the like may be performed in the orders of "image B→image A→image C", "image C→image A→image B", "image B→image A→image C", "image C→image A→mage B" and the like, respectively.

That is, also in the third embodiment of the ultrasound diagnostic apparatus 10C, as in the first embodiment, the directions of ultrasound transmission and reception in the last ultrasound image in the earlier one of two consecutive frames (i.e., two temporally consecutive composite ultrasound images) and the first ultrasound image in the subsequent frame may be the same.

This order of ultrasound transmission and reception enables the ultrasound transmission and reception to be continued in the same directions to facilitate the control of the transmission drive 30 and the individual signal processors 20a.

As described above, the reception signals outputted from the probe 12C are supplied to the diagnostic apparatus body 14C by wireless communication.

Similarly to the first embodiment of the diagnostic apparatus body 10A shown in FIG. 1, the diagnostic apparatus body 14C includes an antenna 50, a wireless communication unit 52, a serial/parallel converter 54, a data storage unit 56, an image generating unit 58, a display controller 62, a monitor 64, a communication controller 68, an apparatus body controller 70 and an operating unit 72.

As in the above embodiment, the diagnostic apparatus body 14C includes a built-in power supply unit (not shown), which supplies electric power for drive to each component.

The antenna 50, the wireless communication unit 52, the serial/parallel converter 54, the data storage unit 56, the image generating unit 58, the display controller 62, the monitor 64, the communication controller 68 and the apparatus-body controller 70 are basically the same as those in the diagnostic apparatus body 10A shown in FIG. 1.

More specifically, the wireless communication unit 52 performs wireless communication with the probe 12C via the antenna 50 to transmit control signals to the probe 12C and receive signals sent from the probe 12C. The wireless communication unit 52 demodulates the received signals and outputs them to the serial/parallel converter 54 as serial sample data.

The communication controller 68 controls the wireless communication unit 52 so that various control signals are transmitted according to the settings made by the apparatus body controller 70.

The serial/parallel converter 54 converts the serial sample data into parallel sample data. The data storage unit 56 stores at least one frame of sample data converted by the serial/parallel converter 54.

The image generating unit 58 (phase adjusting and summing unit 76, image processor 78 and image combining unit 80) performs reception focusing on sample data for each image read out from the data storage unit 56 to generate image signals representing an ultrasound image.

As described above, when spatial compounding is performed in the ultrasound diagnostic apparatus 10C, the probe 12C performs, for example, the ultrasound transmission and reception for three images, that is, the transmission and reception for the images A, B and C.

When spatial compounding is performed, the image combining unit 80 of the image generating unit 58 accordingly combines the ultrasound image A derived from the transmission and reception for the image A, the ultrasound image B derived from the transmission and reception for the image B, and the ultrasound image C derived from the transmission and reception for the image C to generate image signals for a composite ultrasound image.

As described above, when spatial compounding is performed in the ultrasound diagnostic apparatus 10C, the probe 12C changes, based on the temperature measurement result obtained with the temperature sensor 42, the depth of the ultrasonic echoes to be subjected to the reception signal processing which is used to obtain the ultrasound images to be combined. Therefore, the ultrasound images to be combined by spatial compounding accordingly have a depth (size in the depth direction) corresponding to the depth L1, L2 or L3.

The display controller 62 causes the monitor 64 to display the ultrasound image according to the image signals generated by the image generating unit 58.

Under the control of the display controller 62, the monitor 64 displays the ultrasound image.

The apparatus body controller 70 controls the components in the diagnostic apparatus body 14C. The apparatus body controller 70 is connected to the operating unit 72 to perform various input operations including as to whether or not spatial compounding is to be performed.

The operation of the ultrasound diagnostic apparatus 10C shown in FIG. 11 is described below.

Similarly to the ultrasound diagnostic apparatus 10A, during the diagnosis, various kinds of information inputted to the operating unit 72 are first sent to the probe 12C by wireless communication and then supplied to the probe controller 38 also in the ultrasound diagnostic apparatus 10C.

Then, ultrasonic waves are transmitted from the transducers 18 in accordance with the drive voltage supplied from the transmission drive 30 of the probe 12C.

The reception signals outputted from the transducers 18 that have received the ultrasonic echoes generated by reflection of the ultrasonic waves on the subject are supplied to the corresponding individual signal processors 20a to generate sample data.

In the probe 12C, when spatial compounding is performed, the temperature measurement result of the signal processor 20 obtained with the temperature sensor 42 is sent to the reception controller 34C.

As described above, when spatial compounding is performed in the ultrasound diagnostic apparatus 10C, the probe 12C adjusts, based on the temperature measurement result of the reception processor 20 obtained with the temperature sensor 42, the depth in the reception signal processing for obtaining the ultrasound images to be combined. More specifically, the probe 12C sets the depth of the reception signal processing for the ultrasound images to be combined to one of the depths L1, L2 and L3 so that the depth of any of the ultrasound images to be combined may be reduced each time the temperature exceeds one of the thresholds according to the temperature measurement result obtained with the temperature sensor 42 and controls the drive of the individual signal processors 20a for processing the reception signals.

For example, when the temperature measured with the temperature sensor 42 is less than T5, the reception controller 34C controls the operation of the signal processor 20 (individual signal processors 20a) so as to process the reception signals for all of the images A, B and C up to the depth L1 as shown in 14A.

When the temperature measured with the temperature sensor 42 is equal to or more than T5 but less than T6, the reception controller 34C controls the operation of the signal processor 20 so as to process the reception signals for the image A up to the depth L1 and those for the images B and C up to the depth L2 as shown in 14B.

In addition, when the temperature measured with the temperature sensor 42 is equal to or more than T6, the reception controller 34C controls the operation of the signal processor 20 so as to process the reception signals for the image A up to the depth L1 and those for the images B and C up to the depth L3 as shown in 14C.

The sample data generated by the individual signal processors 20a are sent to the parallel/serial converter 24, where the sample data is converted into serial data. The serial data is then wirelessly transmitted from the wireless communication unit 26 (antenna 28) to the diagnostic apparatus body 14C.

The sample data received by the wireless communication unit 52 of the diagnostic apparatus body 14C is converted into parallel data in the serial/parallel converter 54 and stored in the data storage unit 56.

Further, the sample data for each image is read out from the data storage unit 56 to generate image signals of an ultrasound image in the image generating unit 58. The display controller 62 causes the monitor 64 to display the ultrasound image based on the image signals.

When spatial compounding is performed, the image combining unit 80 of the image generating unit 58 combines the ultrasound images.

More specifically, as described above, when spatial compounding is performed, the image combining unit 80 combines the ultrasound image A derived from the transmission and reception for the image A, the ultrasound image B derived from the transmission and reception for the image B, and the ultrasound image C derived from the transmission and reception for the image C to generate image signals for a composite ultrasound image, and outputs the image signals to the display controller 62.

As described above, when spatial compounding is performed in the ultrasound diagnostic apparatus 10C, the probe 12C controls the drive of the individual signal processors 20a based on the temperature measurement result obtained with the temperature sensor 42 such that the depth of any of the ultrasound images to be combined is reduced each time the temperature exceeds one of the temperature thresholds. Therefore, the ultrasound images to be combined in the image combining unit 80 are also various combinations of normal depth images, medium depth images and small depth images based on the temperature measurement results obtained with the temperature sensor 42.

For example, in the above example shown in FIGS. 14A to 14C, when the temperature measured with the temperature sensor 42 in the probe 12C is less than T5, the ultrasound images A, B and C to be combined in the image combining unit 80 all have the normal depth. When the temperature measured with the temperature sensor 42 in the probe 12C is equal to or more than T5 but less than T6, the ultrasound images to be combined in the image combining unit 80 include the ultrasound image A having the normal depth and the ultrasound images B and C having the medium depth. In addition, when the temperature measured with the temperature sensor 42 in the probe 12C is equal to or more than T6, the ultrasound images to be combined in the image combining unit 80 include the ultrasound image A having the normal depth and the ultrasound images B and C having the small depth.

FIG. 20 is a conceptual block diagram showing the fourth embodiment of the ultrasound diagnostic apparatus according to the first aspect of the invention.

Many components of the ultrasound diagnostic apparatus 10D shown in FIG. 20 are the same as those of the ultrasound diagnostic apparatus 10A shown in FIG. 1. Therefore, like components are denoted by the same reference numerals and the following description mainly focuses on the different features.

As in the first embodiment of the ultrasound diagnostic apparatus 10A, the ultrasound diagnostic apparatus 10D shown in FIG. 20 includes an ultrasound probe 12D (hereinafter referred to as "probe 12D") and a diagnostic apparatus body 14D. As in the above embodiment, the ultrasound probe 12D is connected to the diagnostic apparatus body 14D by wireless communication.

Similarly to the probe 12A in the first embodiment, the probe 12D transmits ultrasonic waves to the subject, receives ultrasonic echoes generated by reflection of the ultrasound waves on the subject, and outputs reception signals of an ultrasound image in accordance with the received ultrasonic echoes.

There is no limitation on the type of the probe 12D and various known ultrasound probes can be used.

As in the probe 12A, the probe 12D also includes a piezoelectric unit 16, a signal processor 20, a parallel/serial converter 24, a wireless communication unit 26, an antenna 28, a transmission drive 30, a transmission controller 32D, a reception controller 34D, a communication controller 36, a probe controller 38 and a temperature sensor 42.

The probe 12D also includes a built-in battery (not shown), which supplies electric power for drive to each component.

The piezoelectric unit 16, the signal processor 20, the parallel/serial converter 24, the wireless communication unit 26, the antenna 28, the transmission drive 30, the communication controller 36, the probe controller 38 and the temperature sensor 42 are basically the same as those of the probe 12A.

More specifically, the piezoelectric unit 16 is a one-dimensional or two-dimensional array of transducers 18 transmitting and receiving ultrasonic waves.

The transmission drive 30 supplies the transducers 18 with a drive voltage so that the transducers transmit ultrasonic waves so as to form ultrasonic beams.

The transducers 18 output the reception signals of the ultrasonic echoes to individual signal processors 20a of the signal processor 20. As described above, each individual signal processor 20a has an AFE, processes the reception signals to generate sample data and supplies the generated sample data to the parallel/serial converter 24. The parallel/serial converter 24 converts the parallel sample data into serial sample data.

The ultrasound diagnostic apparatus 10D also has the function of spatial compounding in which ultrasound images obtained by the ultrasound transmission and reception in mutually different directions are combined to produce a composite ultrasound image.

Similarly to the above ultrasound diagnostic apparatus 10A, the ultrasound diagnostic apparatus 10D combines, for example, three ultrasound images upon spatial compounding. Therefore, the transmission controller 32D and the reception controller 34D control the drive of the transmission drive 30 and the individual signal processors 20a, respectively, such that three types of ultrasound transmission and reception are performed in mutually different directions of ultrasound transmission and reception.

The probe 12D has the temperature sensor 42 for measuring the temperature of the signal processor 20. The temperature sensor 42 supplies the temperature measurement result to the reception controller 34D.

Upon spatial compounding, based on the temperature measurement result, the reception controller 34D adjusts the depth of the reception signals to be processed in the signal processor 20 and reduces the number of sound rays in the regions of the ultrasound images to be combined by spatial compounding beyond the predetermined depth.

This point will be described in detail later.

The wireless communication unit 26 generates transmission signals from the serial sample data and transmits the serial sample data to the diagnostic apparatus body 14D via the antenna 28.

The wireless communication unit 26 receives various control signals from the diagnostic apparatus body 14D and outputs the received control signals to the communication controller 36.

The communication controller 36 controls the wireless communication unit 26. The communication controller 36 outputs the various control signals received by the wireless communication unit 26 to the probe controller 38.

The probe controller 38 controls various components of the probe 12D according to various control signals transmitted from the diagnostic apparatus body 14D.

As described above, the ultrasound diagnostic apparatus 10D of the invention has the function of producing an image (composite ultrasound image) through spatial compounding.

Figure 21A:
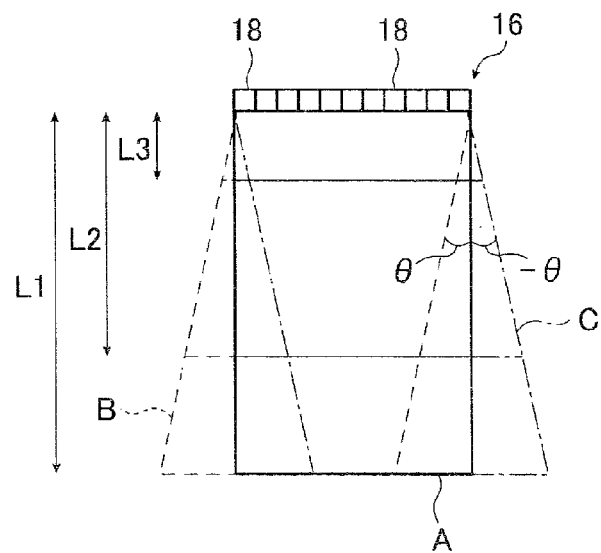
FIGS. 21A, 21B and 21C are conceptual diagrams for illustrating sound ray reduction through spatial compounding which is performed in the fourth embodiment of the ultrasound diagnostic apparatus according to the first aspect of the invention.

As in the ultrasound diagnostic apparatus 10A shown in FIG. 1, the ultrasound diagnostic apparatus 10D also performs, for example, the three types of ultrasound transmission and reception in mutually different directions upon spatial compounding as conceptually shown in FIG. 21A (FIG. 2). More specifically, upon spatial compounding, the probe 12D performs the three types of ultrasound transmission and reception, including the "transmission and reception for the image A" as the ultrasound transmission and reception for obtaining the main image (image including the whole area of the composite ultrasound image formed by spatial compounding), the "transmission and reception for the image B" in a direction inclined by an angle of θ with respect to the direction of the transmission and reception for the image A, and the "transmission and reception for the image C" in a direction inclined by an angle of −θ with respect to the direction of the transmission and reception for the image A.

Figure 23A:
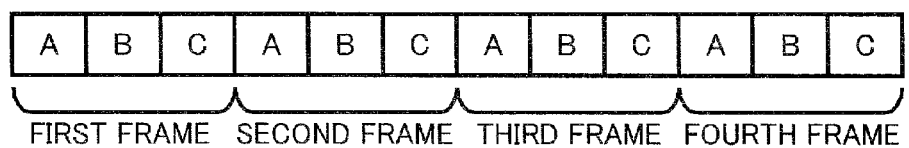
FIGS. 23A, 23B and 23C are conceptual diagrams for illustrating an example of spatial compounding which is performed in the fourth embodiment of the ultrasound diagnostic apparatus according to the first aspect of the invention.
Figure 23B:
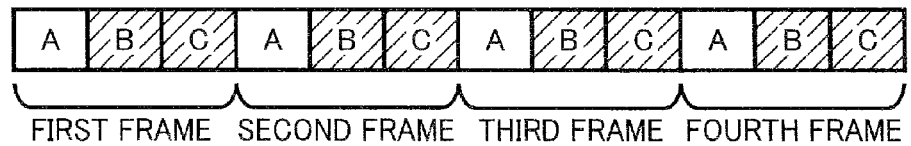
Figure 23C:
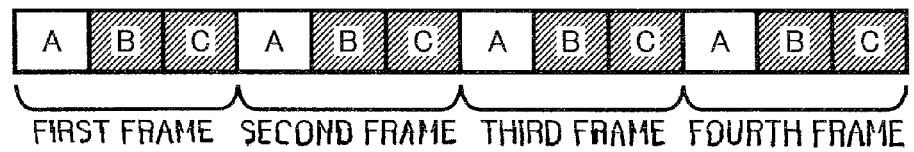

Also in this embodiment, when spatial compounding is performed, the probe 12D repeatedly performs the three types of ultrasound transmission and reception which make up a frame unit (see FIGS. 23A to 23C).

When spatial compounding is performed, the transmission controller 32D and the reception controller 34D of the probe 12D control the drive of the transmission drive 30 and the individual signal processors 20a, respectively, such that the three types of ultrasound transmission and reception are repeatedly performed.

On the other hand, when spatial compounding is performed, the diagnostic apparatus body 14D (more specifically an image combining unit 80) combines the three ultrasound images including the ultrasound image A (solid line) as the main image obtained by the transmission and reception for the image A, the ultrasound image B (broken line) obtained by the transmission and reception for the image B, and the ultrasound image C (chain line) obtained by the transmission and reception for the image C to produce a composite ultrasound image covering the region of the ultrasound image A.

Therefore, the number (predetermined number) of ultrasound images to be combined by spatial compounding in the ultrasound diagnostic apparatus 10D is three. However, the predetermined number may be two or four or more as in the above embodiments.

In addition, various known methods can be used to transmit and receive ultrasonic waves in different directions as in the above embodiments.

As described above, the probe 12D is provided with the temperature sensor 42 for measuring the temperature of the signal processor 20. The temperature measurement result obtained with the temperature sensor 42 is supplied to the reception controller 34D.

The temperature thresholds including the first temperature T7 [° C.] and the second temperature T8 [° C.] which is higher than T7 are set for the probe 12D (the reception controller 34D). In the ultrasound diagnostic apparatus 10D, T7 and T8 may be fixed or variable if the relation of T7<T8 is met.

In the ultrasound diagnostic apparatus 10D, when spatial compounding is performed, the number of sound rays in the ultrasound image is reduced in the region beyond the predetermined depth based on the temperature measurement result obtained with the temperature sensor 42.

In the illustrated example, as conceptually shown in FIG. 21A, three depths are set in the probe 12D (reception controller 34D) for the depth (depth in the directions of ultrasound transmission and reception) beyond which the number of sound rays is reduced upon spatial compounding. The first is the depth L1 (normal depth) within which the number of sound rays is not reduced, that is, all the sound rays have the same depth as that of the composite ultrasound image to be produced by spatial compounding. The second is the shallowest or smallest depth L3. The third is the depth L2 (medium depth) which is the depth between the depth L1 and the depth L3.

For example, the probe 12D reduces the number of sound rays by eliminating one of every two sound rays based on the temperature measurement result obtained with the temperature sensor 42.

Figure 21B:
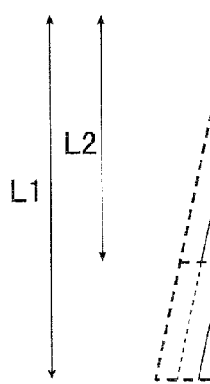
Figure 21C:
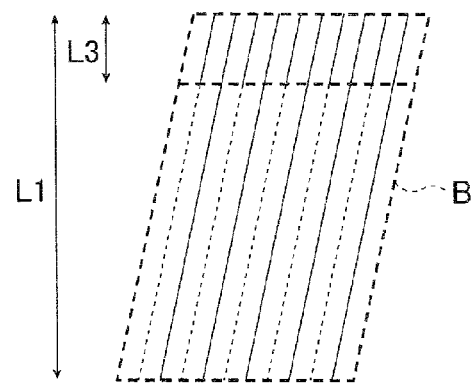

When the number of sound rays is reduced beyond the depth L2, the sound rays for producing the ultrasound image is as conceptually shown in FIG. 21B (illustrated by the ultrasound image B) in which the sound rays are shown by thin solid lines and the eliminated sound rays are shown by thin broken lines. When the number of sound rays is reduced beyond the depth L3, the sound rays for producing the ultrasound image is as conceptually shown in FIG. 21C.

The portions of the image corresponding to the sound rays eliminated by the probe 12D, that is, the portions shown by thin broken lines are produced later by interpolation using the surrounding sound, rays in the image generating unit 58 of the diagnostic apparatus body 14D.

In this embodiment, the number of sound rays is reduced in the region beyond the predetermined depth by eliminating one of every two sound rays as in the illustrated case (the number of sound rays is reduced by half). However, this is not the sole case of the invention. Therefore, in this embodiment, the number of sound rays may be reduced in the region beyond the predetermined depth by eliminating one of every three sound rays (the number of sound rays is reduced to two-thirds) or by eliminating one of every four sound rays (the number of sound rays is reduced to three-fourths).

Alternatively, the number of sound rays in the region beyond the predetermined depth may be reduced by eliminating two or more than two consecutive sound rays.

In the illustrated example, the drive of the individual signal processors 20a of the signal processor 20 (more specifically the AFEs thereof) is activated or deactivated (on/off) to reduce the number of sound rays in the region beyond the predetermined depth.

Figure 22A:
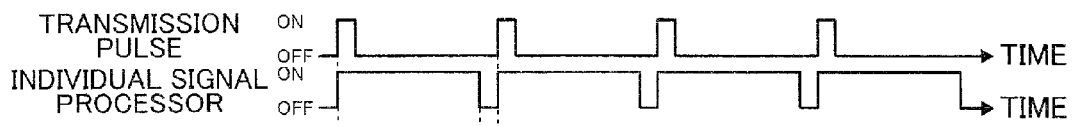
FIGS. 22A, 22B and 22C are conceptual diagrams for illustrating sound ray reduction through spatial compounding which is performed in the fourth embodiment of the ultrasound diagnostic apparatus according to the first aspect of the invention.

In the case of the depth L1, that is, when the number of sound rays is not reduced, as conceptually shown in FIG. 22A, for all the sound rays, a transmission pulse is applied while at the same time the drive of the individual signal processors 20a is activated (on), and the drive of the individual signal processors 20a is deactivated (off) when a time period corresponding to the depth L1 (depth corresponding to the composite ultrasound image) has passed.

Figure 22B:
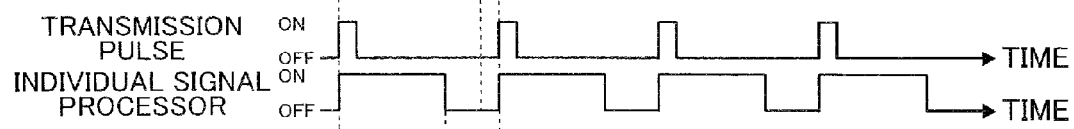

When the number of sound rays is reduced beyond the depth L2, as conceptually shown in FIG. 22B, a transmission pulse is applied while at the same time the drive of the individual signal processors 20a is activated, and the drive of the individual signal processors 20a is deactivated in the corresponding sound rays (sound rays to be eliminated beyond the predetermined depth) at a point in time when a time period corresponding to the depth L2 which is smaller than the depth L1 has passed.

That is, in the example in which one of every two sound rays is eliminated, the individual signal processors 20a alternately perform the drive shown in FIG. 22A and the drive shown in FIG. 22B on the basis of every two sound rays.

Figure 22C:
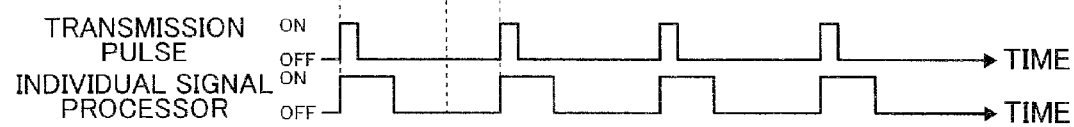

When the number of sound rays is reduced beyond the depth L3, as conceptually shown in FIG. 22C, a transmission pulse is applied while at the same time the drive of the individual signal processors 20a is activated, and the drive of the individual signal processors 20a is deactivated in the corresponding sound rays at a point in time when a time period corresponding to the smallest depth L3 which is smaller than the depth L2 has passed.

That is, in the example in which one of every two sound rays is eliminated, the individual signal processors 20a alternately perform the drive shown in FIG. 22A and the drive shown in FIG. 22C on the basis of every two sound rays.

As described above, when spatial compounding is performed in the illustrated ultrasound diagnostic apparatus 10D, as conceptually shown in FIGS. 21A and 23A to 23C, the three types of ultrasound transmission and reception for three images which are made in mutually different directions of ultrasound transmission and reception and which make up a frame unit for obtaining a composite ultrasound image are repeatedly performed on a frame basis.

For example, the transmission controller 32D and the reception controller 34D first perform the transmission and reception for the image A for obtaining the ultrasound image A as the main image as shown in FIGS. 21A and 23A to 23C.

Then, the transmission controller 32D and the reception controller 34D perform the transmission and reception for the image B for obtaining the ultrasound image B in the direction inclined by the angle of θ with respect to the direction for the ultrasound image A.

Then, the transmission controller 32D and the reception controller 34D perform the transmission and reception for the image C for obtaining the ultrasound image C in the direction inclined by the angle of −θ with respect to the direction for the ultrasound image A.

In FIGS. 23A to 23C, areas each having a black letter on a white background correspond to the ultrasound transmission and reception up to the depth L1 (normal depth), that is, the ultrasound transmission and reception for the image in which the number of sound rays is not reduced; coarsely hatched (shaded) areas correspond to the ultrasound transmission and reception for the image in which the number of sound rays is reduced beyond the depth L2 (medium depth); and densely hatched areas correspond to the ultrasound transmission and reception for the image in which the number of sound rays is reduced beyond the depth L3 (small depth).

When the temperature measurement result obtained with the temperature sensor 42 is less than T7 upon spatial compounding, the reception controller 34D of the probe 12D in the ultrasound diagnostic apparatus 10D controls the drive of the individual signal processors 20a so that the number of sound rays is not reduced in the transmission and reception for all the images A, B and C in one frame (the reception signal processing is performed up to the depth L1) as shown in FIG. 23A.

The case in which the temperature measurement result obtained with the temperature sensor 42 is less than T7 refers to the case in which the probe 12D (signal processor 20) has a steady temperature.

When the temperature measurement result obtained with the temperature sensor 42 is equal to or more than T7 but less than T8, the reception controller 34D controls the drive of the individual signal processors 20a so that, in one frame, the number of sound rays is not reduced in the transmission and reception for the image A but is reduced in the transmission and reception for the images B and C beyond the depth L2 as shown in FIG. 23B.

That is, this processing reduces the image quality of the image formed by spatial compounding in the region distant from the piezoelectric unit 16 (region beyond the depth L2).

In addition, when the temperature measurement result obtained with the temperature sensor 42 is equal to or more than T8, the reception controller 34D controls the drive of the individual signal processors 20a, so that, in one frame, the number of sound rays is not reduced in the transmission and reception for the image A but is reduced in the transmission and reception for the images B and C beyond the depth L3 as shown in FIG. 23C.

That is, this processing reduces the image quality of the image formed by spatial compounding in the region distant from the vicinity of the piezoelectric unit 16 (region beyond the depth L3).

As is clear from the above description, in cases where the temperature of the probe 12D is increased upon spatial compounding, the ultrasound diagnostic apparatus 10D of the invention reduces the number of sound rays in the regions of the ultrasound images beyond the predetermined depth by processing the reception signals in the ultrasound transmission and reception for obtaining the ultrasound images to be combined into a composite ultrasound image. That is, when the temperature of the probe 12D is increased, the ultrasound diagnostic apparatus 10D of the invention reduces the drive time of the individual signal processors 20a for processing the reception signals from the ultrasonic echoes depending on the temperature.

Therefore, according to the invention, the internal temperature of the probe 12D can be promptly reduced by stopping the signal processor 20 which is the major heat generation area even if the temperature of the probe 12D is increased during spatial compounding. Even if the temperature of the probe 12D is increased, the image quality deterioration can be minimized by promptly reducing the temperature inside the probe 12D while suppressing the temperature increase therein.

In the example shown in FIGS. 23A to 23C, the processing depth of all the reception signals is the same in one frame making up the composite ultrasound image. However, this is not the sole case of the invention and the reception signal processing depth of one or more ultrasound images each frame (each composite ultrasound image) may be different.

For example, in the example shown in FIGS. 23A to 23C, the number of sound rays is reduced in all the frames beyond the depth L3 in the transmission and reception for the images B and C when the temperature measurement result obtained with the temperature sensor 42 is equal to or more than T8. However, this is not the sole case of the invention.

Figure 24A:
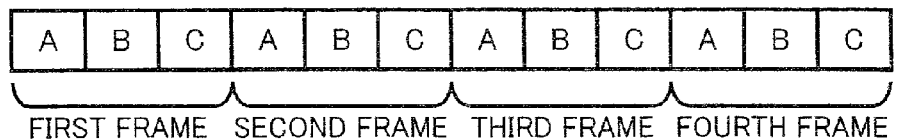
FIGS. 24A, 24B and 24C are conceptual diagrams for illustrating another example of spatial compounding which is performed in the fourth embodiment of the ultrasound diagnostic apparatus according to the first aspect of the invention.
Figure 24B:
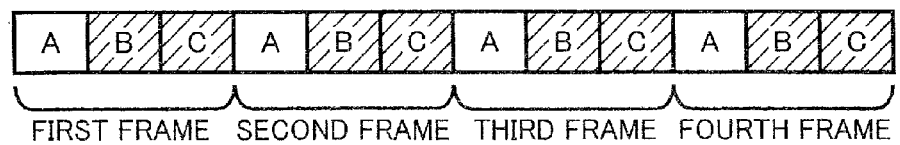

For example, as in the above case, when the temperature measurement result obtained with the temperature sensor 42 is less than T7, the number of sound rays is not reduced in the ultrasound transmission and reception for all the images as shown in FIG. 24A, and when the temperature measurement result obtained with the temperature sensor 42 is equal to or more than T7 but less than T8, the number of sound rays is not reduced in the transmission and reception for the image A but is reduced in the transmission and reception for the images B and C beyond the depth L2 as shown in FIG. 24B.

Figure 24C:
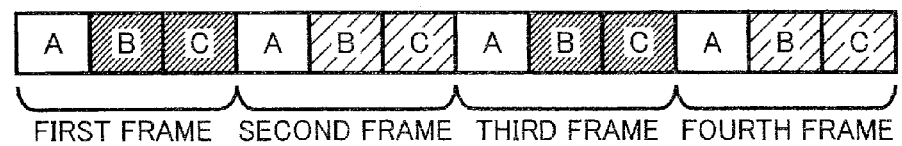

In contrast, when the temperature measurement result obtained with the temperature sensor 42 is equal to or more than T8, for example, the process may be applied in which the number of sound rays is likewise not reduced in the transmission and reception for the image A in all the frames but is reduced in each odd frame in the transmission and reception for the images B and C beyond the depth L3 and in each even frame in the transmission and reception for the images B and C beyond the depth L2 as shown in FIG. 24C.

In this example, one of every two frames can have an increased depth beyond which no sound ray is provided. Therefore, when the images produced by spatial compounding are observed as continuous images, the image quality deterioration in the section from the deeper end of the depth L3 to the deeper end of the depth L2 can be reduced compared to the example shown in FIGS. 23A to 23C.

In the above example, when the temperature measurement result obtained with the temperature sensor 42 is equal to or more than T7 but less than T8 or equal to or more than T8, the images in one frame in which the number of sound rays is reduced have no sound ray beyond the same depth. However, this is not the sole case of the invention.

In other words, reduction in the number of sound rays beyond the depth L2 and reduction in the number of sound rays beyond the depth L3 may coexist in one frame. Alternatively, non-reduction in the number of sound rays, reduction in the number of sound rays beyond the depth L2 and reduction in the number of sound rays beyond the depth L3 may coexist in one frame.

Figure 25A:
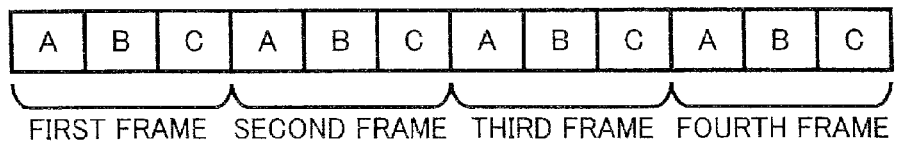
FIGS. 25A, 25B and 25C are conceptual diagrams for illustrating yet another example of spatial compounding which is performed in the fourth embodiment of the ultrasound diagnostic apparatus according to the first aspect of the invention.
Figure 25B:
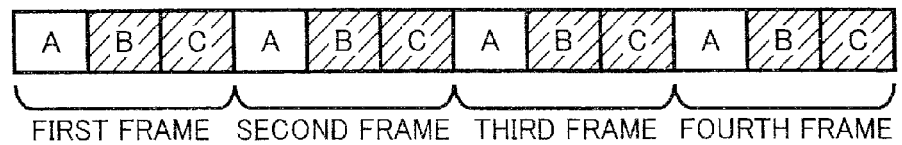
Figure 25C:
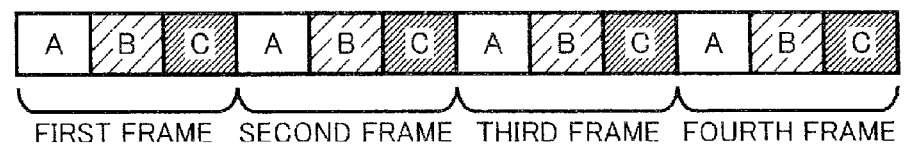

An example of the reception signal processing is conceptually shown in FIGS. 25A to 25C.

In this example, as in the above example, when the temperature measurement result obtained with the temperature sensor 42 is less than T7, the number of sound rays is not reduced in the transmission and reception for all the images A, B and C as shown in FIG. 25A. As in the above example, when the temperature measurement result obtained with the temperature sensor 42 is equal to or more than T7 but less than T8, the number of sound rays is not reduced in the transmission and reception for the image A but is reduced in the transmission and reception for the images B and C beyond the depth L2 as shown in FIG. 25B.

In contrast, in this example, when the temperature measurement result obtained with the temperature sensor 42 is equal to or more than T8, the number of sound rays is not reduced in the transmission and reception for the image A but is reduced in the transmission and reception for the images B and C beyond the depths L2 and 13, respectively, as shown in FIG. 25C. Alternatively, the depth of the images A, B and C may be set to L1, L3 and L2, respectively.

Compared to the example shown in FIGS. 23A to 23C, this example reduces the effect of preventing heat generation but is advantageous in terms of the image quality of the composite ultrasound images.

In this example, when the temperature measurement result obtained with the temperature sensor 42 is equal to or more than T8, reduction in the number of sound rays beyond the depth L2 and reduction in the number of sound rays beyond the depth L3 may be alternately performed for the images B and C.

Figure 26A:
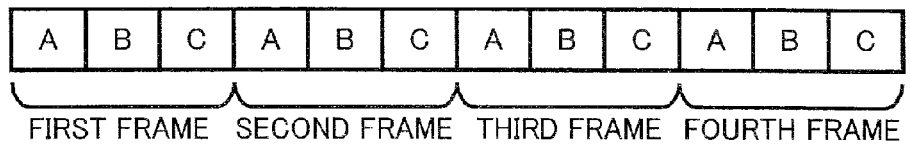
FIGS. 26A, 26B and 26C are conceptual diagrams for illustrating still another example of spatial compounding which is performed in the fourth embodiment of the ultrasound diagnostic apparatus according to the first aspect of the invention.
Figure 26B:
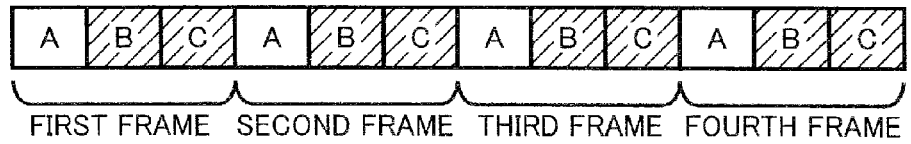

For example, as in the above example, when the temperature measurement result obtained with the temperature sensor 42 is less than T7, the number of sound rays is not reduced in the ultrasound transmission and reception for all the images as shown in FIG. 26A, and when the temperature measurement result is equal to or more than T7 but less than T8, the number of sound rays is not reduced in the transmission and reception for the image A but is reduced in the transmission and reception for the images B and C beyond the depth L2 as shown in FIG. 26B.

Figure 26C:
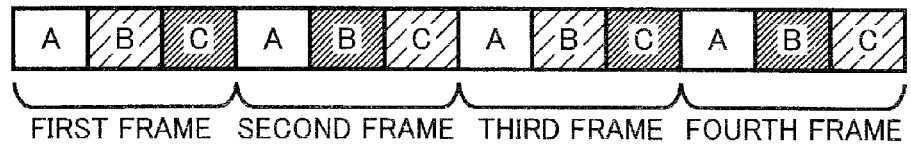

In contrast, when the temperature measurement result obtained with the temperature sensor 42 is equal to or more than T8, for example, the process may be applied in which the number of sound rays is likewise not reduced in the transmission and reception for the image A in all the frames but is reduced in each odd frame in the transmission and reception for the images B and C beyond the depths L2 and L3, respectively, and in each even frame in the transmission and reception for the images B and C beyond the depths L3 and L2, respectively, as shown in FIG. 26C.

In this example, the region beyond the depth L3 where the number of sound rays is reduced is repeated in the ultrasound images to be combined by spatial compounding on the basis of every two frames. Therefore, any region where the image quality is continuously deteriorated can be eliminated from the composite ultrasound images to suppress the image quality, deterioration when the images produced by spatial compounding are observed as continuous images.

In the above example, when the temperature in the probe 12D is increased, the transmission and reception for the image B and/or those for the image C are performed by reducing the number of sound rays in the region beyond the predetermined depth but this is not the sole case of the invention. That is, the transmission and reception for the image A may be performed by reducing the number of sound rays in the region beyond the predetermined depth depending on the temperature increase.

However, the ultrasound image A is the main image. In other words, the composite ultrasound image produced in the diagnostic apparatus body 14D through spatial compounding is the image having the region of the ultrasound image A (derived from the transmission and reception for the image A). Therefore, when the ultrasound transmission and reception which does not involve the reduction in the number of sound rays is included in one frame, it is more advantageous to perform the transmission and reception for the image A serving as the main image without reducing the number of sound rays because a proper composite ultrasound image can be consistently obtained.

In the above example, the number of sound rays is not reduced up to the depth L1 in at least one image (the transmission and reception for the image A) at any temperature. However, this is not the sole case of the invention and the number of sound rays may be performed beyond the depth L2 or L3 in the ultrasound transmission and reception for all the images depending on the temperature.

Figure 27A:
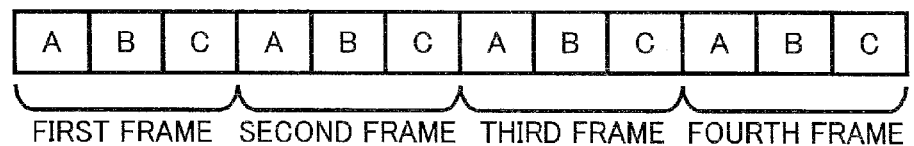
FIGS. 27A, 27B and 27C are conceptual diagrams for illustrating still yet another example of spatial compounding which is performed in the fourth embodiment of the ultrasound diagnostic apparatus according to the first aspect of the invention.
Figure 27B:
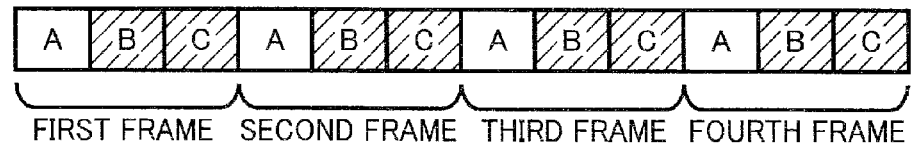
Figure 27C:
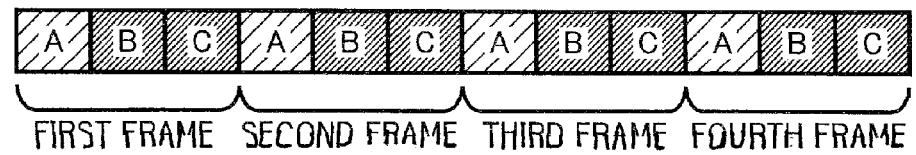

An example of the ultrasound transmission and reception is conceptually shown in FIGS. 27A to 27C.

In this example, as in the above example, when the temperature measurement result obtained with the temperature sensor 42 is less than T7, the number of sound rays is not reduced in the transmission and reception for all the images A, B and C as shown in FIG. 27A. As in the above example, when the temperature measurement result obtained with the temperature sensor 42 is equal to or more than T7 but less than T8, the number of sound rays is not reduced in the transmission and reception for the image A but is reduced in the transmission and reception for the images B and C beyond the depth L2 as shown in FIG. 27B.

In contrast, in this example, when the temperature measurement result obtained with the temperature sensor 42 is equal to or more than T8, the number of sound rays is reduced in the transmission and reception for the image A beyond the depth L2 and in the transmission and reception for the images B and C beyond the depth L3 as shown in FIG. 27C.

According to this example, the image quality of the resulting composite ultrasound image is reduced as s whole but the effect of preventing heat generation is increased.

In the above example, when the temperature measurement result obtained with the temperature sensor 42 is equal to or more than T7, the number of sound rays is reduced in the region deeper than the predetermined depth in the ultrasound transmission and reception for two images in one frame but this is not the sole case of the invention. That is, based on the temperature measurement result obtained with the temperature sensor 42, the number of sound rays may be reduced beyond the predetermined depth in the ultrasound transmission and reception for only one image in one frame or in the ultrasound transmission and reception for three or more images in one frame.

Considering the purpose that the temperature increase within the probe 12D is suppressed while minimizing the image quality deterioration due to the temperature increase, when the temperature exceeds one of the thresholds, the number of sound rays is preferably reduced beyond the predetermined depth in two or more images of one frame. In addition, in order to suppress the temperature increase while preventing the image quality deterioration, when the temperature exceeds one of the thresholds, the number of sound rays for all the images except the image A (main image) is preferably reduced in the region beyond the predetermined depth depending on the temperature.

In addition, in the above examples, since the predetermined number upon spatial compounding is three, two temperature thresholds are provided. However, this is not the sole case of the invention and in cases were the predetermined number is four or more, three or more thresholds may be provided.

The number of depths set for the reception signal processing depending on the temperature is also not limited to three. For example, two depths including the normal depth (L1) and the small depth (L3) may be provided. Alternatively, four or more depths of reception signal processing may be provided by setting a plurality of medium depths such as the depth L2-1 and the depth L2-2 between the normal depth L1 and the small depth L3.

In the examples shown in FIGS. 23A to 27C, the order of ultrasound transmission and reception in one frame is the same for all the frames. However, this is not the sole case of the invention and the order of ultrasound transmission and reception of the images in each frame may be different.

Figure 28A:
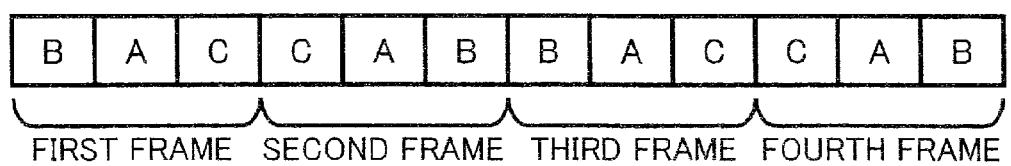
FIGS. 28A, 28B and 28C are conceptual diagrams for illustrating a further example of spatial compounding which is performed in the fourth embodiment of the ultrasound diagnostic apparatus according to the first aspect of the invention.
Figure 28B:
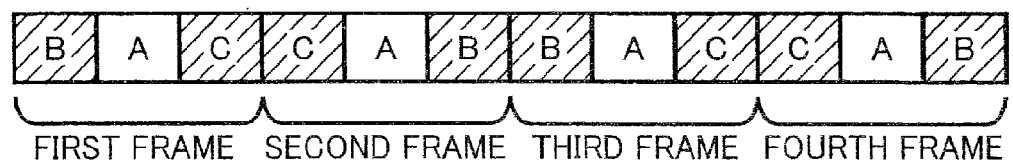
Figure 28C:
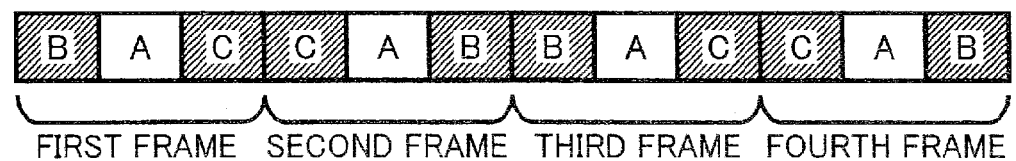

For example, as shown in FIGS. 28A to 28C, the ultrasound transmission and reception of the first frame, the second frame, the third frame, the fourth frame and the like may be performed in the orders of "image B→image A→image C", "image C→image A→image B", "image B→image A→image C" and "image C→image A→image B" and the like, respectively.

That is, also in the fourth embodiment of the ultrasound diagnostic apparatus 10D, as in the first embodiment, the directions of ultrasound transmission and reception in the last ultrasound image in the earlier one of two consecutive frames (i.e., two temporally consecutive composite ultrasound images) and the first ultrasound image in the subsequent frame may be the same.

This order of ultrasound transmission and reception enables the ultrasound transmission and reception to be continued in the same directions to facilitate the control of the transmission drive 30 and the individual signal processors 20a.

As described above, the reception signals outputted from the probe 12D are supplied to the diagnostic apparatus body 14D by wireless communication.

Similarly to the first embodiment of the diagnostic apparatus body 10A shown in FIG. 1, the diagnostic apparatus body 14D includes an antenna 50, a wireless communication unit 52, a serial/parallel converter 54, a data storage unit 56, an image generating unit 58, a display controller 62, a monitor 64, a communication controller 68, an apparatus body controller 70 and an operating unit 72.

As in the above embodiment, the diagnostic apparatus body 14D includes a built-in power supply unit (not shown), which supplies electric power for drive to each component.

The antenna 50, the wireless communication unit 52, the serial/parallel converter 54, the data storage unit 56, the image generating unit 58, the display controller 62, the monitor 64, the communication controller 68 and the apparatus body controller 70 are basically the same as those in the diagnostic apparatus body 10A shown in FIG. 1.

More specifically, the wireless communication unit 52 performs wireless communication with the probe 12D via the antenna 50 to transmit control signals to the probe 12D and receive signals sent from the probe 12D. The wireless communication unit 52 demodulates the received signals and outputs them to the serial/parallel converter 54 as serial sample data.

The communication controller 68 controls the wireless communication unit 52 so that various control signals are transmitted according to the settings made by the apparatus body controller 70.

The serial/parallel converter 54 converts the serial sample data into parallel sample data. The data storage unit 56 stores at least one frame of sample data converted by the serial/parallel converter 54.

The image generating unit 58 (phase adjusting and summing unit 76D, image processor 78 and image combining unit 80) performs reception focusing on sample data for each image read out from the data storage unit 56 to generate image signals representing an ultrasound image.

As described above, when spatial compounding is performed in the ultrasound diagnostic apparatus 10D, the probe 12D performs, for example, the ultrasound transmission and reception for three images, that is, the transmission and reception for the images A, B and C.

When spatial compounding is performed, the image combining unit 80 of the image generating unit 58 accordingly combines the ultrasound image A derived from the transmission and reception for the image A, the ultrasound image B derived from the transmission and reception for the image B, and the ultrasound image C derived from the transmission and reception for the image C to generate image signals for a composite ultrasound image.

As described above, when spatial compounding is performed in the ultrasound diagnostic apparatus 10D, the probe 12D reduces the number of sound rays in the region beyond the predetermined depth as for the reception of the ultrasonic echoes based on the temperature measured with the temperature sensor 42. That is, the number of sound rays is reduced in the region of the ultrasound image beyond the predetermined depth based on the temperature measured with the temperature sensor 42.

Upon spatial compounding, the phase adjusting and summing unit 76D interpolates the eliminated sound rays with the adjacent sound rays (surrounding sound rays) as to the ultrasound image in which the number of sound rays is reduced in the region beyond the predetermined depth to generate sound rays corresponding to those of the region where the number of sound rays was reduced, thus generating sound rays (sound ray signals) for the whole ultrasound image.

The interpolation method is not particularly limited but any known interpolation method implemented in various image processing steps can all be used.

The display controller 62 causes the monitor 64 to display the ultrasound image according to the image signals generated by the image generating unit 58.

Under the control of the display controller 62, the monitor 64 displays the ultrasound image.

The apparatus body controller 70 controls the components in the diagnostic apparatus body 14D. The apparatus body controller 70 is connected to the operating unit 72 to perform various input operations including as to whether or not spatial compounding is to be performed.

The operation of the ultrasound diagnostic apparatus 10D shown in FIG. 20 is described below.

Similarly to the ultrasound diagnostic apparatus 10A, during the diagnosis, various kinds of information inputted to the operating unit 72 are first sent to the probe 12D by wireless communication and then supplied to the probe controller 38 also in the ultrasound diagnostic apparatus 10D.

Then, ultrasonic waves are transmitted from the transducers 18 in accordance with the drive voltage supplied from the transmission drive 30 of the probe 12D.

The reception signals outputted from the transducers 18 that have received the ultrasonic echoes generated by reflection of the ultrasonic waves on the subject are supplied to the corresponding individual signal processors 20a to generate sample data.

In the probe 12D, when spatial compounding is performed, the temperature measurement result of the signal processor 20 obtained with the temperature sensor 42 is sent to the reception controller 34D.

As described above, when spatial compounding is performed in the ultrasound diagnostic apparatus 10D, the probe 12D reduces the number of sound rays in the regions of the ultrasound images beyond the predetermined depth based on the temperature measurement results of the reception signal processor 20 obtained with the temperature sensor 42. More specifically, the probe 12D controls the drive of the individual signal processors 20a processing the reception signals such that the depth beyond which the number of sound rays is reduced in any of the ultrasound images to be combined is decreased in the order of "depth L1→depth L2→depth L3" each time the temperature exceeds one of the thresholds according to the temperature measurement results obtained with the temperature sensor 42.

For example, when the temperature measured with the temperature sensor 42 is less than T7, the reception controller 34D controls the operation of the signal processor 20 (individual signal processors 20a) so that the number of sound rays is not reduced in the transmission and reception for all the images A, B and C as shown in 23A.

When the temperature measured with the temperature sensor 42 is equal to or more than T7 but less than T8, the reception controller 34D controls the operation of the signal processor 20 so that the number of sound rays is not reduced in the transmission and reception for the image A but is reduced in the transmission and reception for the images B and C beyond the depth L2 in one of every two frames as shown in FIG. 23B.

When the temperature measured with the temperature sensor 42 is equal to or more than T8, the reception controller 34D controls the operation of the signal processor 20 so that the number of sound rays is not reduced in the transmission and reception for the image A but is reduced in the transmission and reception for the images B and C beyond the depth L3 in one of every two frames as shown in FIG. 23C.

The sample data generated by the individual signal processors 20a are sent to the parallel/serial converter 24, where the sample data is converted into serial data. The serial data is then wirelessly transmitted from the wireless communication unit 26 (antenna 28) to the diagnostic apparatus body 14D.

The sample data received by the wireless communication unit 52 of the diagnostic apparatus body 14D converted into parallel data in the serial/parallel converter 54 and stored in the data storage unit 56.

Further, the sample data for each image is read out from the data storage unit 56 to generate image signals of an ultrasound image in the image generating unit 58. The display controller 62 causes the monitor 64 to display the ultrasound image based on the image signals.

Upon spatial compounding, the phase adjusting and summing unit 76D of the image generating unit 58 interpolates the sound rays eliminated by the probe 12D and then the image combining unit 80 combines the ultrasound images.

As described above, when spatial compounding is performed in the ultrasound diagnostic apparatus 10D, the probe 12D reduces the number of sound rays in the ultrasound images to be combined beyond the predetermined depth based on the temperature measurement results of the reception processor 20 obtained with the temperature sensor 42. More specifically, the probe 12D reduces the number of sound rays in any of the ultrasound images to be combined beyond the depth L2 or 13 based on the temperature measurement result obtained with the temperature sensor 42.

For example, in the example shown in FIGS. 23A to 23C, when the temperature is less than T7 upon spatial compounding, the probe 12D does not reduce the number of sound rays in the ultrasound transmission and reception based on the temperature measurement result obtained with the temperature sensor 42. When the temperature measured with the temperature sensor 42 is equal to or more than T7 but less than T8, the number of sound rays is reduced in the region beyond the depth L2 in one of every two frames. In addition, when the temperature measured with the temperature sensor 42 is equal to or more than T8, the number of sound rays is reduced in the region beyond the depth L3 in one of every two frames.

When spatial compounding is performed, the phase adjusting and summing unit 76D correspondingly interpolates the eliminated sound rays (the portions having no sound rays) with the surrounding sound rays as for the image for which the number of sound rays is reduced in the region beyond the depth L2 or L3 to thereby generate sound rays corresponding to the whole area of one ultrasound image and sends the produced sound rays to the image combining unit 80.

When spatial compounding is performed, the image combining unit 80 combines the ultrasound image A derived from the transmission and reception for the image A, the ultrasound image B derived from the transmission and reception for the image B, and the ultrasound image C derived from the transmission and reception for the image C which were generated in the phase adjusting and summing unit 76D to thereby generate image signals for a composite ultrasound image, and outputs the image signals to the display controller 62.

Figure 29:
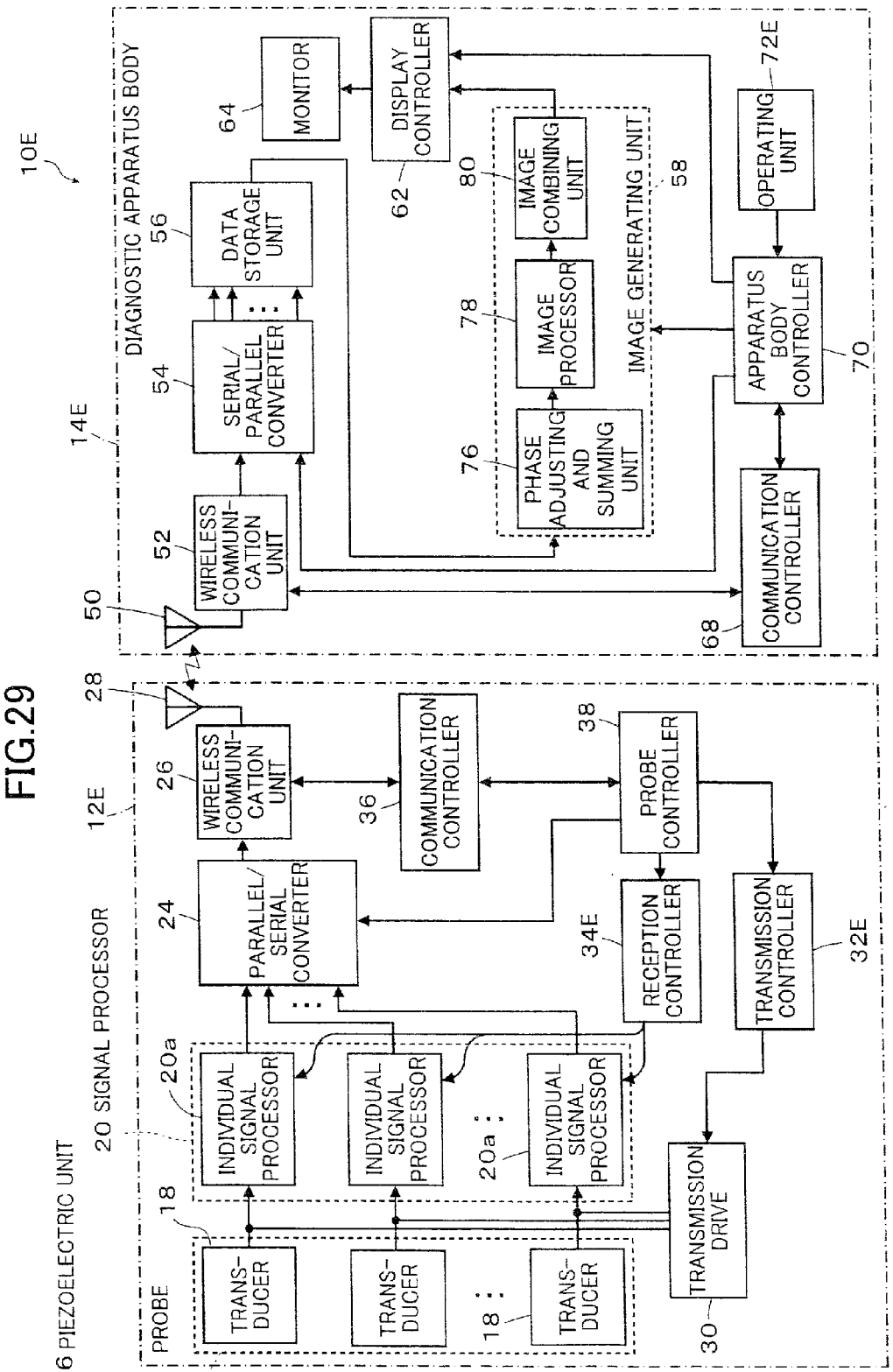
FIG. 29 is a conceptual block diagram showing the ultrasound diagnostic apparatus according to the second aspect of the invention.

FIG. 29 is a conceptual block diagram showing an embodiment of the ultrasound diagnostic apparatus according to the second aspect of the invention.

Many components of the ultrasound diagnostic apparatus 10E shown in FIG. 29 are the same as those of the ultrasound diagnostic apparatus 10A shown in FIG. 1 except that the temperature sensor 42 is not provided. Therefore, like components are denoted by the same reference numerals and the following description mainly focuses on the different features.

As in the first embodiment of the ultrasound diagnostic apparatus 10A, the ultrasound diagnostic apparatus 10E shown in FIG. 29 includes an ultrasound probe 12E (hereinafter referred to as "probe 12E") and a diagnostic apparatus body 14E. As in the above embodiment, the ultrasound probe 12E is connected to the diagnostic apparatus body 14E by wireless communication.

As in the first embodiment of the probe 12A, the probe 12E transmits ultrasonic waves to the subject, receives ultrasonic echoes generated by reflection of the ultrasound waves on the subject, and outputs reception signals of an ultrasound image in accordance with the received ultrasonic echoes.

There is no limitation on the type of the probe 12E and various known ultrasound probes can be used.

As in the probe 12A, the probe 12E also includes a piezoelectric unit 16, a signal processor 20, a parallel/serial converter 24, a wireless communication unit 26, an antenna 28, a transmission drive 30, a transmission controller 32E, a reception controller 34E, a communication controller 36 and a probe controller 38. As described above, the probe 12E in this aspect includes no temperature sensor.

The probe 12E also includes a built-in battery (not shown), which supplies electric power for drive to each component.

The piezoelectric unit 16, the signal processor 20, the parallel/serial converter 24, the wireless communication unit 26, the antenna 28, the transmission drive 30, the communication controller 36 and the probe controller 38 are basically the same as those of the probe 12A.

More specifically, the piezoelectric unit 16 is a one-dimensional or two-dimensional array of transducers 18 transmitting and receiving ultrasonic waves.

The transmission drive 30 supplies the transducers 18 with a drive voltage so that the transducers transmit ultrasonic waves so as to form ultrasonic beams.

The transducers 18 output the reception signals of the ultrasonic echoes to individual signal processors 20a of the signal processor 20. As described above, each individual signal processor 20a has an AFE, processes the reception signals to generate sample data and supplies the generated sample data to the parallel/serial converter 24. The parallel/serial converter 24 converts the parallel sample data into serial sample data.

The ultrasound diagnostic apparatus 10E also has the function of spatial compounding in which ultrasound images obtained by the ultrasound transmission and reception in mutually different directions are combined to produce a composite ultrasound image.

Similarly to the above ultrasound diagnostic apparatus 10A, the ultrasound diagnostic apparatus 10E combines, for example, three ultrasound images upon spatial compounding. Therefore, the transmission controller 32E and the reception controller 34E control the drive of the transmission drive 30 and the individual signal processors 20a, respectively, such that three types of ultrasound transmission and reception are performed in mutually different directions of ultrasound transmission and reception.

When spatial compounding is performed, the transmission controller 32E and the reception controller 34E of the probe 12E control the drive of the transmission drive 30 and the individual signal processors 20a, respectively, such that the plurality of types of ultrasound transmission and reception are performed in a predetermined order.

When spatial compounding is performed in the ultrasound diagnostic apparatus 10E according to this aspect, the probe 12E makes the directions of ultrasound transmission and reception in the last ultrasound image in the earlier one of two temporally consecutive frames (composite ultrasound images) coincide with those in the first ultrasound image in its subsequent frame. In other words, the last ultrasound image in the earlier one of two temporally consecutive composite ultrasound images is made to coincide with the first ultrasound image in its subsequent composite ultrasound image in the directions of ultrasound transmission and reception.

This point will be described in detail later.

The wireless communication unit 26 generates transmission signals from the serial sample data and transmits the serial sample data to the diagnostic apparatus body 14E via the antenna 28.

The wireless communication unit 26 receives various control signals from the diagnostic apparatus body 14E and outputs the received control signals to the communication controller 36.

The communication controller 36 controls the wireless communication unit 26. The communication controller 36 outputs the various control signals received by the wireless communication unit 26 to the probe controller 38.

The probe controller 38 controls various components of the probe 12E according to various control signals transmitted from the diagnostic apparatus body 14E.

As described above, the ultrasound diagnostic apparatus 10E of the invention has the function of producing an image (composite ultrasound image) through spatial compounding.

As in the ultrasound diagnostic apparatus 10A shown in FIG. 1, the ultrasound diagnostic apparatus 10E also performs, for example, the three types of ultrasound transmission and reception in mutually different directions upon spatial compounding as conceptually shown in FIG. 2. More specifically, upon spatial compounding, the probe 12E performs the three types of ultrasound transmission and reception, including the "transmission and reception for the image A" as the ultrasound transmission and reception for obtaining the main image (image including the whole area of the composite ultrasound image formed by spatial compounding), the "transmission and reception for the image B" in a direction inclined by an angle of θ with respect to the direction of the transmission and reception for the image A, and the "transmission and reception for the image C" in a direction inclined by an angle of −θ with respect to the direction of the transmission and reception for the image A.

The diagnostic apparatus body 14E (more specifically an image combining unit 80 to be described later) combines one to three ultrasound images selected from the ultrasound image A (solid line) as the main image obtained by the transmission and reception for the image A, the ultrasound image B (broken line) obtained by the transmission and reception for the image B, and the ultrasound image C (chain line) obtained by the transmission and reception for the image C according to the number of types of ultrasound transmission and reception performed in each frame to thereby produce a composite ultrasound image covering the region of the ultrasound image A.

When spatial compounding is performed in the ultrasound diagnostic apparatus 10E, for example, a predetermined number of one to three) types of ultrasound transmission and reception which are selected from the three types including the transmission and reception for the image A, those for the image B and those for the image C and which make up a frame unit for obtaining a composite ultrasound image are repeatedly performed on a frame basis.

As will be described later in detail, in the second aspect of the invention, the number of types of ultrasound transmission and reception in each frame upon spatial compounding may be the same in all the frames or a frame having a different number of types of ultrasound transmission and reception may be included. That is, when spatial compounding is performed in the ultrasound diagnostic apparatus 10E, the number of ultrasound images to be combined may be the same for all the composite ultrasound images or composite ultrasound images made from different numbers of ultrasound images may coexist.

In the practice of the invention, the number of types of ultrasound transmission and reception set to perform spatial compounding, that is, the maximum number of ultrasound images to be combined is not limited to three. That is, the maximum number of ultrasound images to be combined by spatial compounding may be two or four or more.

In addition, various known methods can be used to transmit and receive ultrasonic waves in different directions as in the above embodiments.

As described above, when spatial compounding is performed, the plurality of types of ultrasound transmission and reception which are made in mutually different directions of ultrasound transmission and reception and which make up a frame are repeatedly performed on a frame basis.

In normal spatial compounding, the plurality of types of ultrasound transmission and reception which are different in the directions of ultrasound transmission and reception are performed in each frame in the same order. More specifically, when the transmission and reception for the images A, B and C are performed as in the illustrated example, as conceptually shown in FIG. 30C, the ultrasound transmission and reception are repeatedly performed on a frame basis in the order of the transmission and reception for the image A, those for the image B and those for the image C which make up one frame. Therefore, in normal spatial compounding, the directions of ultrasound transmission and reception are to be changed each time the transmission and reception for each image are performed.

In contrast, when spatial compounding is performed in the ultrasound diagnostic apparatus 10E, the probe 12E makes the directions of ultrasound transmission and reception in the last ultrasound image in the earlier one of two temporally consecutive frames (composite ultrasound images) coincide with those in the first ultrasound image in its subsequent frame. In other words, the last ultrasound image in the earlier one of two temporally consecutive composite ultrasound images is made to coincide with the first ultrasound image in its subsequent composite ultrasound image in the directions of ultrasound transmission and reception.

In other words, in the ultrasound diagnostic apparatus 10E of the invention, the last ultrasound transmission and reception in the earlier one of two temporally consecutive frames is made to coincide with the first ultrasound transmission and reception in its subsequent frame in the directions of ultrasound transmission and reception.

Figure 30A:
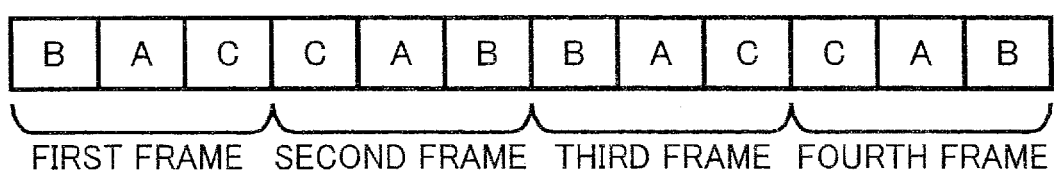
FIGS. 30A and 30B are conceptual diagrams for illustrating an example of spatial compounding which is performed in the ultrasound diagnostic apparatus according to the second aspect of the invention.

For example, as conceptually shown in FIG. 30A, the ultrasound transmission and reception of the first frame, the second frame, the third frame, the fourth frame and the like are performed in the orders of "image B→image A→image C", "image C→image A→image B", "image B→image A→image C" (in the same order as the first frame), "image C→image A→image B" the same order as the second frame) and the like, respectively. In other words, the ultrasound transmission and reception in the order of "image B→image A→image C" and those in the order of "image C→image A→image B" are alternately repeated.

Figure 30B:
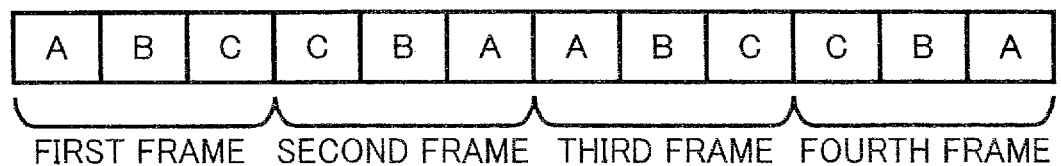

Alternatively, as conceptually shown in FIG. 30B, the ultrasound transmission and reception of the first frame, the second frame, the third frame, the fourth frame and the like are performed in the orders of "image A→image B→image C", "image C→image B→image A", "image A→image B→image C" (in the same order as the first frame), "image C→image B→image A" (in the same order as the second frame) and the like, respectively. In other words, the ultrasound transmission and reception in the order of "image A→image B→image C" and those in the order of "image C→image B→image A" are alternately repeated.

In this aspect, when spatial compounding is thus performed, the last image in the earlier one of two temporally consecutive frames is made to coincide with the first image in its subsequent frame in the directions of ultrasound transmission and reception. In other words, the last ultrasound image in the earlier one of two temporally adjacent composite ultrasound images produced by spatial compounding and the first ultrasound image in the subsequent composite ultrasound image are obtained by the ultrasound transmission and reception in the same directions.

Therefore, it is not necessary to change the directions of ultrasound transmission and reception between two adjacent frames, which can simplify the control of the ultrasound transmission and reception in the transmission drive 30 and the individual signal-processors 20a, for example when changing the control of the delay for changing the directions of ultrasound transmission and reception. Accordingly, the illustrated ultrasound diagnostic apparatus 10E can reduce the burden of the probe 12E in spatial compounding.

Spatial compounding performed in the ultrasound diagnostic apparatus 10E is not limited to the case where all the set types of ultrasound transmission and reception are performed in one frame. That is, in this aspect, one frame of ultrasound images may be formed by any number of types of ultrasound transmission and reception if the number is equal to or smaller than the appropriately set predetermined number.

In other words, this aspect is not limited to the case where the set maximum number of ultrasound images are combined by spatial compounding.

When spatial compounding is performed in the ultrasound diagnostic apparatus 10E, the number of types of ultrasound transmission and reception in one frame is not limited to three but may be two if the directions of ultrasound transmission and reception in the last ultrasound image in one of two adjacent frames may coincide with those in the first ultrasound image in its subsequent frame. That is, the number of ultrasound images to be combined in one frame by spatial compounding may be two.

For example, high image quality mode in which three images are combined and normal image quality mode in which two images are combined are set as spatial compounding modes so that one of three-image composition and two-image composition may be selected with an operating unit 72E to be described later by any known method such as the GUI (graphical user interface). Alternatively, the probe 12E may be provided with a selection means such as a switch. These modes are also applied to the cases shown in FIGS. 32A to 33B to be described later.

Figure 31A:
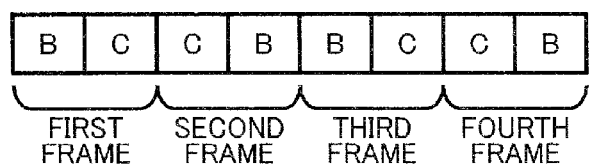
FIGS. 31A and 31B are conceptual diagrams for illustrating another example of spatial compounding which is performed in the ultrasound diagnostic apparatus according to the second aspect of the invention.

For example, as conceptually shown in FIG. 31A, the transmission and reception for the image A (main image) are not performed and the ultrasound transmission and reception of the first frame, the second frame, the third frame, the fourth frame and the like may be performed in the orders of "image B→image C", "image C→image B", "image B→image C" (in the same order as the first frame), "image C→image B" (in the same order as the second frame) and the like, respectively. In other words, the ultrasound transmission and reception in the order of "image B→image C" and those in the order of "image C→image B" may be alternately repeated.

When two ultrasound images are used to perform spatial compounding in the ultrasound diagnostic apparatus 10E, frames may coexist in which combinations of types of ultrasound transmission and reception are different.

That is, when the number of types of ultrasound transmission and reception used to perform special compounding is smaller than the set number, frames may coexist in which combinations of types of ultrasound transmission and reception are different. In other words, when the number of ultrasound images to be combined by spatial compounding is smaller than the set maximum number, composite ultrasound images obtained by combining ultrasound images which are different in the directions of ultrasound transmission and reception may coexist.

Figure 31B:
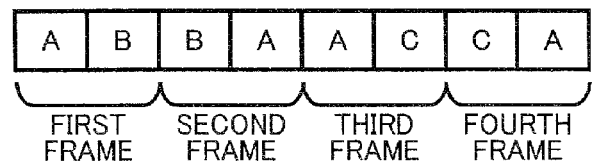

For example, as conceptually shown in FIG. 31B, the ultrasound transmission and reception of the first frame, the second frame, the third frame and the fourth frame may be performed in the orders of "image A→image B", "image B→image A", "image A→image C" and "image C→image A", respectively, and those of the first to fourth frames may be repeatedly performed.

In the practice of the invention, if the directions of the ultrasound transmission and reception in temporally adjacent frames coincide with each other when spatial compounding is performed, frames which are different in the number of types of ultrasound transmission and reception (the number of ultrasound images to be combined) may coexist in the predetermined number of temporally consecutive frames.

That is, in the practice of the invention, frames which are different in the frame rate in spatial compounding may coexist.

Figure 32A:
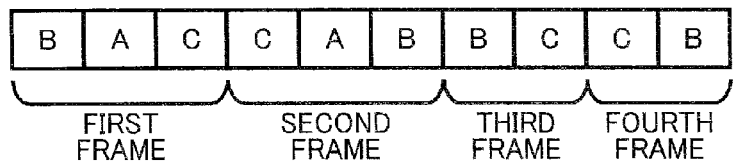
FIGS. 32A and 32B are conceptual diagrams for illustrating yet another example of spatial compounding which is performed in the ultrasound diagnostic apparatus according to the second aspect of the invention.

For example, as conceptually shown in FIG. 32A, the ultrasound transmission and reception of the first and second frames may be performed in the orders of "image B→image A→image C" and "image C→image A→image B", respectively, and those of the third and fourth frames be performed so as to form two images such as "image B→image C" and "image C→image B", respectively, and those of the first to fourth frames be repeatedly performed.

Figure 32B:
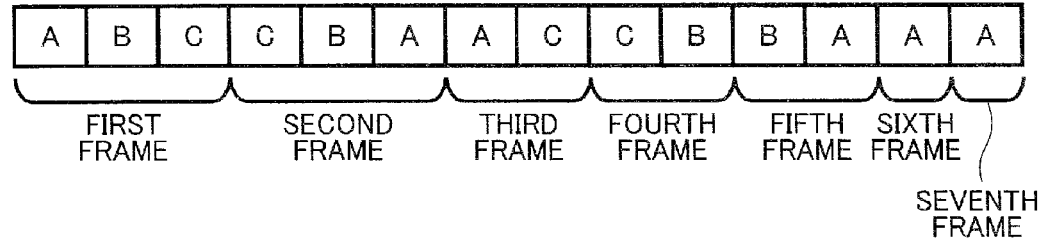

Alternatively, as conceptually shown in FIG. 32B, the ultrasound transmission and reception of the first and second frames may be performed in the orders of "image A→image B→image C" and "image C→image B→image A", respectively, and those of the third, fourth and fifth frames be performed so as to form two images such as "image A→image C", "image C→image B" and "image B→image A", respectively, those of the sixth and seventh frames be performed so as not to perform image composition or to form only one image, that is, image A, and those of the first to seventh frames be repeatedly performed.

The predetermined number of temporally consecutive frames is not limited to four and seven as in the above cases but may be five, six or eight or more. The transmission and reception for the image A serving as the main image are preferably performed for the frames in which one type of ultrasound transmission and reception is only performed.

In addition, in the ultrasound diagnostic apparatus 10E according to this aspect, the ultrasound transmission and reception may be shared between the last ultrasound image in the earlier one of two temporally adjacent frames and the first ultrasound image in the subsequent frame so that the directions of ultrasound transmission and reception in the last ultrasound image may coincide with those in the first ultrasound image.

In other words, in two temporally adjacent composite ultrasound images, one ultrasound image may serve as both of the last ultrasound image in the earlier composite ultrasound image and the first ultrasound image the subsequent composite ultrasound image.

For example when spatial compounding is performed according to the example shown in FIG. 32A, as conceptually shown in FIG. 33A, the pattern of ultrasound transmission and reception of "image B→image A→image C→image A→image B→image C→image B" is repeatedly performed.

The first three images of "image B→image A→image C" are used as the first frame. The image C is shared between the last image in the first frame and the first image in the second frame and the three images starting from the third image C: "image C→image A→image B" are used as the second frame. The image B is shared between the last image in the second frame and the first image in the third frame and the two images starting from the fifth image B: "image B→image C" are used as the third frame. In addition, The image C is shared between the last image in the third frame and the first image in the fourth frame and the two images starting from the sixth image C: "image C→image B" are used as the fourth frame, and the ultrasound transmission and reception of the first to fourth frames are repeatedly performed.

In this case, the image B may be shared between the last image in the fourth frame and the first image in the first frame.

When spatial compounding is performed according to the example shown in FIG. 32B, as conceptually shown in FIG. 33B, the pattern of ultrasound transmission and reception of "image A→image B→image C→image B→image A→image C→image B→image A→image A→image A" is repeatedly performed.

The first three images of "image A→image B→image C" are used as the first frame. The image C is shared between the last image in the first frame and the first image in the second frame and the three images starting from the third image C: "image C→image B→image A" are used as the second frame. The image A is shared between the last image in the second frame and the first image in the third frame and the two ages starting from the fifth image A: "image A→image C" are used as the third frame. The image C is shared between the last image in the third frame and the first image in the fourth frame and the two images starting from the sixth image C: "image C→image B" are used as the fourth frame. The image B is shared between the last image in the fourth frame and the first image in the fifth frame and the two images starting from the seventh image B: "image B→image A" are used as the fifth frame. In addition, the image A as the ninth image and the image A as the tenth image are used as the sixth frame and seventh frame, respectively, and the ultrasound transmission and reception of the first to seventh frames are repeatedly performed.

In this case, the image A may be shared between the image in the seventh frame and the first image in the first frame.

By thus sharing the ultrasound transmission and reception (ultrasound images to be used for composition) between adjacent frames, the composite ultrasound images can be produced by spatial compounding at higher speeds.

As described above, the reception signals outputted from the probe 12E are supplied to the diagnostic apparatus body 14E by wireless communication.

Similarly to the first embodiment of the diagnostic apparatus body 10A shown in FIG. 1, the diagnostic apparatus body 14E includes an antenna 50, a wireless communication unit 52, a serial/parallel converter 54, a data storage unit 56, an image generating unit 58, a display controller 62, a monitor 64, a communication controller 68, an apparatus body controller 70 and the operating unit 72E.

As in the above embodiment, the diagnostic apparatus body 14E includes a built-in power supply unit (not shown), which supplies electric power for drive to each component.

The antenna 50, the wireless communication unit 52, the serial/parallel converter 54, the data storage unit 56, the image generating unit 58, the display controller 62, the monitor 64, the communication controller 68 and the apparatus body controller 70 are basically the same as those in the diagnostic apparatus body 10A shown in FIG. 1.

More specifically, the wireless communication unit 52 performs wireless communication with the probe 12E via the antenna 50 to transmit control signals to the probe 12E and receive signals sent from the probe 12E. The wireless communication unit 52 demodulates the received signals and outputs them to the serial/parallel converter 54 as serial sample data.

The communication controller 68 controls the wireless communication unit 52 so that various control signals are transmitted according to the settings made by the apparatus body controller 70.

The serial/parallel converter 54 converts the serial sample data into parallel sample data. The data storage unit 56 stores at least one frame of sample data converted by the serial/parallel converter 54.

The image generating unit 58 (phase adjusting and summing unit 76, image processor 78 and image combining unit 80) performs reception focusing on sample data for each image read out from the data storage unit 56 to generate image signals representing an ultrasound image.

As described above, when spatial compounding is performed in the ultrasound diagnostic apparatus 10E, the probe 12E performs, for example, the ultrasound transmission and reception for three images, that is, the transmission and reception for the images A, B and C.

When spatial compounding is performed, the image combining unit 80 of the image generating unit 58 accordingly combines the ultrasound image A derived from the transmission and reception for the image A, the ultrasound image B derived from the transmission and reception for the image B, and the ultrasound image C derived from the transmission and reception for the image C to generate image signals for a composite ultrasound image.

Alternatively, when two types of ultrasound transmission and reception are used in spatial compounding as shown in FIGS. 31A and 31B, the image combining unit 80 combines two ultrasound images.

The image combining unit 80 performs no image composition in a frame where only one type of ultrasound transmission and reception is performed as seen in the example shown in FIG. 32B and an ultrasound image sent from the image processor 78 is used as the image signals of a composite ultrasound image.

The display controller 62 causes the monitor 64 to display the ultrasound image according to the image signals generated by the image generating unit 58.

Under the control of the display controller 62, the monitor 64 displays the ultrasound image.

The apparatus body controller 70 controls the components in the diagnostic apparatus body 14E. The apparatus body controller 70 is connected to the operating unit 72E to perform various input operations for the selection of the number of images to be combined or as to whether or not spatial compounding is to be performed.

The operation of the ultrasound diagnostic apparatus 10E shown in FIG. 29 is described below.

Similarly to the ultrasound diagnostic apparatus 10A, during the diagnosis, various kinds of information inputted to the operating unit 72E are first sent to the probe 12E by wireless communication and then supplied to the probe controller 38 also in the ultrasound diagnostic apparatus 10E.

Then, ultrasonic waves are transmitted from the transducers 18 in accordance with the drive voltage supplied from the transmission drive 30 of the probe 12E.

The reception signals outputted from the transducers 18 that have received the ultrasonic echoes generated by reflection of the ultrasonic waves on the subject are supplied to the corresponding individual signal processors 20a to generate sample data.

As described above, when spatial compounding is performed in the ultrasound diagnostic apparatus 10E, the probe 12E performs ultrasound transmission and reception so that the last ultrasound image in the earlier one of two temporally consecutive frames (i.e., composite ultrasound images) is made to coincide with the first ultrasound image in its subsequent frame in the directions of ultrasound transmission and reception.

For example, the transmission controller 32E and the reception controller 34E control the operations of the transmission drive 30 and the signal processor 20 (individual signal processors 20a) so that the transmission and reception for the "image B→image A→image C" and those for the "image C→image A→image B" are alternately repeated as shown in FIG. 30A.

Alternatively, two types of ultrasound transmission and reception may be used in one frame as shown in FIGS. 31A and 31B, or frames which are different in the number of types of ultrasound transmission and reception may coexist as shown in FIGS. 32A and 32B. In addition, the ultrasound transmission and reception may be shared between the last image in the earlier one of temporally adjacent frames and the first image in the subsequent frame as shown in FIGS. 33A and 33B.

The sample data generated by the individual signal processors 20a are sent to the parallel/serial converter 24, where the sample data is converted into serial data. The serial data is then wirelessly transmitted from the wireless communication unit 26 (antenna 28) to the diagnostic apparatus body 14E.

The sample data received by the wireless communication unit 52 of the diagnostic apparatus body 14E is converted into parallel data in the serial/parallel converter 54 and stored in the data storage unit 56.

Further, the sample data for each image is read out from the data storage unit 56 to generate image signals of an ultrasound image in the image generating unit 58. The display controller 62 causes the monitor 64 to display the ultrasound image based on the image signals.

When spatial compounding is performed, the image combining unit 80 of the image generating unit 58 combines the ultrasound images.

Figure 30C:
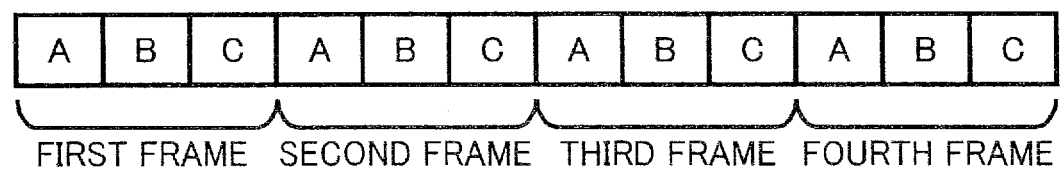
FIG. 30C is a conceptual diagram for illustrating normal spatial compounding.

More specifically, when spatial compounding is performed in the ultrasound transmission and reception as shown in FIGS. 30A to 30C, the image combining unit 80 combines the ultrasound image A derived from the transmission and reception for the image A, the ultrasound image B derived from the transmission and reception for the image B, and the ultrasound image C derived from the transmission and reception for the image C to generate image signals for a composite ultrasound image, and outputs the image signals to the display controller 62.

Alternatively, when two types of ultrasound transmission and reception are used in spatial compounding as shown in FIGS. 31A and 31B, two ultrasound images are combined to generate image signals of a composite ultrasound image. In a frame where only one type of ultrasound transmission and reception is performed as shown in FIG. 32B, an ultrasound image sent from the image processor 78 is not combined with other but is directly used as the image signals of a composite ultrasound image.

In the above-described embodiments, the illustrated ultrasound diagnostic apparatus 10A to 10E are each configured so that the probe has a means for controlling ultrasound transmission and reception and a means for processing reception signals obtained from ultrasonic echoes from a subject and the probe is connected to the diagnostic apparatus body by wireless communication. However, this is not the sole case of the invention.

This invention is also applicable to an ultrasound diagnostic apparatus configured so that a wired connection established between the ultrasound probe and the diagnostic apparatus body, the ultrasound probe only includes a piezoelectric unit and the diagnostic apparatus body controls the ultrasound transmission and reception.

However, as described above, this invention enables the control of the ultrasound transmission and reception to be simplified while suppressing the heat generation from the probe when spatial compounding is performed.

Therefore, when spatial compounding is performed, heat generation from or burden of the probe which is required to perform larger amounts of operation control and signal processing can be reduced by making use of the invention in an apparatus having a signal processing function and a mechanism for controlling ultrasound transmission and reception incorporated in the small probe, as exemplified by the illustrated ultrasound diagnostic apparatus in which the probe is wirelessly connected to the diagnostic apparatus body. Therefore, this invention can be advantageously used in an ultrasound diagnostic apparatus configured so that a probe includes a mechanism for controlling ultrasound transmission and reception.

The illustrated ultrasound diagnostic apparatus 10A to 10E individually include the spatial compounding functions in the first to fourth embodiments in the first aspect of the invention and the spatial compounding function in the second aspect of the invention. However, this is not the sole case of the invention.

In other words, the ultrasound diagnostic apparatus of the invention has two or more functions selected from the functions according to the first to fourth embodiments in the first aspect of the invention and the function in the second aspect of the invention so that a suitable mode can be selected to determine as to which spatial compounding function is to be performed.

While the ultrasound diagnostic apparatus of the invention has been described above in detail, the invention is by no means limited to the above embodiments, and various improvements and modifications may be made without departing from the scope and spirit of the invention.

What is claimed is:

1. An ultrasound diagnostic apparatus comprising:
   an ultrasound probe configured to transmit ultrasonic waves into a subject and receive ultrasonic echoes generated by reflection of the ultrasonic waves from the subject, the ultrasound probe including a signal processor for processing reception signals based on the ultrasonic echoes and a temperature sensor for measuring a temperature at a predetermined position; and
   a diagnostic apparatus body configured to generate ultrasound images in accordance with the reception signals processed in the signal processor of said ultrasound probe,
   wherein said ultrasound probe is configured to perform a plurality of types of ultrasound transmission and reception in mutually different directions of ultrasound transmission and reception and said diagnostic apparatus body is configured to combine ultrasound images based on each of the plurality of types of ultrasound transmission and reception, and
   wherein, upon production of the composite ultrasound image in said diagnostic apparatus body, said ultrasound probe performs the ultrasound transmission and reception for producing said composite ultrasound image through said plurality of types of ultrasound transmission and reception or through at least one type of ultrasound transmission and reception after reduction of one or more types of ultrasound transmission and reception from said plurality of types of ultrasound transmission and reception based on a temperature measurement result obtained with said temperature sensor.

2. The ultrasound diagnostic apparatus according to claim 1, wherein said temperature sensor measures a temperature of said signal processor.

3. The ultrasound diagnostic apparatus according to claim 1, wherein, upon the production of the composite ultrasound image in said diagnostic apparatus body, said ultrasound probe performs ultrasound transmission and reception for obtaining a main image as an ultrasound image in a preset predetermined output region by one of said plurality of types of ultrasound transmission and reception.

4. The ultrasound diagnostic apparatus according to claim 1,
   wherein the signal processor changes and sets a number of types of ultrasound transmission and reception in said mutually different directions of ultrasound transmission and reception depending on the temperature measurement result obtained with said temperature sensor, and the signal processor sets a temperature T1 and a temperature T2 higher than the temperature T1 as thresholds and, upon the production of the composite ultrasound image in said diagnostic apparatus body, depending on the temperature measurement result obtained with said temperature sensor, said ultrasound probe performs said plurality of types of ultrasound transmission and reception when the temperature measurement result is less than the temperature T1, performs a set minimum number of types of ultrasound transmission and reception when the temperature measurement result is equal to or more than the temperature T2, and performs a given number of types of ultrasound transmission and reception which is smaller than the number of said plurality of types of transmission and reception but is larger than the set minimum number of types of ultrasound transmission and reception when the temperature measurement result is equal to or more than the temperature T1 but less than the temperature T2.

5. The ultrasound diagnostic apparatus according to claim 1, wherein the signal processor changes and sets a number of types of ultrasound transmission and reception in said mutually different directions of ultrasound transmission and reception depending on the temperature measurement result obtained with said temperature sensor, and the signal processor sets a temperature T1 and a temperature T2 higher than the temperature T1 as thresholds and, upon the production of the composite ultrasound image in said diagnostic apparatus body, depending on the temperature measurement result obtained with said temperature sensor, said ultrasound probe performs said plurality of types of ultrasound transmission and reception when the temperature measurement result is less than the temperature T1, and when the temperature measurement result is equal to or more than said temperature T1, performs, in one ultrasound image, the at least one type of ultrasound transmission and reception after the reduction of the one or more types of ultrasound transmission and reception from said plurality of types of ultrasound transmission and reception and performs, in its temporally consecutive ultrasound image, said plurality of types of ultrasound transmission and reception or the at least one type of ultrasound transmission and reception after the reduction of the one or more types of ultrasound transmission and reception from said plurality of types of ultrasound transmission and reception, a specified number of types of ultrasound transmission and reception reduced from the number of said plurality of types of ultrasound transmission and reception being different in two consecutive ultrasound images including the one ultrasound image and its temporally consecutive ultrasound image.

6. The ultrasound diagnostic apparatus according to claim 5, wherein said ultrasound probe performs the specified number of types of the ultrasound transmission and reception by reducing the one or more types of ultrasound transmission and reception from said plurality of types of ultrasound transmission and reception in one of the two temporally consecutive ultrasound images when the temperature sensor has the temperature measurement result that is equal to or more than the temperature T1 but less than the temperature T2.

7. The ultrasound diagnostic apparatus according to claim 6, wherein said ultrasound probe performs the specified number of types of the ultrasound transmission and reception by reducing the one or more types of ultrasound transmission and reception from said plurality of types of ultrasound transmission and reception in both of the two temporally consecutive ultrasound images when the temperature sensor has the temperature measurement result that is equal to or more than the temperature T2.

8. The ultrasound diagnostic apparatus according to claim 1, wherein said ultrasound probe transmits and receives the ultrasonic waves in identical directions for a last ultrasound image in one composite ultrasound image and a first ultrasound image in its temporally consecutive ultrasound image.

9. The ultrasound diagnostic apparatus according to claim 1, wherein, upon the production of the composite ultrasound image in said diagnostic apparatus body, said ultrasound probe performs the ultrasound transmission and reception so as to reduce temporally consecutive ultrasound image when two or more types of ultrasound transmission and reception are reduced from said plurality of types of ultrasound transmission and reception.

10. The ultrasound diagnostic apparatus according to claim 1, wherein, upon the production of the composite ultrasound image in said diagnostic apparatus body, said ultrasound probe performs the ultrasound transmission and reception so as to reduce a last ultrasound image in a composite ultrasound image and a first ultrasound image in its temporally consecutive composite ultrasound image when the one or more types of ultrasound transmission and reception are reduced from said plurality of types of ultrasound transmission and reception.

11. The ultrasound diagnostic apparatus according to claim 1, wherein, upon the production of the composite ultrasound image in said diagnostic apparatus body, said ultrasound probe adjusts conditions of the ultrasound transmission and reception so as to change an image quality of an ultrasound image to be combined in said diagnostic apparatus body in accordance with the temperature measurement result obtained with said temperature sensor.

12. The ultrasound diagnostic apparatus according to claim 11, wherein said temperature sensor measures a temperature of said signal processor.

13. The ultrasound diagnostic apparatus according to claim 11, wherein said ultrasound probe changes at least one of a number of available channels and a number of sound rays to adjust the conditions of the ultrasound transmission and reception.

14. The ultrasound diagnostic apparatus according to claim 11, wherein a temperature T3 and a temperature T4 higher than the temperature T3 are set as thresholds, and wherein ultrasound transmission and reception at a normal image quality level corresponding to ultrasound images of predetermined image quality, ultrasound transmission and reception at a low image quality level corresponding to ultrasound images of lowest image quality, and ultrasound transmission and reception at a medium image quality level corresponding to ultrasound images having image quality lower than the normal image quality level but higher than the low image quality level are set in the conditions of the ultrasound transmission and reception for obtaining the ultrasound image to be combined.

15. The ultrasound diagnostic apparatus according to claim 14, wherein, upon the production of the composite ultrasound image in said diagnostic apparatus body, depending on the temperature measurement result obtained with said temperature sensor, said ultrasound probe performs all of said plurality of types of ultrasound transmission and reception at the normal image quality level when the temperature measurement result is less than the temperature T3.

16. The ultrasound diagnostic apparatus according to claim 15, wherein, upon the production of the composite ultrasound image in said diagnostic apparatus body, depending on the temperature measurement result obtained with said temperature sensor, said ultrasound probe performs at least two of said plurality of types of ultrasound transmission and reception at the medium image quality level when the temperature measurement result is equal to or more than the temperature T3 but less than the temperature T4 and at the low image quality level when the temperature measurement result is equal to or more than the temperature T4.

17. The ultrasound diagnostic apparatus according to claim 15, wherein, upon the production of the composite ultrasound image in said diagnostic apparatus body, depending on the temperature measurement result obtained with said temperature sensor, said ultrasound probe performs at least two of said plurality of types of ultrasound transmission and reception at the medium image quality level when the temperature measurement result is equal to or more than the temperature T3 but less than the temperature T4, and performs at least one of said plurality of types of ultrasound transmission and reception at the medium image quality level and one or more types of ultrasound transmission and reception except said at least one of said plurality of types of ultrasound transmission and reception at the low image quality level when the temperature measurement result is equal to or more than the temperature T4.

18. The ultrasound diagnostic apparatus according to claim 14, wherein, upon the production of the composite ultrasound image in said diagnostic apparatus body, depending on the temperature measurement result obtained with said temperature sensor, said ultrasound probe performs at least two of said plurality of types of ultrasound transmission and reception at the medium image quality level when the temperature measurement result is equal to or more than the temperature T3 but less than the temperature T4, and performs the at least two of said plurality of types of ultrasound transmission and reception at the low image quality level and all of one or more types of ultrasound transmission and reception except said at least two of said plurality of types of ultrasound transmission and reception at the medium image quality level when the temperature measurement result is equal to or more than the temperature T4.

19. The ultrasound diagnostic apparatus according to claim 14, wherein, upon the production of the composite ultrasound image in said diagnostic apparatus body, said ultrasound probe performs ultrasound transmission and reception for obtaining a main image as an ultrasound image in a preset predetermined output region by one of said plurality of types of ultrasound transmission and reception and wherein the ultrasound transmission and reception for the main image are performed at the normal image quality level.

20. The ultrasound diagnostic apparatus according to claim 11, wherein said ultrasound probe transmits and receives the ultrasonic waves in identical directions for a last ultrasound image in one composite ultrasound image and a first ultrasound image in its temporally consecutive composite ultrasound image.

21. The ultrasound diagnostic apparatus according to claim 1, wherein, upon the production of the composite ultrasound image in said diagnostic apparatus body, said ultrasound probe adjusts a depth of the reception signals to be processed by said signal processor so as to change a depth of an ultrasound image to be combined in said diagnostic apparatus body in accordance with the temperature measurement result obtained with said temperature sensor.

22. The ultrasound diagnostic apparatus according to claim 21, wherein said temperature sensor measures a temperature of said signal processor.

23. The ultrasound diagnostic apparatus according to claim 21, wherein a temperature T5 and a temperature T6 higher than the temperature T5 are set as thresholds and wherein a normal depth according to which the reception signals are processed up to a predetermined depth, a small depth according to which the reception signals are processed up to a shallowest depth and a medium depth according to which the reception signals are processed up to a depth smaller than said normal depth but larger than said small depth are set for the depth of the reception signals to be processed by said signal processor.

24. The ultrasound diagnostic apparatus according to claim 23, wherein, upon the production of the composite ultrasound image in said diagnostic apparatus body, depending on the temperature measurement result obtained with said temperature sensor, said ultrasound probe performs all of reception signal processing in said plurality of types of ultrasound transmission and reception up to the normal depth when the temperature measurement result is less than the temperature T5.

25. The ultrasound diagnostic apparatus according to claim 24, wherein, upon the production of the composite ultrasound image in said diagnostic apparatus body, depending on the temperature measurement result obtained with said temperature sensor, said ultrasound probe performs reception signal processing in at least two of said plurality of types of ultrasound transmission and reception up to the medium depth when the temperature measurement result is equal to or more than the temperature T5 but less than the temperature T6 and up to the small depth when the temperature measurement result is equal to or more than the temperature T6.

26. The ultrasound diagnostic apparatus according to claim 24, wherein, upon the production of the composite ultrasound image in said diagnostic apparatus body, depending on the temperature measurement result obtained with said temperature sensor, said ultrasound probe performs reception signal processing at least two of said plurality of types of ultrasound transmission and reception up to the medium depth when the temperature measurement result is equal to or more than the temperature T5 but less than the temperature T6, and alternately repeats reception signal processing up to the small depth in at least two of said plurality of types of ultrasound transmission and reception and reception signal processing up to the medium depth in the at least two of said plurality of types of ultrasound transmission and reception in temporally consecutive composite ultrasound images when the temperature measurement result is equal to or more than the temperature T6.

27. The ultrasound diagnostic apparatus according to claim 24, wherein, upon the production of the composite ultrasound image in said diagnostic apparatus body, depending on the temperature measurement result obtained with said temperature sensor, said ultrasound probe performs reception signal processing in at least two of said plurality of types of ultrasound transmission and reception up to the medium depth when the temperature measurement result is equal to or more than the temperature T5 but less than the temperature T6 and performs reception signal processing in at least one of said plurality of types of ultrasound transmission and reception up to the medium depth and one or more types of ultrasound transmission and reception except said at least one of said plurality of types of ultrasound transmission and reception up to the small depth when the temperature measurement result is equal to or more than the temperature T6.

28. The ultrasound diagnostic apparatus according to claim 27, wherein ultrasound images subjected to the reception signal processing up to said medium depth and ultrasound images subjected to the reception signal processing up to said small depth are different in order of processing in temporally consecutive composite ultrasound images when the temperature measurement result is equal to or more than the temperature T6.

29. The ultrasound diagnostic apparatus according to claim 24, wherein, upon the production of the composite ultrasound image in said diagnostic apparatus body, depending on the temperature measurement result obtained with said temperature sensor, said ultrasound probe performs reception signal processing in at least two of said plurality of types of ultrasound transmission and reception up to the medium depth when the temperature measurement result is equal to or more than the temperature T5 but less than the temperature T6 and performs the reception signal processing in the at least two of said plurality of types of ultrasound transmission and reception up to the small depth and all of one or more types of ultrasound transmission and reception except said at least two of said plurality of types of ultrasound transmission and reception up to the medium depth when the temperature measurement result is equal to or more than the temperature T6.

30. The ultrasound diagnostic apparatus according to claim 23, wherein, upon the production of the composite ultrasound image in said diagnostic apparatus body, said ultrasound probe performs ultrasound transmission and reception for obtaining a main image as an ultrasound image in a preset predetermined output region by one of said plurality of types of ultrasound transmission and reception and wherein reception signals obtained by the ultrasound transmission and reception for the main image are processed up to the normal depth.

31. The ultrasound diagnostic apparatus according to claim 21, wherein said ultrasound probe transmits and receives the ultrasonic waves in identical directions for a last ultrasound image in one composite ultrasound image and a first ultrasound image in its temporally consecutive composite ultrasound image.

32. The ultrasound diagnostic apparatus according to claim 1, wherein, upon the production of the composite ultrasound image in said diagnostic apparatus body, said ultrasound probe adjusts reception signal processing performed by said signal processor so as to reduce a number of sound rays in a region beyond a predetermined depth in an ultrasound image to be combined by said diagnostic apparatus body depending on the temperature measurement result obtained with said temperature sensor, and wherein, upon the production of the composite ultrasound image in said diagnostic apparatus body, said diagnostic apparatus body interpolates sound rays eliminated beyond said predetermined depth with their surrounding sound rays to produce said ultrasound image.

33. The ultrasound diagnostic apparatus according to claim 32, wherein said temperature sensor measures a temperature of said signal processor.

34. The ultrasound diagnostic apparatus according to claim 32, wherein a temperature T7 and a temperature T8 higher than the temperature T7 are set as thresholds, and wherein a normal depth up to which the number of sound rays is not reduced, a small depth which is shallowest, and a medium depth which is smaller than said normal depth but is larger than said small depth are set for the predetermined depth beyond which the number of sound rays is reduced.

35. The ultrasound diagnostic apparatus according to claim 34, wherein, upon the production of the composite ultrasound image in said diagnostic apparatus body, depending on the temperature measurement result obtained with said temperature sensor, said ultrasound probe processes all of ultrasound images up to the normal depth when the temperature measurement result is less than the temperature T7.

36. The ultrasound diagnostic apparatus according to claim 35, wherein, upon the production of the composite ultrasound image in said diagnostic apparatus body, depending on the temperature measurement result obtained with said temperature sensor, said ultrasound probe reduces the number of sound rays beyond said medium depth in at least two of ultrasound images when the temperature measurement result is equal to or more than the temperature T7 but less than the temperature T8, and reduces the number of sound rays beyond said small depth in the at least two of ultrasound images when the temperature measurement result is equal to or more than the temperature T8.

37. The ultrasound diagnostic apparatus according to claim 35, wherein, upon the production of the composite ultrasound image in said diagnostic apparatus body, depending on the temperature measurement result obtained with said temperature sensor, said ultrasound probe reduces the number of sound rays beyond said medium depth in at least two of ultrasound images when the temperature measurement result is equal to or more than the temperature T7 but less than the temperature T8, and reduces the number of sound rays beyond said medium depth in at least one of ultrasound images and one or more ultrasound images except said at least one of ultrasound images beyond said small depth when the temperature measurement result is equal to or more than the temperature T8.

38. The ultrasound diagnostic apparatus according to claim 35, wherein, upon the production of the composite ultrasound image in said diagnostic apparatus body, depending on the temperature measurement result obtained with said temperature sensor, said ultrasound probe reduces the number of sound rays beyond said medium depth in at least two of ultrasound images when the temperature measurement result is equal to or more than the temperature T7 but less than the temperature T8, and reduces the number of sound rays beyond said small depth in the at least two of ultrasound images and all of one or more ultrasound images except said at least two of ultrasound images beyond said medium depth when the temperature measurement result is equal to or more than the temperature T8.

39. The ultrasound diagnostic apparatus according to claim 34,
  wherein, upon the production of the composite ultrasound image in said diagnostic apparatus body, said ultrasound probe performs ultrasound transmission and reception for obtaining a main image as an ultrasound image in a preset predetermined output region by one of said plurality of types of ultrasound transmission and reception and
  wherein an ultrasound image obtained by the ultrasound transmission and reception for the main image has the normal depth.

40. The ultrasound diagnostic apparatus according to claim 32, wherein said ultrasound probe transmits and receives the ultrasonic waves in identical directions for a last ultrasound image in one composite ultrasound image and a first ultrasound image in its temporally consecutive composite ultrasound image.

41. The ultrasound diagnostic apparatus according to claim 1, wherein,
  wherein said temperature sensor measures a temperature of said signal processor, and
  an internal temperature of the ultrasound probe is controlled based on heat generation in the signal processor as indicated by the measured temperature of said signal processor, the signal processor changing a number of types of ultrasound transmission and reception in said mutually different directions of ultrasound transmission and reception depending on the measured temperature of said signal processor, including
  i) reducing the number of types of ultrasound transmission and reception in said mutually different directions of ultrasound transmission and reception to a first reduced number of types when the measured temperature of said signal processor increases over a first threshold temperature, and
  ii) reducing the number of types of ultrasound transmission and reception in said mutually different directions of ultrasound transmission and reception to a second reduced number of types when the measured temperature of said signal processor increases over a second threshold temperature, the second reduced number of types being less than the first reduced number of types and the second threshold temperature being greater than the first threshold temperature.

\* \* \* \* \*